United States Patent
Stansfield et al.

(10) Patent No.: US 8,101,595 B2
(45) Date of Patent: *Jan. 24, 2012

(54) ANTIVIRAL INDOLES

(75) Inventors: Ian Stansfield, Rome (IT); Uwe Koch, Rome (IT); Joerg Habermann, Rome (IT); Frank Narjes, Rome (IT)

(73) Assignee: Istituto di Ricerche di Biologia Molecolare P. Angletti SpA, Rome (IT)

( * ) Notice: Subject to any disclaimer, the term of this patent is extended or adjusted under 35 U.S.C. 154(b) by 275 days.

This patent is subject to a terminal disclaimer.

(21) Appl. No.: 12/519,570

(22) PCT Filed: Dec. 19, 2007

(86) PCT No.: PCT/GB2007/050767

§ 371 (c)(1),
(2), (4) Date: Jun. 17, 2009

(87) PCT Pub. No.: WO2008/075103

PCT Pub. Date: Jun. 26, 2008

(65) Prior Publication Data

US 2010/0076046 A1 Mar. 25, 2010

(30) Foreign Application Priority Data

Dec. 20, 2006 (GB) .................................. 0625345.4
Dec. 20, 2006 (GB) .................................. 0625349.6

(51) Int. Cl.
C07D 267/22 (2006.01)
A61K 31/55 (2006.01)
A61P 31/22 (2006.01)

(52) U.S. Cl. .............. 514/183; 514/211.09; 514/214.02; 514/219; 540/457

(58) Field of Classification Search .................. 540/457; 514/183, 211.09, 214.02, 219
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,608,027 B1 | 8/2003 | Tsantrizos et al. | |
| 6,777,395 B2 | 8/2004 | Bhat et al. | |
| 6,955,174 B2 | 10/2005 | Joye et al. | |
| 7,470,664 B2 | 12/2008 | Holloway et al. | |
| 2002/0019363 A1 | 2/2002 | Ismaili et al. | |
| 2002/0107138 A1 | 8/2002 | Hoveyda et al. | |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |
| 2004/0229776 A1 | 11/2004 | Chen et al. | |
| 2004/0229818 A1 | 11/2004 | Llinas-Brunet et al. | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2006/0257980 A1 | 11/2006 | Li | |
| 2007/0027071 A1 | 2/2007 | Holloway et al. | |

FOREIGN PATENT DOCUMENTS

| | | |
|---|---|---|
| EP | 1719773 A1 | 11/2006 |
| GB | 2337262 A | 11/1999 |
| GB | 2430621 A | 4/2007 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |
| WO | 01/60379 A1 | 8/2001 |

(Continued)

OTHER PUBLICATIONS

Brian W Dymock et al., "Novel Approaches to the Treatment of Hepatitis C Virus Infection," 11 Antiviral Chemistry & Chemotherapy 79-96 (2000). Hugo R. Rosen & David R. Gretch, "Hepatitis C virus: current understanding and prospects for future therapies," 5 Molec. Med. Today 393-99 (1999).
Darius Moradpour & Hubert E. Blum, "Current and evolving therapies for hepatitis C," 11 Euro. J. Gastroenterol. Hepatol. 1189-1202 (1999).
Ralf Bartenschlager, "Candidate Targets for Hepatitis C Virus-Specific Antiviral Therapy," 40(5-6) Intervirology 378-93 (1997).
Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).
Brain W. Dymock, "Emerging therapies for hepatitis C virus infection," 6 Emerging Drugs 13-42 (2001).
Charlene Crabb, Infectious Diseases. "Hard-Won Advances Spark Excitement about Hepatitis C," Science 506-507 (2001).

(Continued)

*Primary Examiner* — Bruck Kifle
(74) *Attorney, Agent, or Firm* — Julie M. Lake; Sheldon O. Heber

(57) ABSTRACT

Compounds of the formula (I) wherein A, B, D, M, Ar, W, X, Y, Z and $R^1$ are as defined herein, are useful in the prevention and treatment of hepatitis C infections. The compounds, their preparation, pharmaceutical compositions containing them and their use in medicine are disclosed.

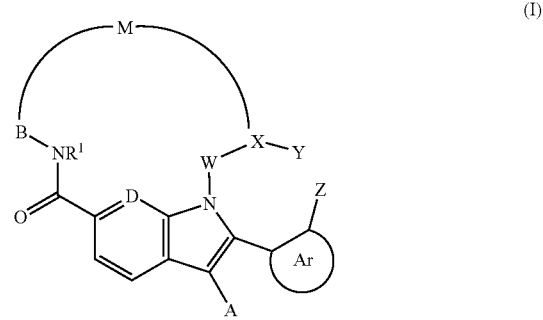

(I)

19 Claims, No Drawings

FOREIGN PATENT DOCUMENTS

| | | |
|---|---|---|
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A2 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Rogers E. Harry-O'Kuru et al., "A Short, Flexible Route toward 2'-C-Branched Ribonucleosides," 62 J. Org. Chem. 1754-59 (1997).

Michael S. Wolfe & Rogers E. Harry-O'Kuru, "A Concise Synthesis of 2'-C-Methylribonucleosides," 36(42) Tetrahedron Letters 7611-14 (1995).

Scott J. Miller et al., "Application of Ring-Closing Metathesis to the Synthesis of Rigidified Amino Acids and Peptides," 118 J. Am. Chem. Soc. 9606-14 (1996).

Jason S. Kingsbury et al., "A Recyclable Ru-Based Metathesis Catalyst," 121 J. Am. Chem. Soc. 791-99 (1999).

Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).

Alois Furstner et al., "Total Synthesis and Structural Refinement of the Cyclic Tripyrrole Pigment Nonylprodigiosin," 64 J. Org. Chem. 8275-80 (1999).

Tina M. Trnka & Robert H. Grubbs, "The Development of L2X2R-CHR Olefin Metathesis Catalysts: An Organometallic Success Story," 34 Acc. Chem. Res. 18-29 (2001).

A. Srikrishna et al., "Enantiospecific Construction of the BC-ring System of Taxanes," 45 Tetrahedron Letters 2939-42 (2004).

Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).

Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).

Paola Conti et al., "Chemoenzymatic Synthesis of the Enantiomers of Desoxymuscarine," 9 Tetrahedron: Asymmetry 657-65 (1998).

Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).

D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. K Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

Youwei Yan et al., Complex of NS3 protease and NS4A peptide of BK strain hepatitis C virus: A 2.2 Angstrom resolution structure in a hexagonal crystal form, 7 Protein Science 837 (1998).

Youla S. Tsantrizos, The Design of a Potent Inhibitor of the Hepatitis C Virus NS3 Protease: BILN 2061—From the NMR Tube to the Clinic, Biopolymers (Peptide Science), vol. 76, pp. 309-323 (2004).

ANTIVIRAL INDOLES

CROSS-REFERENCE TO RELATED APPLICATIONS

This application is a National Stage application of International application PCT/GB2007/050767, filed Dec. 19, 2007. This application also claims priority to British Provisional application GB 0625345.4, filed Dec. 20, 2006, and British Provisional application GB 0625349.6, filed Dec. 20, 2006.

FIELD OF THE INVENTION

The present invention relates to macrocyclic indole compounds, to pharmaceutical compositions containing them, to their use in the prevention and treatment of hepatitis C infections and to methods of preparation of such compounds and compositions.

Hepatitis C (HCV) is a cause of viral infections. There is as yet no adequate treatment for HCV infection but it is believed that inhibition of its RNA polymerase in mammals, particularly humans, would be of benefit.

BACKGROUND OF THE INVENTION

International patent application publication WO 93/00334 (Fidia-Georgetown Institute for the Neurosciences) discloses the following indole derivatives:

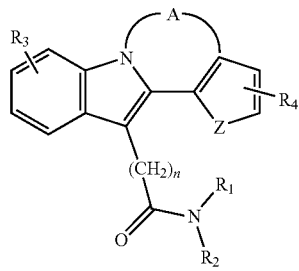

where A, Z, $R_1$, $R_2$, $R_3$, $R_4$ and n are defined therein, as useful in compositions and methods for treating psychiatric and neurological disorders. However, this document does not disclose the use of tetracyclic indole derivatives in treating or preventing viral infections.

International patent application publication WO 2005/080399 (Japan Tobacco Inc.) discloses the following fused heterotetracyclic compounds:

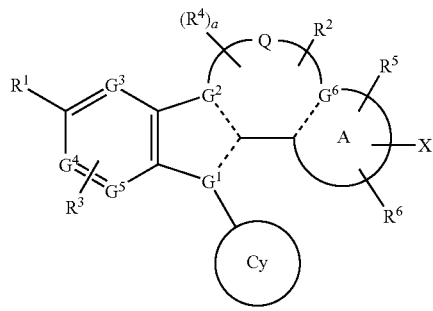

where A, X, Cy, $G^1$, $G^2$, $G^3$, $G^4$, $G^5$, $G^6$, $R^1$, $R^2$, $R^3$, $R^4$, $R^5$, $R^6$ and a are defined therein, and their use as HCV polymerase inhibitors.

International patent application publication WO 2006/020082(Bristol-Myers Squibb Company) discloses the following fused tetracyclic compounds:

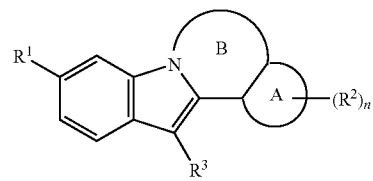

where A, B, $R^1$, $R^2$, $R^3$ and n are defined therein, and their use in treating hepatitis C.

International patent application publication WO2006/046030 and WO2006/046039 (both Istituto Di Ricerche Di Biologia Molecolare P. Angeletti SpA) disclose certain tetracyclic indole derivatives:

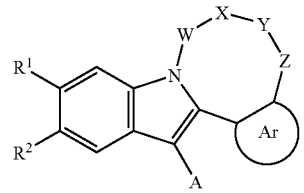

wherein $R^1$, $R^2$, A, Ar, W, X, Y, and Z are defined therein, useful for the treatment or prevention of infection by hepatitis C virus. International patent application publications WO2007/029029 and WO2007/054741 (both Istituto Di Ricerche Di Biologia Molecolare P. Angeletti SpA) disclose structurally related tetracyclic indole derivatives, useful for the treatment or prevention of infection by hepatitis C virus.

SUMMARY OF THE INVENTION

Thus, the present invention provides the compound of the formula (I):

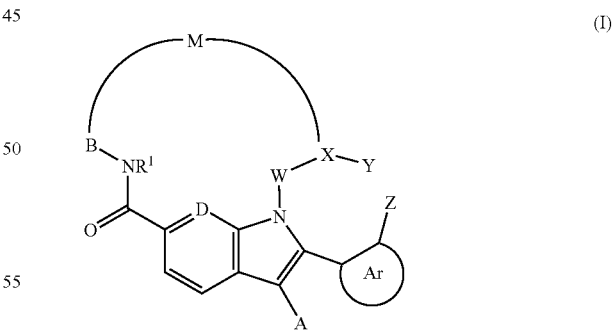

wherein

Ar is a moiety containing at least one aromatic ring and possesses 5-, 6-, 9- or 10-ring atoms optionally containing 1, 2 or 3 heteroatoms independently selected from N, O and S, which ring is optionally substituted by groups $Q^1$ and $Q^2$;

$Q^1$ is halogen, hydroxy, $C_{1-6}$alkyl, $C_{1-6}$alkoxy, aryl, heteroaryl, $CONR^aR^b$, $(CH_2)_{0-3}NR^aR^b$, $O(CH_2)_{1-3}NR^aR^b$, $O(CH_2)_{0-3}CONR^aR^b$, $O(CH_2)_{0-3}$aryl, $O(CH_2)_{0-3}$heteroaryl, $O(CR^eR^f$aryl, $O(CR^eR^f)$heteroaryl or $OCHR^cR^d$;

$R^a$ and $R^b$ are each independently selected from hydrogen, $C_{1-4}$alkyl and $C(O)C_{1-4}$alkyl;

or $R^a$, $R^b$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

$R^c$ and $R^d$ are each independently selected from hydrogen and $C_{1-4}$alkoxy;

or $R^c$ and $R^d$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$R^e$ is hydrogen or $C_{1-6}$alkyl;

$R^f$ is $C_{1-6}$alkyl;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;

A is $C_{3-6}$alkyl or $C_{2-6}$alkenyl, or A is a non-aromatic ring of 3 to 8 ring atoms where said ring may contain a double bond and/or may contain a O, S, SO, $SO_2$ or NH moiety, or A is a non-aromatic bicyclic moiety of 4 to 8 ring atoms, and A is optionally substituted by halogen, hydroxy, $C_{1-4}$alkyl or $C_{1-4}$alkoxy;

D is N or $CR^g$;

$R^g$ is hydrogen, fluorine, chlorine, $C_{1-4}$alkyl, $C_{2-4}$alkenyl or $C_{1-4}$alkoxy, where said $C_{1-4}$alkyl, $C_{2-4}$alkenyl and $C_{1-4}$alkoxy groups are optionally substituted by hydroxy or fluorine;

W is a bond, C=O, O, $S(O)_{0-2}$ or $—(CR^{10}R^{11})—(CR^{12}R^{13})_{0-1}—$;

X is $—CR^{14a}—$ or N; Y is a bond, C=O, O, $—CR^{14}R^{15}—$ or $NR^{14}$; and Z is a bond, C=O, O, $S(O)_{0-2}$, $—(CR^{10}R^{11})—(CR^{12}R^{13})_{0-1}—$ or $NR^{10}$; and none, one or two of W, Y and Z are a bond;

or X is C=O, $—CR^{14b}R^{15b}—$ or $NR^{14b}$; and Y is hydrogen or absent and Z is hydrogen or a group $Q^1$ or $Q^2$ $R^{10}$, $R^{11}$, $R^{12}$, $R^{13}$, $R^{14}$, $R^{14a}$, $R^{14b}$, $R^{15}$ and $R^{15b}$ are each independently selected from hydrogen, hydroxy, $C_{1-6}$alkyl, $C_{2-6}$alkenyl, $C_{1-6}$alkoxy, $C(O)C_{1-6}$alkyl, Het, $(CH_2)_{0-3}NR^{16}R^{17}$, $C(O)(CH_2)_{0-3}NR^{16}R^{17}$, $NHC(O)(CH_2)_{0-3}NR^{16}R^{17}$, $O(CH_2)_{1-3}NR^{16}R^{17}$, $S(O)_{0-2}(CH_2)_{0-3}NR^{16}R^{17}$ and $C(O)(CH_2)_{0-3}R^{16}$;

or one of $R^{10}$, $R^{14}$, $R^{14a}$ is linked to $R^{22}$ or $R^{23}$ to form a ring of 4 to 10 atoms, where said ring is optionally substituted by halogen, hydroxy, $C_{1-4}$alkyl or $C_{1-4}$alkoxy;

or, when X is $—CR^{14a}—$ and Z is $—CR^{10}R^{11}—$ or $NR^{10}$, $R^{10}$ is joined to $R^{14a}$ to form a $—(CH_2)—_{1-4}$ group, optionally substituted by $C_{1-4}$alkyl;

Het is a heteroaliphatic ring of 4 to 7 ring atoms, which ring may contain 1, 2 or 3 heteroatoms selected from N, O or S or a group S(O), $S(O)_2$, NH or $NC_{1-4}$alkyl;

$R^{16}$ and $R^{17}$ are independently selected from hydrogen, $C_{1-6}$alkyl and $(CH_2)_{0-4}NR^{18}R^{19}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$ alkyl, and which ring is optionally substituted by halogen, hydroxy, $C_{1-4}$alkyl or $C_{1-4}$alkoxy;

$R^{18}$ and $R^{19}$ are independently selected from hydrogen and $C_{1-6}$alkyl;

or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$ alkyl, and which ring is optionally substituted by halogen, hydroxy, $C_{1-4}$alkyl or $C_{1-4}$alkoxy;

$R^1$ is hydrogen or $C_{1-6}$alkyl;

B is $—CR^{20}R^{21}—$, $—C(=O)—$, $—SO—$ or $—SO_2—$;

$R^{20}$ and $R^{21}$ are independently selected from hydrogen and $C_{1-6}$alkyl;

or $R^{20}$ and $R^{21}$, together with the carbon atom to which they are joined, form a $C_{3-6}$cycloalkyl group;

M is $C_{4-8}$alkylene or $C_{4-8}$alkenylene, optionally substituted by $R^{22}$, where 1, 2 or 3 of the carbon atoms in the $C_{4-8}$alkylene or $C_{4-8}$alkenylene groups is optionally replaced by O, $NR^{23}$, S, SO, $SO_2$, piperidinyl, piperazinyl or pyrrolidinyl, where each $R^{23}$ is independently hydrogen, $C_{1-6}$alkyl, $C_{2-6}$alkenyl, $(CH_2)_{0-3}C_{3-6}$cycloalkyl, $(CH_2)_{1-3}OH$, $C_{1-6}$alkoxy, $C(O)C_{1-6}$alkyl, $(CH_2)_{0-3}$aryl, $(CH_2)_{0-3}$Het, $(CH_2)_{0-3}$heteroaryl, $(CH_2)_{1-3}NR^{16}R^{17}$, $C(O)(CH_2)_{1-3}NR^{16}R^{17}$, $S(O)_{0-2}(CH_2)_{1-3}NR^{16}R^{17}$, $C(O)(CH_2)_{1-3}OR^{16}$, $(CH_2)_{1-3}O(CH_2)_{0-3}$aryl, or $R^{23}$ is linked to one of $R^{10}$, $R^{14}$, $R^{14a}$ and $R^{14b}$ to form a ring of 4 to 10 atoms as hereinbefore described;

or where 2 or 3 of the carbon atoms in the $C_{4-8}$alkylene or $C_{4-8}$alkenylene group are replaced by $NR^{23}$, then the $R^{23}$ groups can be joined to form a $—(CH_2)—_{1-3}$ group, optionally substituted by $C_{1-2}$alkyl, where $R^{22}$ is halo, $C_{1-4}$alkyl, $(CH_2)_{0-3}C_{3-8}$cycloalkyl, $(CH_2)_{0-3}$ aryl, $(CH_2)_{0-3}$heteroaryl, $(CH_2)_{0-3}$Het, oxo or $(CH_2)_{0-3}NR^{16}R^{17}$, or $R^{22}$ is linked to one of $R^{10}$, $R^{14}$, $R^{14a}$ and $R^{14b}$ to form a ring of 4 to 10 atoms as hereinbefore described;

and pharmaceutically acceptable salts thereof.

DETAILED DESCRIPTION OF THE INVENTION

In an embodiment of the invention, there is provided the compound of the formula (Ia):

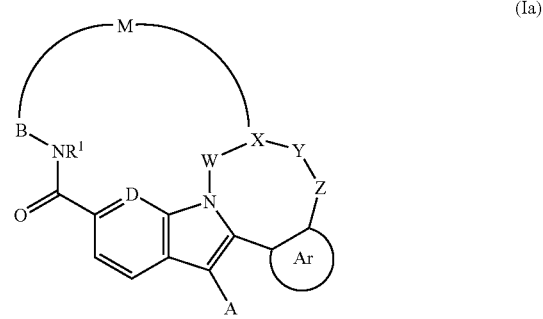

(Ia)

wherein X is $—CR^{14a}—$ or N; Y is a bond, C=O, O, $—CR^{14}R^{15}—$ or $NR^{14}$; and Z is a bond, C=O, $S(O)_{0-2}$, $—(CR^{10}R^{11})—(CR^{12}R^{13})_{0-1}—$ or $NR^{10}$; and none, one or two of W, Y and Z are a bond; and A, B, D, Ar, M, W and $R^1$ are as hereinbefore defined.

In one embodiment of the present invention, there is provided the compound of the formula (Iao):

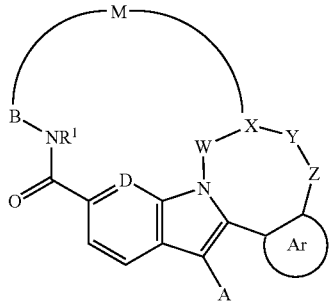

(Iao)

wherein Ar, $Q^1$, $Q^2$, A, D, W, Y, $R^1$ and B are as defined in relation to formula (I);

Z is a bond, C=O, O, $S(O)_{0-2}$, $-(CR^{10}R^{11})-(CR^{12}R^{13})_{0-1}-$ or $NR^{10}$;

and none, one or two of W, Y and Z are a bond;

X is $-CR^{14a}-$ or N;

$R^{10}$, $R^{11}$, $R^{12}$, $R^{13}$, $R^{14}$, $R^{14a}$ and $R^{15}$ are each independently selected from hydrogen, hydroxy, $C_{1-6}$alkyl, $C_{2-6}$alkenyl, $C_{1-6}$alkoxy, $C(O)C_{1-6}$alkyl, Het, $(CH_2)_{0-3}NR^{16}R^{17}$, $C(O)(CH_2)_{0-3}NR^{16}R^{17}$, $NHC(O)(CH_2)_{0-3}NR^{16}R^{17}$, $O(CH_2)_{1-3}NR^{16}R^{17}$, $S(O)_{0-2}(CH_2)_{0-3}R^{16}R^{17}$ and $C(O)(CH_2)_{0-3}O R^{16}$;

or one of $R^{10}$, $R^{14}$ and $R^{14a}$ is linked to $R^{22}$ or $R^{23}$ to form a ring of 4 to 10 atoms, where said ring is optionally substituted by halogen, hydroxy, $C_{1-4}$alkyl or $C_{1-4}$alkoxy;

Het is a heteroaliphatic ring of 4 to 7 ring atoms, which ring may contain 1, 2 or 3 heteroatoms selected from N, O or S or a group S(O), $S(O)_2$, NH or $NC_{1-4}$alkyl;

$R^{16}$ and $R^{17}$ are independently selected from hydrogen, $C_{1-6}$alkyl and $(CH_2)_{0-4}NR^{18}R^{19}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

$R^{18}$ and $R^{19}$ are independently selected from hydrogen and $C_{1-6}$alkyl;

or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

M is $C_{4-8}$alkylene or $C_{4-8}$alkenylene, optionally substituted by $R^{22}$, where 1, 2 or 3 of the carbon atoms in the $C_{4-8}$alkylene or $C_{4-8}$alkenylene groups is optionally replaced by O, $NR^{23}$, S, SO, $SO_2$, piperidinyl, piperazinyl or pyrrolidinyl, where $R^{23}$ is hydrogen or $C_{1-6}$alkyl, or $R^{23}$ is linked to one of $R^{10}$, $R^{14}$ and $R^{14a}$ to form a ring of 4 to 10 atoms as hereinbefore described;

where $R^{22}$ is halo, $C_{1-4}$alkyl, $(CH_2)_{0-3}C_{3-8}$cycloalkyl, $(CH_2)_{0-3}$aryl, $(CH_2)_{0-3}$heteroaryl, $(CH_2)_{0-3}$Het or oxo, or $R^{22}$ is linked to one of $R^{10}$, $R^{14}$ and $R^{14a}$ to form a ring of 4 to 10 atoms as hereinbefore described;

and pharmaceutically acceptable salts thereof.

In a further embodiment, Z is a bond, C=O, O, $-(CR^{10}R^{11})-(CR^{12}R^{13})_{0-1}-$ or $NR^{10}$ where $R^{10}$, $R^{11}$, $R^{12}$ and $R^{13}$ are as hereinbefore defined. Preferably, Z is a bond, O or $-(CR^{10}R^{11})-(CR^{12}R^{13})_{0-1}-$. More preferably, Z is a bond, O, $-CH_2-$ or $-CH_2CH_2-$. Most preferably, Z is O. Suitable examples of Z groups are O, $NCH_3$ and $CH_2$.

In a further embodiment, Y is a bond, C=O, O, $-CR^{14}R^{15}$ or $NR^{14}$ where $R^{14}$ and $R^{15}$ are as hereinbefore defined. Preferably, Y is C=O, O, $CR^{14}R^{15}$ or $-NR^{14}$. More preferably, Y is O, $-CR^{14}R^{15}-$ or $NR^{14}$. Most preferably, Y is $-CH_2-$, NH, $N(C_{1-6}alkyl)$, $NCH_2CH_2N(C_{1-6}alkyl)_2$ or $NC(O)(CH_2)_{1-2}N(C_{1-6}alkyl)_2$. Especially, Y is $-CH_2-$, NH, $N(C_{1-4}alkyl)$, $N(CH_2)_2N(C_{1-4}alkyl)_2$ or $NC(O)CH_2N(C_{1-4}alkyl)_2$. More especially, Y is $-CH_2-$, $NCH_3$ or $N(CH_2)_2N(CH_3)_2$. Most especially, Y is $-CH_2-$. Suitable examples of Y groups are $CH_2$ and a bond.

In a further embodiment, X is $-CR^{14}-$, where $R^{14}$ is as hereinbefore defined. Preferably, X is $-CH-$ or $-C(C_{1-6}alkyl)-$. More preferably, X is $-CH-$.

In a further embodiment, when X is $-CR^{14}-$, where $R^{14}$ is as hereinbefore defined. Preferably, X is $-CH-$ or $-C(C_{1-6}alkyl)-$. More preferably, X is $-CH-$.

In a further embodiment, when X is $-CR^{14a}-$ and Z is $-CR^{10}R^{11}-$ or $NR^{10}$, $R^{10}$ is joined to $R^{14a}$ to form a $-(CH_2)_{1-3}$ group, optionally substituted by $C_{1-3}$alkyl. Preferably, $R^{10}$ is joined to $R^{14a}$ to form a $-(CH_2)_{1-2}$ group, optionally substituted by $C_{1-2}$alkyl. More preferably, $R^{10}$ is joined to $R^{14a}$ to form a $-CH_2-$ group, optionally substituted by methyl. Especially, $R^{10}$ is joined to $R^{14a}$ to form a $-CH_2-$ group.

In an alternative embodiment, there is provided the compound of the formula (Ib):

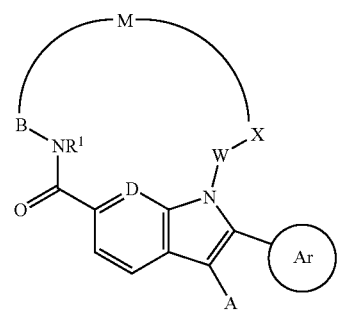

(Ib)

wherein X is C=O, O, $-CR^{14b}R^{15b}-$ or $NR^{14b}$; and A, B, D, Ar, M, W, $R^1 R^{14b} R^{15b}$ are as hereinbefore defined.

In one embodiment, the present invention provides the compound of formula (Ibo):

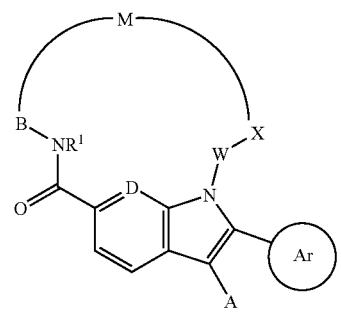

(Ibo)

wherein Ar is a moiety containing at least one aromatic ring and possesses 5-, 6-, 9- or 10-ring atoms optionally containing 1, 2 or 3 heteroatoms independently selected from N, O and S, which ring is optionally substituted by groups $Q^1$ and $Q^2$;

$Q^1$ is halogen, hydroxy, $C_{1-6}$alkyl, $C_{1-6}$alkoxy, aryl, heteroaryl, $CONR^aR^b$, $(CH_2)_{0-3}NR^aR^b$, $O(CH_2)_{1-3}NR^aR^b$, $O(CH_2)_{0-3}CONR^aR^b$, $O(CH_2)_{0-3}$aryl, $O(CH_2)_{0-3}$heteroaryl, $O(CR^eR^f)$aryl, $O(CR^eR^f)$heteroaryl or $OCHR^eR^d$;

$R^a$ and $R^b$ are each independently selected from hydrogen, $C_{1-4}$alkyl and $C(O)C_{1-4}$alkyl;

or $R^a$, $R^b$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

$R^c$ and $R^d$ are each independently selected from hydrogen and $C_{1-4}$alkoxy;

or $R^c$ and $R^d$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and wherein said $C_{1-4}$alkyl, $C_{1-4}$alkoxy and aryl groups are optionally substituted by halogen or hydroxy;

$R^e$ is hydrogen or $C_{1-6}$alkyl;

$R^f$ is $C_{1-6}$alkyl;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked by a bond or a heteroatom selected from N, O and S to form a ring of 4 to 7 atoms, where said ring is optionally substituted by halogen, hydroxy, $C_{1-4}$alkyl or $C_{1-4}$alkoxy;

A is $C_{3-6}$alkyl or $C_{2-6}$alkenyl, or A is a non-aromatic ring of 3 to 8 ring atoms where said ring may contain a double bond and/or may contain a O, S, SO, $SO_2$ or NH moiety, or A is a non-aromatic bicyclic moiety of 4 to 8 ring atoms, and A is optionally substituted by halogen, hydroxy, $C_{1-4}$alkyl or $C_{1-4}$alkoxy;

D is N or $CR^g$;

$R^g$ is hydrogen, fluorine, chlorine, $C_{1-4}$alkyl, $C_{2-4}$alkenyl or $C_{1-4}$alkoxy, where said $C_{1-4}$alkyl, $C_{2-4}$alkenyl and $C_{1-4}$alkoxy groups are optionally substituted by hydroxy or fluorine;

W is a bond, C=O, O, $S(O)_{0-2}$ or —$(CR^{10}R^{11})$—$(CR^{12}R^{13})_{0-1}$—;

X is C=O, O, —$CR^{14}R^{15}$— or $NR^{14}$;

$R^{10}$, $R^{11}$, $R^{12}$, $R^{13}$, $R^{14}$ and $R^{15}$ are each independently selected from hydrogen, hydroxy, $C_{1-6}$alkyl, $C_{2-6}$alkenyl, $C_{1-6}$alkoxy, $C(O)C_{1-6}$alkyl, $(CH_2)_{0-3}$aryl, $(CH_2)_{0-3}$heteroaryl, $(CH_2)_{0-3}$Het, $(CH_2)_{0-3}NR^{16}R^{17}$, $C(O)(CH_2)_{0-3}NR^{16}R^{17}$, $NHC(O)(CH_2)_{0-3}NR^{16}R^{17}$, $O(CH_2)_{1-3}NR^{16}R^{17}$, $S(O)_{0-2}(CH_2)_{0-3}R^{16}R^{17}$ and $C(O)(CH_2)_{0-3}OR^{16}$;

or $R^{14}$ is linked to $R^{22}$ or $R^{23}$ to form a ring of 4 to 10 atoms, where said ring is optionally substituted by halogen, hydrogen, $C_{1-4}$alkyl or $C_{1-4}$alkoxy;

Het is a heteroaliphatic ring of 4 to 7 ring atoms, which ring may contain 1, 2 or 3 heteroatoms selected from N, O or S or a group S(O), $S(O)_2$, NH or $NC_{1-4}$alkyl;

$R^{16}$ and $R^{17}$ are independently selected from hydrogen, $C_{1-6}$alkyl and $(CH_2)_{0-4}NR^{18}R^{19}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

$R^{18}$ and $R^{19}$ are independently selected from hydrogen and $C_{1-6}$alkyl; or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

$R^1$ is hydrogen or $C_{1-6}$alkyl;

B is —$CR^{20}R^{21}$—, —C(=O)—, —SO— or —$SO_2$—;

$R^{20}$ and $R^{21}$ are independently selected from hydrogen and $C_{1-6}$alkyl;

or $R^{20}$ and $R^{21}$, together with the carbon atom to which they are joined, form a $C_{3-6}$cycloalkyl group;

M is $C_{4-8}$alkylene or $C_{4-8}$alkenylene, optionally substituted by $R^{22a}$, where 1, 2 or 3 of the carbon atoms in the $C_{4-8}$alkylene or $C_{4-8}$alkenylene groups is optionally replaced by O, $NR^{23a}$, S, SO, $SO_2$, aryl, heteroaryl or Het, where $R^{23a}$ is hydrogen or $C_{1-6}$alkyl, or $R^{23a}$ is linked to $R^{14}$ to form a ring of 4 to 10 atoms as hereinbefore described;

where $R^{22a}$ is halo, $C_{1-4}$alkyl, $(CH_2)_{0-3}C_{3-8}$cycloalkyl, $(CH_2)_{0-3}$ aryl, heteroaryl, Het or oxo, or $R^{22a}$ is linked to $R^{14}$ to form a ring of 4 to 10 atoms as hereinbefore described;

and pharmaceutically acceptable salts thereof.

In a further embodiment of a compound of the formula (Ibo), X is C=O or $CR^{14}R^{15}$, where $R^{14}$ and $R^{15}$ are as hereinbefore defined. Preferably, X is C=O or —$CH_2$—.

In one embodiment of the present invention, Ar is a five- or six-membered aromatic ring optionally containing 1, 2 or 3 heteroatoms independently selected from N, O and S, and which ring is optionally substituted by groups $Q^1$ and $Q^2$ as hereinbefore defined.

Preferably, Ar is a five- or six-membered aromatic ring optionally containing 1 or 2 heteroatoms independently selected from N, O or S, such as phenyl, pyridyl, pyridazinyl, pyrimidinyl, pyrazinyl, furanyl, pyrazolyl, imidazolyl and thienyl, which ring is optionally substituted by groups $Q^1$ and $Q^2$ as hereinbefore defined. More preferably, Ar is phenyl, 2-pyridyl, 3-pyridyl, 4-pyridyl, 2-furanyl or 3-furanyl, particularly phenyl, optionally substituted by groups $Q^1$ and $Q^2$ as hereinbefore defined.

Preferably, $Q^1$ is halogen, hydroxy, $C_{1-6}$alkyl, $C_{1-6}$alkoxy or $O(CH_2)_{0-3}$heteroaryl. More preferably, $Q^1$ is halogen, hydroxy, $C_{1-4}$alkyl or $C_{1-4}$alkoxy. Most preferably, $Q^1$ is fluorine, chlorine, methyl or methoxy. Especially, $Q^1$ is methoxy. Suitable examples of $Q^1$ groups are O—$CH_2$-(2-pyridyl), methoxy and fluorine.

When $Q^1$ is present and Ar is phenyl, preferably, $Q^1$ is at the para-position to the indolyl group.

Preferably, $Q^2$ is absent.

In a further embodiment, A is $C_{3-6}$alkyl, $C_{2-6}$alkenyl or $C_{3-8}$cycloalkyl, where A is optionally substituted by halogen, hydroxy, $C_{1-4}$alkyl or $C_{1-4}$alkoxy. Preferably, A is $C_{3-8}$cycloalkyl, more preferably cyclopentyl or cyclohexyl, most preferably cyclohexyl, optionally substituted by halogen, hydroxy, $C_{1-4}$alkyl or $C_{1-4}$alkoxy.

Preferably, A is unsubstituted or substituted by fluorine, chlorine, methyl or methoxy, particularly fluorine. More preferably, A is unsubstituted or substituted by fluorine. Examples of suitable A groups include cyclohexyl and fluorocyclohexyl, especially 2-fluorocyclohexyl.

In a further embodiment, D is $CR^g$ where $R^g$ is as hereinbefore defined. Preferably, $R^g$ is hydrogen or $C_{1-4}$alkyl. More preferably, $R^g$ is hydrogen.

In a further embodiment, W is a bond, C=O or —$(CR^{10}R^{11})$—$(CR^{12}R^{13})_{0-1}$— where $R^{10}$, $R^{11}$, $R^{12}$ and $R^{13}$ are as hereinbefore defined. Preferably, W is —$(CR^{10}R^{11})$—

$(CR^{12}R^{13})_{0-1}$—. More preferably, W is —CH$_2$— or —CH$_2$CH$_2$—. Most preferably, W is —CH$_2$—.

In a further embodiment, R$^1$ is hydrogen or methyl. Preferably, R$^1$ is hydrogen.

In a further embodiment, B is —CH$_2$— or —SO$_2$—. Preferably, B is —SO$_2$—.

In a further embodiment, M is C$_{4-8}$alkylene, optionally substituted by halo, C$_{1-4}$alkyl or oxo, where 1 or 2 of the carbon atoms in the C$_{4-8}$alkylene group is optionally replaced by O, NR$^{23}$, S, SO or SO$_2$, where R$^{23}$ is as hereinbefore defined. Preferably, M is C$_{5-8}$alkylene, optionally substituted by C$_{1-4}$alkyl or oxo, where 1 or 2 of the carbon atoms in the C$_{5-8}$alkylene group is replaced by O, NH or N(C$_{1-4}$alkyl). Examples of suitable M groups include

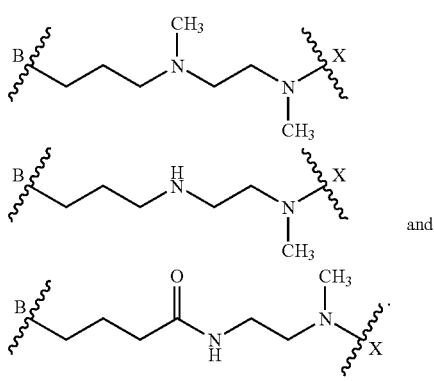

and

Further examples of suitable M groups are:

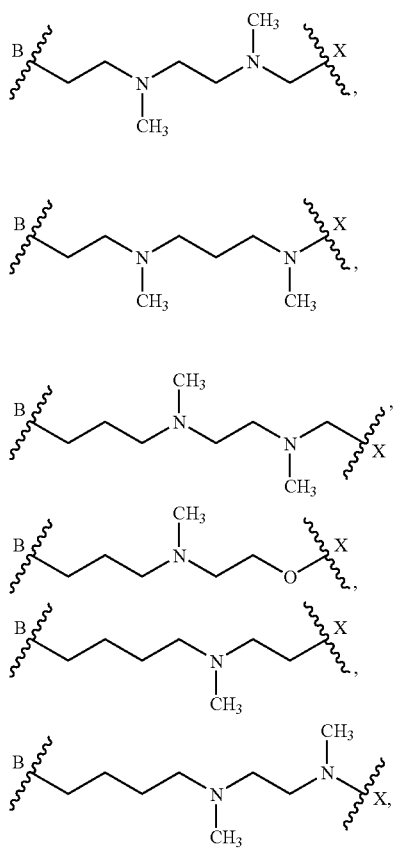

In one embodiment of the present invention, there is provided the compound of formula (Ic):

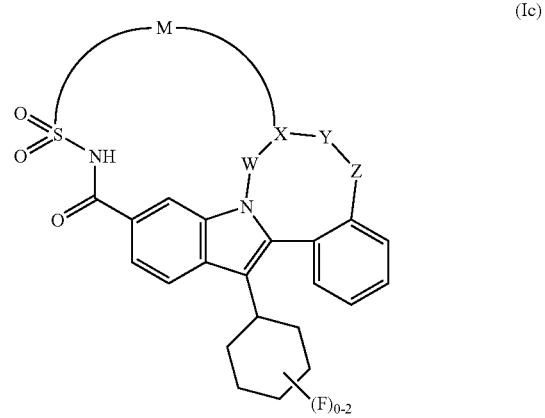

or a pharmaceutically acceptable salt thereof, wherein W, X, Y, Z and M are as defined in relation to formula (I).

In another embodiment of the present invention, there is provided the compound of formula (Id):

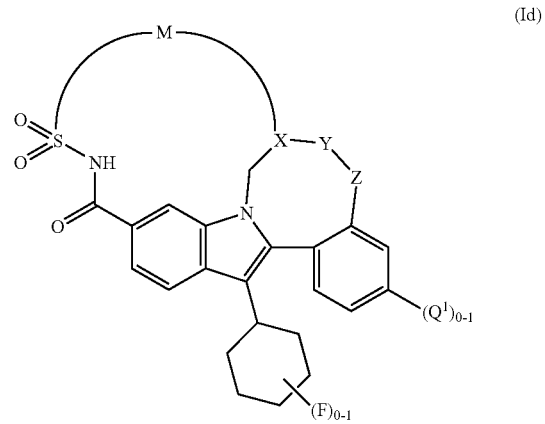

or a pharmaceutically acceptable salt thereof, wherein X, Y, Z, M and Q$^1$ are as defined in relation to formula (I).

In another embodiment of the present invention, there is provided the compound of formula (Ie):

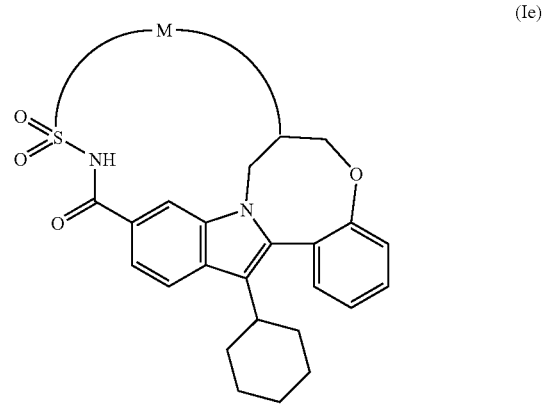

or a pharmaceutically acceptable salt thereof, wherein M is as defined in relation to formula (I).

In another embodiment of the present invention, there is provided the compound of formula (If):

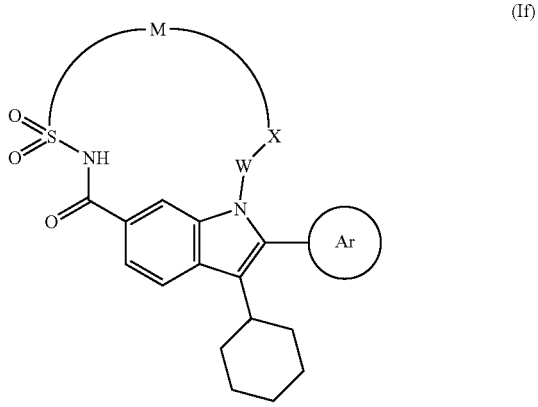

(If)

or a pharmaceutically acceptable salt thereof, wherein Ar, W, X and M are as defined in relation to formula (I).

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl.

As used herein, the term "alkenyl" and "alkynyl" as a group or part of a group means that the group is straight or branched. Examples of suitable alkenyl groups include vinyl and allyl. A suitable alkynyl group is propargyl.

As used herein, the term "alkylene" means that the alkyl group links two separate groups and may be straight or branched. Examples of suitable alkylene groups include ethylene [—CH$_2$—CH$_2$—] and propylene [—CH$_2$—CH$_2$—CH$_2$—, —CH(CH$_3$)—CH$_2$— or —CH$_2$—CH(CH$_3$)—]. The terms "alkenylene" and "alkynylene" shall be construed in an analogous manner.

When used herein, the term "halogen" means fluorine, chlorine, bromine and iodine.

When used herein, the term "aryl" as a group or part of a group means a carbocyclic aromatic ring. Examples of suitable aryl groups include phenyl and naphthyl.

When used herein, the term "heteroaryl" as a group or part of a group means a 5- to 10-membered heteroaromatic ring system containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl, benzofuryl, quinolinyl and isoquinolinyl.

Where a compound or group is described as "optionally substituted" one or more substituents may be present. Furthermore, optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include:

(7R)-14-cyclo hexyl-25-methyl-7,8-dihydro -6H-7,11-(epiminoethanoiminobutanothioiminomethano)indolo[1,2-e][1,5]benzoxazocine-15,21-dione 17,17-dioxide;

(7R)-14-cyclo hexyl-24-methyl-7,8-dihydro -6H-7,11-(epiminoethanoiminopropanothioiminomethano)indolo[1,2-e][1,5]benzoxazocin-15-one 17,17-dioxide;

(7R)-14-cyclo hexyl-21,24-dimethyl-7,8-dihydro -6H-7,11-(epiminoethanoiminopropanothioiminomethano)indolo[1,2-e][1,5]benzoxazocin-15-one 17,17-dioxide;

(7R)-14-[(1R,2S) or (1S,2R)-2-fluorocyclohexyl]-21,24-dimethyl-7,8-dihydro-6H-7,11-(epiminoethanoiminopropanothioiminomethano)indolo[1,2-e][1,5]benzoxazocin-15-one 17,17-dioxide;

7 (R,S)-14-cyclohexyl-22-methyl-7,8-dihydro-6H-7,11-(ethanoiminobutanothioiminomethano)indolo[1,2-e][1,5]benzoxazocin-15-one 17,17-dioxide;

(7R)-14-cyclohexyl-20,24-dimethyl-7,8-dihydro-6H-7,11-(epiminopropanoiminoethanothioiminomethano)indolo[1,2-e][1,5]benzoxazocin-15-one 17,17-dioxide;

13-cyclohexyl-19,22-dimethyl-6,7-dihydro-10,6-(methanoiminothioethanoiminoethanoiminomethano)indolo[1,2-d][1,4]benzoxazepin-14-one 16,16-dioxide;

(7R)-14-cyclo hexyl-22,25-dimethyl-7,8-dihydro -6H-7,11-(epiminoethanoiminobutanothioiminomethano)indolo[1,2-e][1,5]benzoxazocin-15-one 17,17-dioxide;

(7S)-14-cyclohexyl-21-methyl-7,8-dihydro-6H-7,11-(epoxyethanoiminopropanothioiminomethano)indolo[1,2-e][1,5]benzoxazocin-15-one 17,17-dioxide;

13-cyclohexyl-5,20,23-trimethyl-6,7-dihydro-5H-10,6-(methanoiminothiopropanoiminoethanoiminomethano)indolo[1,2-d][1,4]benzodiazepin-14-one 16,16-dioxide;

13-cyclohexyl-20,23-dimethyl-6,7-dihydro-5H-6,10-(epiminoethanoiminopropanothioiminomethano)indolo[2,1-a][2]benzazepin-14-one 16,16-dioxide;

8-cyclohexyl-19,22-dimethyl-1,12b-dihydro-5,1a-(methanoiminothiopropanoiminoethanoiminomethano)cyclopropa[c]indolo[2,1-a][2]benzazepin-13-one 15,15-dioxide;

13-cyclohexyl-20,23-dimethyl-6,7-dihydro-5H-10,6-(methanoiminothiopropanoiminoethanoiminomethano)indolo[2,1-a][2]benzazepin-14-one 16,16-dioxide;

16-cyclohexyl-3,6-dimethyl-17-phenyl-4,5,6,7,8,9-hexahydro-1H-13,15-(ethanediylidene)pyrrolo[2,1-f][1,2,7,10,13]thiatetraazacyclohexadecine-2,12(3H)-dione 10,10-dioxide;

16-cyclohexyl-17-(4-methoxyphenyl)-3,6-dimethyl-2,3,4,5,6,7,8,9-octahydro-1H-13,15-(ethanediylidene)pyrrolo[2,1-f][1,2,7,10,13]thiatetra-azacyclohexadecin-12-one 10,10-dioxide;

16-cyclohexyl-3,6-dimethyl-17-(2-thienyl)-2,3,4,5,6,7,8,9-octahydro-1H-13,15-(ethanediylidene)pyrrolo[2,1-f][1,2,7,10,13]thiatetraazacyclohexadecin-12-one 10,10-dioxide;

(7R)-14-cyclohexyl-3-fluoro-21,24-dimethyl-7,8-dihydro-6H-7,11-(epiminoethanoiminopropanothioiminomethano)indolo[1,2-e][1,5]benzoxazocin-15-one 17,17-dioxide;

(7R)-14-cyclohexyl-2-fluoro-21,24-dimethyl-7,8-dihydro-6H-7,11-(epiminoethanoiminopropanothioiminomethano)indolo[1,2-e][1,5]benzoxazocin-15-one 17,17-dioxide;

16-cyclohexyl-3,6-dimethyl-17-phenyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide;

17-chloro-16-cyclohexyl-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide;

16-cyclohexyl-17-(3-furyl)-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide;

16-cyclohexyl-17-(2-methoxyphenyl)-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide;

17-cyclohexyl-3,6-dimethyl-18-phenyl-3,4,5,6,7,8,9,10-octahydro-14,16-(ethanediylidene)pyrrolo[2,14][1,2,7,10,13]thiatetraazacycloheptadecine-2,13-dione 11,11-dioxide;

and pharmaceutically acceptable salts thereof.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope any enantiomers, diastereomers, geometric isomers and tautomers of the compounds of formula (I). It is to be understood that all such isomers and mixtures thereof are encompassed within the scope of the invention.

The present invention further provides a compound of formula (I) or a pharmaceutically acceptable salt thereof for use in therapy.

The present invention also provides a compound of formula (I) or a pharmaceutically acceptable salt thereof for treatment or prevention of infection by hepatitis C virus in a human or animal.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

In a further aspect, the invention provides a method of inhibiting hepatitis C virus polymerase and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 1 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

The present invention also provides a process for the preparation of compounds of formula (I).

According to a general process (a), compounds of formula (I) may be prepared by internal ring closure of the compound of formula (II):

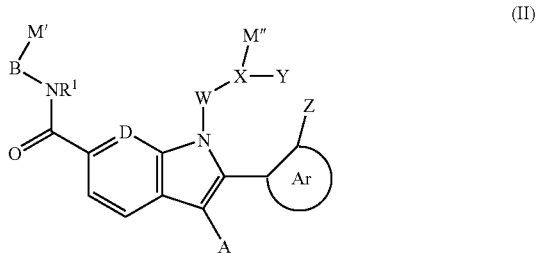

(II)

where A, Ar, B, D, $R^1$, W, X, Y and Z are as defined in relation to formula (I), and M' and M" have suitable precursor functionality to form group M as defined in relation to formula (I). For instance, when M is —$CH_2$—$CH_2$—$CH_2$—NH—$CH_2$—$CH_2$—N($CH_3$)—, M' can be —$CH_2$—$CH_2$—$CH_2$Cl and M" can be N($CH_3$)—$CH_2$—$CH_2$—$NH_2$, where the reaction is carried out in the presence of a mild base, such as diisopropylethylamine, in a suitable solvent, such as acetonitrile or DMF, under microwave irradiation or microwave irradiation. Alternatively, when M is —$CH_2$—$CH_2$—$CH_2$—C(=O)—NH—$CH_2$—$CH_2$—N($CH_3$)—, M' can be —$CH_2$—$CH_2$—$CH_2$—$CO_2H$ and M" can be —N($CH_3$)—$CH_2$—$CH_2$—$NH_2$, where the reaction is carried out by amide bond formation in the presence of a coupling reagent, such as HATU, and a base, such as diisopropylethylamine, in a suitable solvent, such as DMF. In another alternative, when M comprises a C—N bond, the terminal functional group of M' can be —CHO and the terminal functional group of M" can be —$NHR^{23}$. The reductive amination is conveniently carried out in the presence of a mild reducing agent, such as sodium cyanoborohydride, in a suitable solvent, such as MeOH. Optionally, an additive, such as acetic acid, may also be used.

According to a general process (b), compounds of formula (I) may be prepared by internal ring closure of the compound of formula (III):

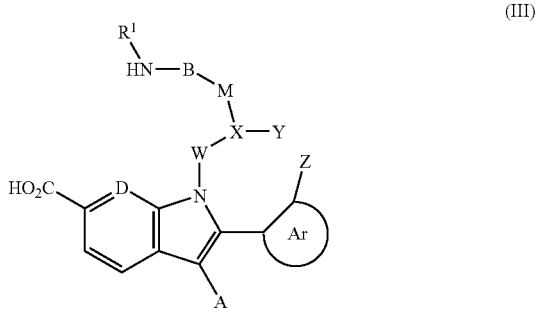

(III)

where A, Ar, B, M, D, $R^1$, W, X, Y and Z are as defined in relation to formula (I). The reaction is conveniently carried out in the presence of a coupling reagent, such as EDC, and an additive, such as DMAP, in a solvent. Suitable solvents included DMF, DCM and mixtures thereof.

Compounds of formulae (II) and (III) are either known in the art or may be prepared by conventional methodology well known to one of ordinary skill in the art using, for instance, procedures described in the accompanying Descriptions and Examples, or by alternative procedures which will be readily apparent.

Compounds of formula (I) can be converted into other compounds of formula (I) using synthetic methodology well known in the art. For instance, the compound of formula (I) where M comprises an N—H group may be converted into the compound of formula (I) where M comprises an N—$CH_3$ group by methylation using formaldehyde followed by a mild reducing agent, such as sodium borohydride. Compounds of the formula (III) may be prepared by arylation of a compound of the formula (IV):

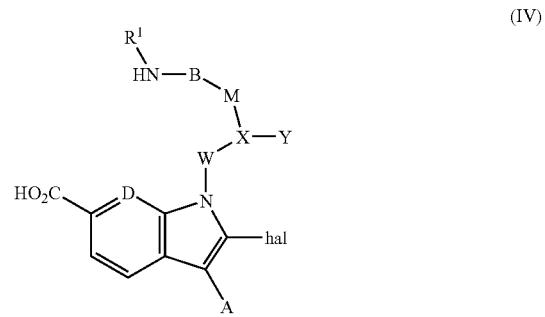

(IV)

where hal is a halogen such as bromine and chlorine; and A, B, D, M, X, Y, W and $R^1$ are as hereinbefore defined. The arylation is a transition-metal catalyst based reaction. Such reactions and the preparation of the halogen precursors can be prepared as generally described in International patent application publications WO2006/046030 and WO2006/046039.

General Synthetic Schemes

Four general strategies were employed for assembly of compounds from the macrocyclic class (Methods A, B, C and D); Method B can be regarded as an extension of Method A.

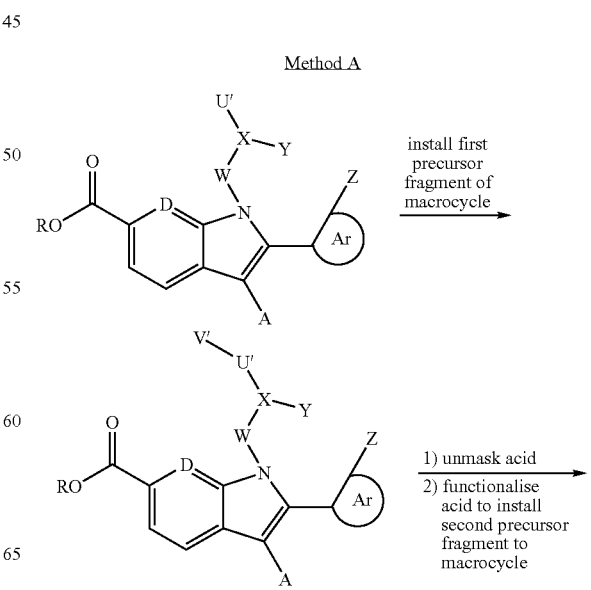

-continued

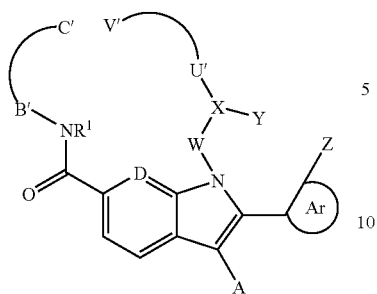

1) Functional group manipulation
2) ring closure

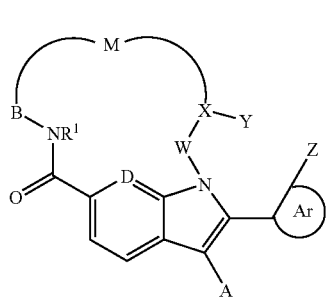

wherein B' is a precursor of B and U'V'C' is a precursor of M.

A suitably functionalised tether was assembled first (as described in International patent application publications WO2006/046030, WO2006/046039 and WO2007/054741). A precursor fragment to one section of the macrocycle was installed on the tether, with subsequent unmasking of the acid at C6 and functionalisation to introduce a precursor fragment to the remaining segment of the macrocycle. Functional group manipulation and macrocyclisation (e.g., via amide bond formation, alkylation, reductive amination, metathesis etc.) set up the macrocycle. Potentially, the bond formed in ring closure could be at almost any point around the macrocyclic linker (e.g., forming the acylsulfonamide bond could also be the ring closing step).

Method B

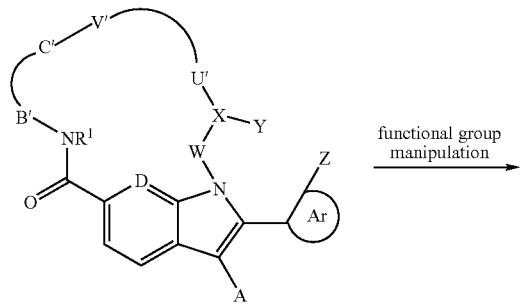

functional group manipulation →

-continued

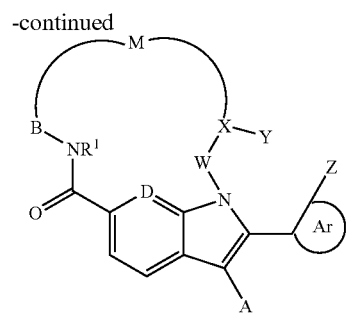

wherein B' is a precursor of B and U'V'C' is a precursor of M.

Functional groups on the macrocycle were manipulated post-closure, e.g., via reductive amination, alkylation, amide reduction, amide formation etc. Potentially, sidechains can branch from any point around the macrocyclic linker Method C

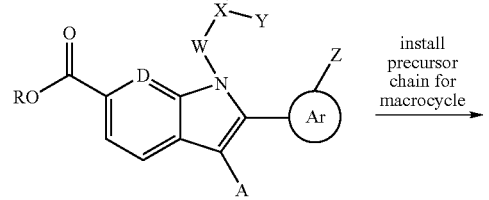

install precursor chain for macrocycle →

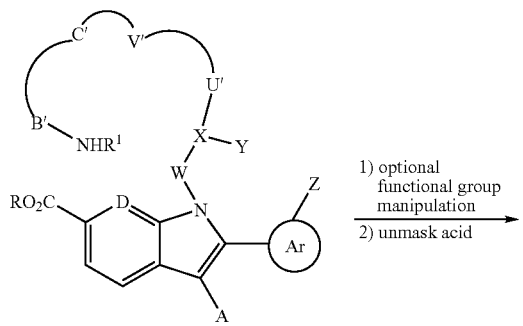

1) optional functional group manipulation
2) unmask acid →

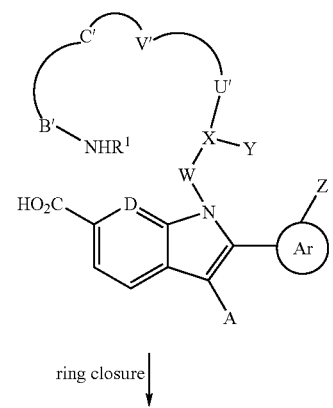

ring closure ↓

-continued

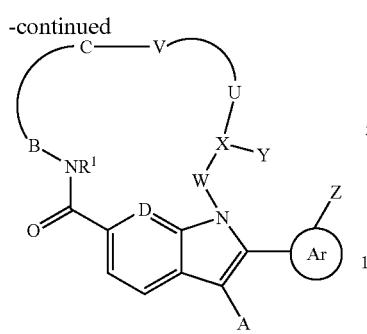

wherein B' is a precursor of B and U'V'C' is a precursor of M.

A suitably functionalised tether was assembled first (as described in International patent application publications WO 2006/046030, WO 2006/046039 and WO 2007/054741). A precursor fragment to the macrocycle was installed on the tether (either step-wise or as a single transformation). Optionally, functionality on this precursor to the macrocycle could be modified prior to unmasking of the acid at C6 of the indole and macrocyclisation (e.g., via amide bond formation) to set up the macrocycle.

Method D

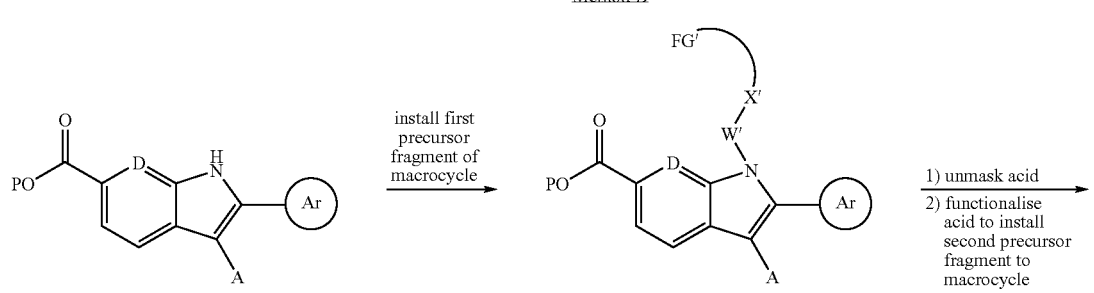

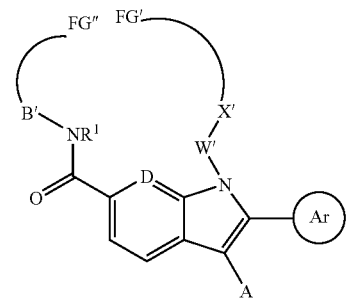

1) Functional group manipulation
2) ring closure

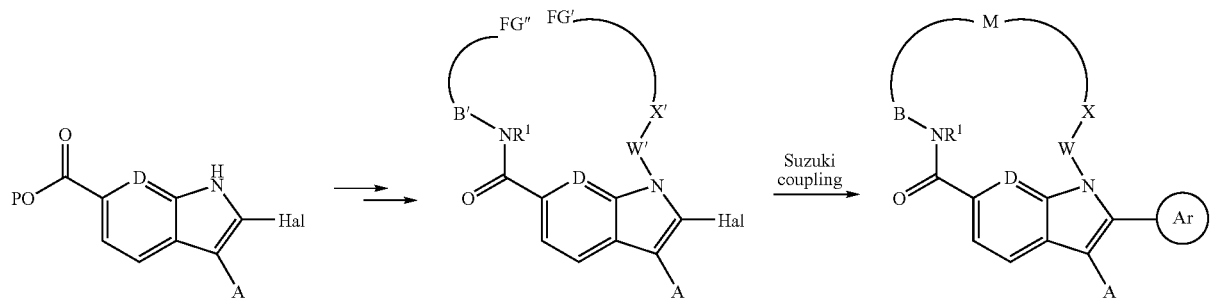

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

Compounds of the formula (V) are important intermediates and form a further aspect of the present invention:

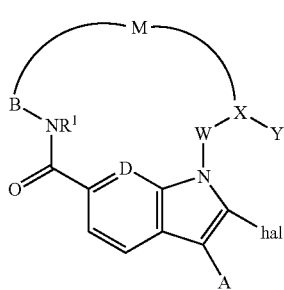

(V)

where hal is chloro or bromo.

The present invention is illustrated further by the following non-limiting examples.

The compounds of the invention were tested for inhibitory activity against the HCV RNA dependent RNA polymerase (NS5B) in an enzyme inhibition assay (example i)) and in a cell based sub-genomic replication assay (example ii)). The compounds generally have $IC_{50}$'s below 1 μM in the enzyme assay and several examples have $EC_{50}$'s below 2 μM in the cell based assay.

Compound names in the examples were generated using software from ACDLabs (version 8.0).

i) In-Vitro HCV NS5B Enzyme Inhibition Assay

International patent application publication WO 96/37619 describes the production of recombinant HCV RdRp from insect cells infected with recombinant baculovirus encoding the enzyme. The purified enzyme was shown to possess in vitro RNA polymerase activity using RNA as template. The reference describes a polymerisation assay using poly(A) and oligo(U) as a primer or an heteropolymeric template. Incorporation of tritiated UTP or NTPs is quantified by measuring acid-insoluble radioactivity. The present inventors have employed this assay to screen the various compounds described above as inhibitors of HCV RdRp.

Incorporation of radioactive UMP was measured as follows. The standard reaction (50 μl) was carried out in a buffer containing 20 mM tris/HCl pH 7.5, 5 mM $MgCl_2$, 1 mM DTT, 50 mM NaCl, 0.03% N-octylglucoside, 1 μCi [$^3$H]-UTP (40 Ci/mmol, NEN), 10 μM UTP and 10 μs/ml poly(A) or 5 μM NTPs and 5 μg/ml heteropolymeric template. Oligo(U)$_{12}$ (1 μg/ml, Genset) was added as a primer in the assay working on Poly(A) template. The final NS5B enzyme concentration was 5 nM. The order of assembly was: 1) compound, 2) enzyme, 3) template/primer, 4) NTP. After 1 h incubation at 22° C. the reaction was stopped by adding 50 μl of 20% TCA and applying samples to DE81 filters. The filters were washed thoroughly with 5% TCA containing 1 M $Na_2HPO_4$/$NaH_2PO_4$, pH 7.0, rinsed with water and then ethanol, air dried, and the filter-bound radioactivity was measured in the scintillation counter. Carrying out this reaction in the presence of various concentrations of each compound set out above allowed determination of $IC_{50}$ values by utilising the formula:

$$\% \text{ Residual activity} = 100/(1+[I]/IC_{50})^s$$

where [I] is the inhibitor concentration and "s" is the slope of the inhibition curve.

ii) Cell Based HCV Replication Assay

Cell clones that stably maintain subgenomic HCV replicon were obtained by transfecting Huh-7 cells with an RNA replicon identical to $I_{377}$neo/NS3-3'/wt described by Lohmann et al. (1999)(EMBL-genbank No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in International patent application publication WO 02/59321). Cells were seeded into 96 well plates at a density of $10^4$ cells per well in a final volume of 0.1 ml of DMEM/10% FCS. Two hours after plating, 50 μl of DMEM/10% FCS containing a 3×concentration of inhibitor were added, cells were incubated for 96 hours and then fixed for 10 minutes with ice-cold isopropanol. Each condition was tested in duplicate and average absorbance values were used for calculations. The cells were washed twice with PBS, blocked with 5% non-fat dry milk in PBS +0.1% TritonX100 +0.02% SDS (PBSTS) and then incubated o/n at 4°C. with the 10E5/24 mab diluted in Milk/PBSTS. After washing 5 times with PBSTS, the cells were incubated for 3 hours at room temperature with Fc specific anti-mouse IgG conjugated to alkaline phosphatase (Sigma), diluted in Milk/PBSTS. After washing again as above, the reaction was developed with p-Nitrophenyl phosphate disodium substrate (Sigma) and the absorbance at 405/620 nm read at intervals. For calculations, we used data sets where samples incubated without inhibitors had absorbance values comprised between 1 and 1.5. The inhibitor concentration that reduced by 50% the expression of NS3 ($IC_{50}$) was calculated by fitting the data to the Hill equation, $$\text{Fraction inhibition} = 1-(A_i-b)/(A_0-b)=[I]^n/([I]^n+IC_{50})$$

where:
Ai =absorbance value of HBI10 cells supplemented with the indicated inhibitor concentration.
$A_0$ =absorbance value of HBI10 cells incubated without inhibitor.
b=absorbance value of Huh-7 cells plated at the same density in the same microtiter plates and incubated without inhibitor.
n=Hill coefficient.

iii) General Procedures

All solvents were obtained from commercial sources (Fluka, puriss.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W.C. Still et al., J. Org. Chem. 1978, 43, 2923) or on commercial flash chromatography systems (Biotage corporation and Jones Flashmaster II) utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H NMR spectra were recorded on BRUKER AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in hertz (Hz); number of protons. Mass spectral (MS) data were obtained on a PERKIN ELMER API 100, or WATERS MICROMASS ZQ, operating in negative (ES$^-$) or positive (ES$^+$) ionization mode and results are reported as the ratio of mass over charge (m/z) for the parent ion only. Preparative scale HPLC separations were carried out on a WATERS DELTA PREP 4000 separation module, equipped with a WATERS 486 absorption detector or on an automated WATERS FRACTION LYNX or GILSON preparative system. In all cases compounds were eluted with linear gradients of water and MeCN both containing 0.1% TFA using flow rates between 15 and 40 mL/min.

The following abbreviations are used in the examples, the schemes and the tables: Ac: acetyl; aq.: aqueous; Ar: aryl; atm: atmosphere; 9-BBN: 9-borabicyclo[3.3.1]nonane; cat.: catalytic; dioxan(e): 1,4-dioxane; dppf: (1,1'-bisdiphenylphosphino)ferrocene; DAST: diethylaminosulfur trifluoride; 1,2-DCE: 1,2-dichloroethane; DCM: dichloromethane; DIAD: diisopropylazodicarboxylate; DIC: 1,3-diisopropyl carbodiimide; DIPEA: diisopropylethyl amine; DMAP: N,N-dimethylpyridin-4-amine; DME: dimethoxyethane; DMF: dimethylformamide; DMS: dimethylsulfide; DMSO: dimethylsulfoxide; DMP: Dess-Martin Periodinane; DPPA: diphenylphosphorylazide; EDC: 1-ethyl-(3-dimethylaminopropyl)carbodiimide HCl salt; eq.: equivalent(s); Et$_3$N: triethylamine; EtOAc: ethyl acetate; Et$_2$O: diethyl ether; EtOH: ethanol; Et$_3$SiH: triethylsilane; FC: Flash Chromatography; h: hour(s); HOAc: acetic acid; HATU: O-(7-azabenzotriazol-1-yl)-N,N,N',N'-tetramethyluronium hexafluorophosphate; HOBt: hydroxybenzotriazole; Me: methyl; MeCN: acetonitrile; MeOH: methanol; min: minute(s); MS: mass spectrum; NBS: N-bromo succinimide; PE: petroleum ether; Ph: phenyl; quant.: quantitative; RP-HPLC: reversed phase high-pressure liquid chromatography; RT: room temperature; sat.: saturated; sec: second(s); SFC: Super-critical fluid chromatography; sat. aq.: saturated solution; TBAF: tetrabutyl ammonium fluoride; TBTU: O-benzotriazol-1-yl-N,N,N',N'-tetramethyluronium tetrafluoroborate; TFA: trifluoroacetic acid; THF: tetrahydrofuran; THP: tetrahydropyranyl; TMS: trimethylsilyl; Ts: para-toluene sulfonyl.

EXAMPLE 1

(7R)-14-cyclohexyl-25-methyl-7,8-dihydro-6H-7,11-(epiminoethanoiminobutanothioiminomethano)indolo[1,2-e][1,5]benzoxazocine-15,21-dione 17,17-dioxide Step 1: benzyl 4-(aminosulfonyl)butanoate Cs$_2$CO$_3$ (0.51 eq) was added to a solution of 4-(aminosulfonyl)butanoic acid (1 M) in DMF. After 1 h, benzyl bromide (1 eq) was introduced and the reaction left to stir overnight before diluting with DCM and filtering. The filtered liquor was concentrated in vacuo, the residue taken up in DCM and washed with saturated aqueous NaHCO$_3$, water and brine, before being dried over Na$_2$SO$_4$, filtered and concentrated in vacuo. Trituration of the residue with Et$_2$O afforded the title compound as a white solid (27%). (ES$^+$) m/z 280 (M+Na)$^+$ Step 2: tert-butyl (2R)-2-({[(4-nitrophenyl)sulfonyl]oxy}methyl)aziridine-1-carboxylate A solution of tert-butyl (2R)-2-({[tert-butyl(dimethyl)silyl]oxy}methyl)aziridine-1-carboxylate (prepared following literature procedures: Travins, J. M.; Etzkorn, F. A. *Tetrahedron Lett.* 1998, 39, 9389-9392) in THF/Et$_2$O (1/1) (0.17 M) was cooled in an ice bath and treated dropwise over 20 min with 1 M TBAF in THF (1.05 eq). The resulting solution was stirred in the ice bath for 30 min, before being quenched by the addition of sat. aq. NaHCO$_3$ and extracted into Et$_2$O/PE (4/1). The organic layers were collected, washed with brine, dried over Na$_2$SO$_4$, filtered and concentrated in vacuo. The residue was taken up in dry DCM (0.17 M) and TEA (1.3 eq) introduced prior to cooling to 0° C. DMAP (0.1 eq) and 4-nitrobenzenesulfonyl chloride (1.1 eq) were added and the resulting mixture left to stir at RT overnight. The reaction mixture was diluted with DCM and washed with sat. aq. NaHCO$_3$, water and brine before drying over Na$_2$SO$_4$, filtering and concentrating in vacuo. The crude was purified by FC (PE/EtOAc 80:20) to afford the title compound as an off-white solid (57%). (ES$^+$) m/z 359 (M+H)$^+$ Step 3: methyl(7R)-7-[(tert-butoxycarbonyl)amino]-14-cyclohexyl-7,8-dihydro-6H-indolo[1,2-e][1,5]benzoxazocine-11-carboxylate A solution of methyl 3-cyclohexyl-2-(2-hydroxyphenyl)-1H-indole-6-carboxylate (prepared as described in International patent application publication WO2006/046030)(0.15 M) in DMF was treated with CsF (4 eq) in one portion; the resulting mixture was stirred for 20 min at RT then treated via dropping funnel over 30 min with a solution of tert-butyl (2R)-2-({[(4-nitrophenyl)sulfonyl]oxy}methyl)aziridine-1-carboxylate (1.3 eq) in DMF (0.5 M). The resulting solution was stirred at RT overnight. The reaction mixture was then placed into an ice bath and powdered KO$^t$Bu (1.4 eq) added slowly to the reaction mixture. After 1.5 h, the reaction was quenched with sat. aq. NH$_4$Cl and extracted into EtOAc. The combined organic layers were washed with water and brine, before being dried over Na$_2$SO$_4$, filtered and concentrated in vacuo. The crude material was purified by FC (PE/EtOAc 80:20) affording the product as an off-white foam (85%). (ES$^+$) m/z 505 (M+H)$^+$ Step 4: methyl(7R)-7-amino-14-cyclohexyl-7,8-dihydro-6H-indolo[1,2-e][1,5]benzoxazocine-11-carboxylate Methyl (7R)-7-[(tert-butoxycarbonyl)amino]-14-cyclohexyl-7,8-dihydro-6H-indolo[1,2-e][1,5]benzoxazocine-11-carboxylate (0.14 M) in DCM was treated with TFA (10 eq) and stirred at RT for 1 h. The reaction was diluted with DCM and cautiously basified with aq. NaHCO$_3$, before separating the phases and extracting the aqueous with DCM. The combined organics were washed with brine, dried over Na$_2$SO$_4$, filtered and concentrated in vacuo to afford the product as an off-white foam (100%) that was used without further purification. (ES$^+$) m/z 405 (M+H)$^+$; [α]$_D$, +42.3, c=1, MeOH Step 5: methyl(7R)-14-cyclohexyl-7-(methylamino)-7,8-dihydro-6H-indolo[1,2-e][1,5]benzoxazocine-11-carboxylate A solution of methyl(7R)-7-amino-14-cyclohexyl-7,8-dihydro-6H-indolo[1,2-e][1,5]benzoxazocine-11-carboxylate (0.35 M) in THF was treated dropwise with 2,2,2-trifluoroethyl formate (1.2 eq) and stirred overnight at RT. The volatiles were removed in vacuo and the residue dissolved (0.11 M) in THF and treated dropwise with $BH_3.DMS$ complex (2 M in THF; 5 eq). The resulting solution was stirred at RT for 20 h. The reaction was quenched by the careful addition of HCl/MeOH (1.25 M) and the resulting solution refluxed for 2 h. The volatiles were then removed in vacuo and the residue partitioned between sat. aq. $NaHCO_3$ and EtOAc. The combined organics were washed with brine, dried over $Na_2SO_4$, filtered and concentrated in vacuo. The crude was purified by FC (EtOAc/PE 80:20+1% $NEt_3$) to afford the product (79%). ($ES^+$) m/z 419 $(M+H)^+$; $[\alpha]_D$ +47.4, c=0.46, $CHCl_3$ Step 6: methyl(7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylate To a solution of tert-butyl (2-oxoethyl)carbamate (1 eq; 0.38 M) in dry MeOH was added a mixture of methyl (7R)-14-cyclohexyl-7-(methylamino)-7,8-dihydro-6H-indolo[1,2-e][1,5]benzoxazocine-11-carboxylate(0.14 M), acetic acid (2 eq) and sodium acetate (1 eq) in dry MeOH, and the mixture stirred at RT for 15 min. Then Pd/C (0.3 weight eq) was added as a slurry in MeOH under $N_2$. The atmosphere in the reaction vessel was charged with $H_2$, and the reaction stirred vigorously under a $H_2$ atmosphere (balloon) at 60° C. overnight. The reaction was allowed to cool to RT, flushed with $N_2$ and filtered through a plug of CELITE. The filtrate was concentrated in vacuo and the residue purified by FC (PE/EtOAc 2.5:1 to 1.5:1 gradient) to afford the title compound (82%). ($ES^+$) m/z 562 $(M+H)^+$; $[\alpha]_D$ +67.1, c=0.67, $CHCl_3$ Step 7(7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylic acid Lithium hydroxide monohydrate (4.4 eq) was added to a solution of methyl(7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylate (0.02 M) in MeOH/THF/$H_2O$ (1/1/1). The reaction was heated at 60° C. for 4h prior to introducing further lithium hydroxide monohydrate (5 eq) and continuing heating for 2 h. The reaction was allowed to cool to RT, and the solvent volume reduced in vacuo. The residue was partitioned between 1N HCl(aq) and EtOAc, extracting the aqueous fraction a further two times with EtOAc. The combined organics were washed with brine, dried over $Na_2SO_4$, filtered and concentrated in vacuo to afford the product as an off white foam (98%). ($ES^+$) m/z 548 $(M+H)^+$ Step 8: benzyl 4-{[({(7R)-7-[{2-[(tert-butoxycarbonyl)amino]ethyl}(methyl)amino]-14-cyclohexyl-7,8-dihydro-6H-indolo[1,2-e][1,5]benzoxazocin-11-yl}carbonyl)amino]sulfonyl}butanoate Benzyl 4-(aminosulfonyl)butanoate (1.3 eq)(prepared as described in step 1), DMAP (2.5 eq) and EDC (1.5 eq), were added to a solution of (7R)-7-[{2-[(tert -butoxycarbonyl)amino]ethyl}(methyl)amino]-14-cyclohexyl-7,8-dihydro-6H-indolo[1,2-e][1,5]benzoxazocine-11-carboxylic acid (0.03 M) in DCM. The reaction was stirred under $N_2$ at RT for 24h, before volatiles were removed in vacuo to leave the crude product as a yellow gum, which was purified by automated RP-HPLC (WATERS XTERRA column; MeCN/$H_2O$/ 0.1% TFA gradient). Fractions containing the pure compound were combined and lyophilized to afford the product as a white powder (37%). ($ES^+$) m/z 787 $(M+H)^+$ Step 9: {[({(7R)-7-[{2-[(tert-butoxycarbonyl)amino]ethyl}(methyl)amino]-14-cyclohexyl-7,8-dihydro-6H-indolo[1,2-e][1,5]benzoxazocin-11-}carbonyl)amino]sulfonyl}butanoic acid Pd/C (10 wt %) was added as a slurry in MeOH under $N_2$ to a solution of benzyl 4-{[({(7R)-7-[{2-[(tert-butoxycarbonyl)amino]ethyl}(methyl)amino]-14-cyclohexyl-7,8-dihydro-6H-indolo[1,2-e][1,5]benzoxazocin-11-yl}carbonyl)amino]sulfonyl}butanoate (0.003 M) in MeOH. The atmosphere in the reaction vessel was exchanged for $H_2$, and the reaction stirred vigorously at RT for 1 h. The reaction vessel was flushed with $N_2$, and the reaction mixture filtered through a plug of CELITE(washing well with MeOH). Volatiles were removed in vacuo to afford the crude product as a yellow oil. ($ES^+$) m/z 697 $(M+H)^+$ Step 10: 4-{[({(7R)-7-[(2-aminoethyl)(methyl)amino]-14-cyclohexyl-7,8-dihydro-6H-indolo[1,2-e][1,5]benzoxazocin-11-yl}carbonyl)amino]sulfonyl}butanoic acid 4-{[({(7R)-7-[{2-[(tert-butoxycarbonyl)amino]ethyl}(methyl)amino]-14-cyclohexyl-7,8-dihydro-6H-indolo[1,2-e][1,5]benzoxazocin-11-yl}carbonyl)amino]sulfonyl}butanoic acid was dissolved in DCM (0.01 M), and ethereal HCl added (2 M, >100 eq). The reaction was stirred with heating at 40° C. for 1 h. Volatiles were removed in vacuo, and the residue diluted with $Et_2O$ and reconcentrated in vacuo (twice) to drive off excess HCl and afford the crude product as the bis hydrochloride salt. ($ES^+$) m/z 597 $(M+H)^+$ Step 11: (7R)-14-cyclohexyl-25-methyl-7,8-dihydro-6H-7,11-(epiminoethanoiminobutan-othioiminomethano)indolo[1,2-e][1,5]benzoxazocine-15,21-dione 17,17-dioxide DIPEA (6 eq) and HATU (1.2 eq) were introduced to a solution of 4-{[({(7R)-7-[(2-aminoethyl)(methyl)amino]-14-cyclohexyl-7,8-dihydro-6H-indolo[1,2-e][1,5]benzoxazocin-11-yl}carbonyl)amino]sulfonyl}butanoic acid (0.005 M) in DMF, and the reaction stirred under $N_2$ at 45° C. for 1 h. The volatiles were evaporated in vacuo, and the residue purified by automated RP-HPLC (WATERS XTERRA column; MeCN/$H_2O$/0.1% TFA gradient). Fractions containing the pure compound were combined and lyophilized to afford the product as a white powder (30% overall for steps 9, 10, 11). $^1H$ NMR (600 MHz, DMSO-$d_6$ +TFA, 335 K) δ1.14-1.22 (m, 1H), 1.31-1.40 (m, 2H), 1.53-1.57 (m, 1H), 1.68-1.75 (m, 2H), 1.84-1.87 (m, 1H), 1.91-2.07 (m, 5H), 2.10-2.16 (m, 1H), 2.29-2.34 (m, 1H), 2.38-2.45 (m, 1H), 2.71-2.77 (m, 1H), 2.94 (s, 3H), 3.37-3.55 (m, 6H), 3.88-3.95 (m, 1H), 4.26-4.31 (m, 1H), 4.36-4.42 (m, 1H), 4.81-4.86 (m, 1H), 7.28-7.32 (m, 2H), 7.38 (dd, J7.7, 1.5, 1H), 7.47 (d, J8.7, 1H), 7.54-7.57 (m, 1H), 7.92 (d, J8.7, 1H), 8.16 (s, 1H), 8.19 (b s, 1H), 11.57 (b s, 1H); ($ES^+$) m/z 579 $(M+H)^+$

EXAMPLE 2

(7R)-14-cyclohexyl-24-methyl-7,8-dihydro-6H-7,11-(epiminoethanoiminopropanothioiminomethano)indolo[1,2-e][1,5]benzoxazocin-15-one 17,17-dioxide Step 1: 3-chloropropane-1-sulfonamide A 0.5 M solution of ammonia (15 eq) in dioxane was added slowly at RT under nitrogen to a solution of 3-chloropropane sulfonyl chloride in dioxane (0.56 M). The reaction was left to stir for 2 h before removing volatiles in vacuo. The residue was taken up in CHCl₃, filtered to remove ammonium chloride and the filtered liquor concentrated in vacuo to afford the title compound as a colourless oil that solidified on standing. $^1$H NMR (300 MHz, DMSO-$d_6$, 300 K) δ2.09-2.17 (m, 2H), 3.06-3.11 (m, 2H), 3.72-3.77 (m, 2H), 6.87 (s, 2H).

Step 2: tert-butyl{2-[[(7R)-11-({[(3-chloropropyl) sulfonyl]amino}carbonyl)-14-cyclohexyl-7,8-dihydro-6H-indolo[1,2-e][1,5]benzoxazocin-7-yl](methyl)amino]ethyl}carbamate 3-chloropropane-1-sulfonamide (1.8 eq), DMAP (2.9 eq) and EDC (1.8 eq), were added to a solution of (7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylic acid (prepared as described in Example 1, Step 7) (0.025 M) in DCM. The reaction was stirred under N₂ at 40° C. for 2 h, before being allowed to cool. Volatiles were removed in vacuo to leave the crude product as a yellow gum which could be taken on without further purification. (ES⁺) m/z 687 (M+H)⁺; 689 (M+H)⁺

Step 3: (7R)-7-[(2-aminoethyl)(methyl)amino]-N-[(3-chloropropyl)sulfonyl]-14-cyclohexyl-7,8-dihydro-6H-indolo[1,2-e][1,5]benzoxazocine-11-carboxamide tert-Butyl {2- [[(7R)-11-({[(3-chloropropyl)sulfonyl] amino}carbonyl)-14-cyclohexyl-7,8-dihydro-6H-indolo[1,2-e][1,5]benzoxazocin-7-yl](methyl)amino]ethyl} carbamate was dissolved in DCM (0.025 M), and ethereal HCl added (2M,>50 eq). The reaction was stirred with heating at 40° C. for 1 h. Volatiles were removed in vacuo, and the residue diluted with Et₂O and reconcentrated in vacuo (twice) to drive off excess HCl and afford the crude product as the bis hydrochloride salt. Purification was by automated RP-HPLC (WATERS XTERRA column; MeCN/H₂O/0.1% TFA gradient). Fractions containing the pure compound were combined and lyophilized to afford the product as a white powder (37% over steps 2, 3). (ES⁺) m/z 587 (M+H)⁺; 589 (M+H)⁺

Step 4: (7R)-14-cyclohexyl-24-methyl-7,8-dihydro-6H-7,11-(epiminoethanoiminopropanothioiminomethano)indolo[1,2-e][1,5]benzoxazocin-15-one 17,17-dioxide $^i$Pr₂NEt (20 eq) was added to a solution of (7R)-7-[(2-aminoethyl)(methyl)amino]-N-[(3-chloropropyl)sulfonyl]-14-cyclohexyl-7,8-dihydro-6H-indolo [1,2-e][1,5]benzoxazocine-11-carboxamide in MeCN (0.003 M). The reaction was heated in a microwave at 150° C. for 300 sec. The volatiles were removed in vacuo, and the residue was purified by automated RP-HPLC (WATERS XTERRA column; MeCN/H₂O/ 0.1% TFA gradient). Fractions containing the pure compound were combined and lyophilized to afford the product as a white powder (8.5%). $^1$H NMR (400 MHz, DMSO-$d_6$, 300 K) δ 1.10-1.20 (m, 1H), 1.28-1.37 (m, 2H), 1.42-1.47 (m, 1H), 1.65-1.73 (m, 2H), 1.81-2.09 (m, 5H), 2.17-2.28 (m, 1H), 2.31 (s, 3H), 2.62-2.69 (m, 1H), 2.80-2.91 (m, 1H), 3.02-3.18 (m, 3H), 3.44-3.62 (m, 5H), 3.84 (dd, J 14.8, 9.4, 1H), 4.02 (t, J 11.4, 1H), 4.34 (dd, J 11.4, 5.4, 1H), 4.54 (d, J 14.8, 1H), 7.31-7.38 (m, 3H), 7.48 (d, J8.4, 1H), 7.54-7.59 (m, 1H), 7.92 (d, J 8.4, 1H), 8.09 (s, 1H), 8.65 (b s, 1H), 11.85 (b s, 1H); (ES⁺) m/z 551 (M+H)⁺.

EXAMPLE 3

(7R)-14-cyclohexyl-21,24-dimethyl-7,8-dihydro-6H-7,11-(epiminoethanoiminopropanothioiminomethano)indolo[1,2-e][1,5]benzoxazocin-15-one 17,17-dioxide Formaldehyde (37 wt % in water; 15 eq) was added to a solution of (7R)-14-cyclohexyl-24-methyl-7,8-dihydro-6H-7,11-(epiminoethanoiminopropanothioiminomethano) indolo[1,2-e][1,5]benzoxazocin-15-one 17,17-dioxide (prepared as described in Example 2; Step 4) in MeOH (0.004 M). The pH was adjusted to pH 5-6 with HOAc and, after 5 min, NaBH₄ (20 eq) introduced. The reaction was stirred at RT for 15 min before quenching with 1N HCl(aq) and concentrating to dryness in vacuo. The residue was purified by automated RP-HPLC (WATERS XTERRA column; MeCN/H₂O/0.1% TFA gradient). Fractions containing the pure compound were combined and lyophilized to afford the product as a white powder (65%). $^1$H NMR (400 MHz, DMSO-$d_6$, 300 K) δ1.10-1.20 (m, 1H), 1.29-1.38 (m, 2H), 1.42-1.46 (m, 1H), 1.67-1.74 (m, 2H), 1.83-1.94 (m, 4H), 2.12-2.29 (m, 2H), 2.33 (s, 3H), 2.63-2.69 (m, 1H), 2.80 (s, 3H), 2.84-2.95 (m, 1H), 3.08-3.20 (m, 3H), 3.44-3.68 (m, 5H), 3.84 (dd, J 14.9, 9.8, 1H), 4.02 (t, J 11.7, 1H), 4.29 (dd, J 11.7, 5.2, 1H), 4.53 (d, J 14.9, 1H), 7.31-7.39 (m, 3H), 7.49 (d, J8.4, 1H), 7.54-7.59 (m, 1H), 7.93 (d, J8.4, 1H), 8.11 (s, 1H), 11.98 (s, 1H); (ES⁺) m/z 565 (M+H)⁺.

EXAMPLE 4

(7R)-14-[(1R,2S) or (1S,2R)-2-fluorocyclohexyl]-21,24-dimethyl-7,8-dihydro-6H-7,11-(epiminoethanoiminopropanothioiminomethano)indolo[1,2-e][1,5]benzoxazocin-15-one 17,17-dioxide Step 1: methyl 3-cyclohex-1-en-1-yl-1H-indole-6-carboxylate A solution (0.1 M) of 3-cyclohex-1-en-1-yl-1H-indole-6-carboxylic acid (prepared as described in International patent application publication WO2004/087714) in dry DMF was cooled to 0° C. and treated with K₂CO₃ (1.05 eq). A solution (3 M) of MeI (1.05 eq) in DMF was then added over 0.5 h, and the temperature was raised to 20° C. After 18 h, the reaction was quenched with aqueous HCl(1N) and diluted with EtOAc. The organic phase was separated and washed several times with aqueous HCl(1N), then with brine. The dried organics were concentrated to give the title compound (99%) as a solid; (ES⁺) m/z 256 (M+H)⁺.

Step 2: (±)-methyl 3-[(trans)-2-hydroxycyclohexyl]-1H-indole-6-carboxylate

A solution (0.2 M) of the preceding material in dry THF was treated over 1 h at 0° C. with BH₃SMe₂ (2 M in THF, 1.1 eq). The mixture was stirred at 20° C. for 12 h, then cooled to 0° C. and treated sequentially with aqueous NaOH (3 M, 5.7 eq) and H₂O₂ (30% in H₂O₂O (30% in H₂O 8.4 eq). This mixture was stirred at 20° C. for 3 h then diluted with EtOAc and neutralized with sat.aq. NH₄Cl. The organic phase was washed with sat.aq. NaHCO₃ and brine, then dried and concentrated. The residue was washed several times with Et₂O to give the title compound (73%) as a white powder; (ES⁺) m/z 274 (M+H)⁺.

Step 3: (±)-methyl 3-[(trans)-2-fluorocyclohexyl]-1H-indole-6-carboxylate

A solution (0.08 M) of the foregoing material in dry EtOAc was treated with DAST (1.2 eq) over 15 min at −50° C. The mixture was stirred for 1 h then warmed to 20° C. After 3 h the mixture was quenched with sat. aq. NaHCO$_3$ and diluted with EtOAc. The organic phase was washed with brine, dried and concentrated under reduced pressure. The residue was crystallized from hot EtOAc to give the title compound (61%). The filtrate was concentrated and the residue purified by flash chromatography (10% to 30% EtOAc: PE) to give a second crop of the title compound (17%) as a solid; (ES$^+$) m/z 276 (M+H)$^+$.

Step 4: (±)-methyl 2-bromo-3-[(trans)-2-fluorocyclohexyl]-1H-indole-6-carboxylate A solution (0.16 M) of the foregoing material in CH$_2$Cl$_2$ was treated with NBS (1.1 eq) over 2 h. The resulting mixture was stirred for 4h then diluted with aqueous Na$_2$S$_2$O$_3$ (1N) and stirred for 12 h. The organic phase was separated and washed with aqueous Na$_2$S$_2$O$_3$ (1N) and brine. The dried organics were concentrated to afford a residue that was purified by flash chromatography (1:9 to 2:8 EtOAc:PE) to give the title compound (56%) as a pale solid; (ES$^+$) m/z 354 (M+H)$^+$.

Step 5: methyl 2-bromo-3-[(1R,2S)-2-fluorocyclohexyl]-1H-indole-6-carboxylate and methyl 2-bromo-3-[(1S,2R)-2-fluorocyclohexyl]-1H-indole-6-carboxylate The preceding material was dissolved in MeOH and the enantiomers were separated by SFC chromatography (stationary phase: CHIRALCEL OJ-H 250×10 mm; mobile phase: 25% MeOH containing 0.2% diethylamine/CO$_2$; flow rate 10 mL/min; column pressure: 100 bar; column temperature: 35° C.; detection UV 254 nm). The enantiomeric excess of the two fractions thus obtained (compound recovery 95%) were determined by chiral phase analytical HPLC (stationary phase: CHIRALPAK AD 250×4.6mm; mobile phase 95:5 n-hexane:isopropyl alcohol containing 0.2% TFA; flow rate 1mL/min; detection: UV 300 nM; sample concentration: 1mg/mL; injection volume 10 uL): Isomer A (retention time 37.82 min, e.e. 99.8%, [α]$_D^{20}$=−8.0 (c =0.77, CHCl$_3$)); Isomer B (retention time 43.89 min, 99%, [α]$_D^{20}$=+8.0 (c =0.77, CHCl$_3$)).

Step 6: methyl 3-[(1R,2S) or (1S,2R)-2-fluorocyclohexyl]-2-(2-hydroxyphenyl)-1H-indole-6-carboxylate A solution (0.16 M) of (−)-methyl 2-bromo-3-[(trans)-2-fluorocyclohexyl]-1H-indole-6-carboxylate (isomer A from Step 5, above) in dioxane was treated with aqueous Na$_2$CO$_3$ (2 N, 4.6 eq), 2-hydroxyphenylboronic acid (1.8 eq) and Pd(PPh$_3$)$_4$ (0.1 eq). The mixture was stirred at 80° C. for 2 h, then diluted with EtOAc, washed with aqueous HCl (1N) and brine. The dried organic layer was concentrated in vacuo to give a residue that was purified by flash chromatography (8:2 PE:EtOAc) to give the title compound (90%) as a solid. $^1$H NMR (300 MHz, DMSO-d$_6$, 300 K) δ 1.21-1.65 (m, 3H), 1.68 (m, 4H), 2.05-2.19 (m, 1H), 2.75-2.97 (m, 1H), 3.87 (s, 3H), 5.00 (dm, J$_{HF}$ 49.0, 1H), 6.93 (t, J7.5, 1H), 7.01 (d, J7.5, 1H), 7.28 (t, J7.5, 1H), 7.29 (d, J 7.5, 1H), 7.59 (d, J 8.4, 1H), 7.82 (d, J 8.4, 1H), 8.02 (s, 1H), 9.74 (s, 1H), 11.34 (s, 1H).

Step 7: methyl(7R)-7-[(tert-butoxycarbonyl)amino]-14-[(1R,2S) or (1S,2R)-2-fluorocyclohexyl]-7,8-dihydro-6H-indolo[1,2-e][1,5]benzoxazocine-11-carboxylate The preceding material was treated as described in Example 1, Step 3 to furnish the title compound (96%) as a pale yellow oil. (ES$^+$) m/z 523 (M+H)$^+$

Step 8: methyl(7R)-7-amino-14-[(1R,2S) or (1S,2R)-2-fluorocyclohexyl]-7,8-dihydro-6H-indolo[1,2-e][1,5]benzoxazocine-11-carboxylate The preceding material was treated as described in Example 1, Step 4 to furnish the title compound (100%) as a yellow foam. (ES$^+$) m/z 423 (M+H)$^+$

Step 9: methyl(7R)-14-[(1R,2S) or (1S,2R)-2-fluorocyclohexyl]-7-(methylamino)-7,8-dihydro-6H-indolo[1,2-e][1,5]benzoxazocine-11-carboxylate The preceding material was treated as described in Example 1, Step 5 to furnish the title compound (73%) as a yellow foam. (ES) m/z 437 (M+H)$^+$

Step 10: methyl(7R)-7-[{2-[(tert-butoxycarbonyl)amino]ethyl}(methyl)amino]-14-[(1R,2S) or (1S,2R)-2-fluorocyclohexyl]-7,8-dihydro-6H-indolo[1,2-e][1,5]benzoxazocine-11-carboxylate The preceding material was treated as described in Example 1, Step 6 to furnish the title compound (80%). (ES$^+$) m/z 580 (M+H)$^+$

Step 11: (7R)-7-[{2-[(tert-butoxycarbonyl)amino]ethyl}(methyl)amino]-14-[(1R,2S) or (1S,2R)-2-fluorocyclohexyl]-7,8-dihydro-6H-indolo[1,2-e][1,5]benzoxazocine-11-carboxylic acid The preceding material was treated as described in Example 1, Step 7 to furnish the title compound (80%). (ES$^+$) m/z 566 (M+H)$^+$

Step 12: tert-butyl {2-[{(7R)-11-({[(3-chloropropyl)sulfonyl]amino}carbonyl)-14-[(1R,2S) or (1S,2R)-2-fluorocyclohexyl]-7,8-dihydro-6H-indolo[1,2-e][1,5]benzoxazocin-7-yl}(methyl)amino]ethyl} carbamate The preceding material was treated as described in Example 2, Step 2 to furnish the title compound used as crude in the next step. (ES$^+$) m/z 705 (M+H)$^+$; 707 (M+H)$^+$

Step 13: (7R)-7-[(2-aminoethyl)(methyl)amino]-N-[(3-chloropropyl)sulfonyl]-14-[(1R,2S) or (1S,2R)-2-fluorocyclohexyl]-7,8-dihydro-6H-indolo[1,2-e][1,5]benzoxazocine-11-carboxamide The preceding material was treated as described in Example 2, Step 3 to furnish the title compound (39% two steps). (ES$^+$) m/z 605 (M+H)$^+$; 607 (M+H)$^+$

Step 14: (7R)-14-[(1R,2S) or (1S,2R)-2-fluorocyclohexyl]-24-methyl-7,8-dihydro-6H-7,11-(epiminoethanoiminopropanothioiminomethano)indolo[1,2-e][1,5]benzoxazocin-15-one 17,17-dioxide The preceding material was treated as described in Example 2, Step 4 to furnish the title compound (4%). (ES$^+$) m/z 569 (M+H)$^+$.

Step 15: (7R)-14-[(1R,2S)) or (1S,2R)-2-fluorocyclohexyl]-21,24-dimethyl-7,8-dihydro-6H-7,11-(epiminoethanoiminopropanothioiminomethano)indolo[1,2-e][1,5]benzoxazocin-15-one17,17-dioxide The preceding material was treated as described in Example 3, Step 1 to furnish the title compound (15%). $^1$H NMR (400 MHz, DMSO-d$_6$+TFA, 330 K) δ 1.00-1.40 (m, 2H), 1.50-1.70 (m, 4H), 1.70-1.80 (m, 1H), 1.90-2.10 (m, 1H), 2.20-2.40 (m, 3H), 2.30 (s, 3H), 2.85 (s, 3H), 3.10-3.40 (m, 3H), 3.40-3.80 (m, 6H), 3.90-4.00 (m, 1H), 4.00-4.10 (m, 1H), 4.30-4.40 (m, 1H), 4.55-4.70 (m, 1H), 4.95-5.10 (m, 1H), 7.25-7.35 (m, 2H), 7.45-7.60 (m, 3H), 7.95 (d, J8.5, 1H), 8.16 (s, 1H); (ES$^+$) m/z 583 (M+H)$^+$.

EXAMPLE 5

7(R,S)-14-cyclohexyl-22-methyl-7,8-dihydro-6H-7,11-(ethanoiminobutanothioiminomethano)indolo[1,2-e][1,5]benzoxazocin-15-one 17,17-dioxide

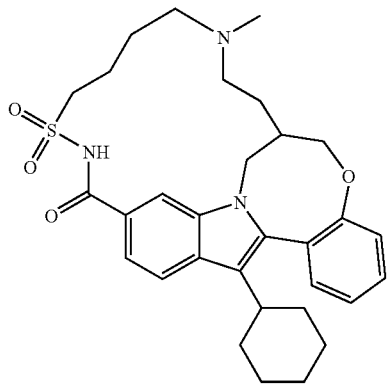

Step 1: methyl 14-cyclohexyl-7-methylene-7,8-dihydro-6H-indolo[1,2-e][1,5]benzoxazocine-11-carboxylate A solution of methyl 3-cyclohexyl-2-(2-hydroxyphenyl)-1H-indole-6-carboxylate (prepared as described in International patent application publication WO2006/046030, Example 9)(0.12 M) in DMF was treated with KO$^t$Bu (2.1 eq.) in one portion; the resulting mixture was stirred for 30 min at RT then treated dropwise with 3-chloro-2-(chloromethyl)prop-1-ene (1.1 eq.). The resulting solution was stirred at RT overnight before being quenched by addition of HCl (1N) and extracted into EtOAc. The combined organic layers were washed with sat. aq. NaHCO$_3$ and brine, before being dried (Na$_2$SO$_4$), filtered and concentrated in vacuo. The crude material was purified by FC (PE/EtOAc 85:15) affording the product as a yellow oil (97%). (ES$^+$) m/z 402 (M+H)$^+$.

Step 2: methyl(7R,S)-14-cyclohexyl-7-(hydroxymethyl)-7,8-dihydro-6H-indolo[1,2-e][1,5]benzoxazocine-11-carboxylate A solution of methyl 14-cyclohexyl-7-methylene-7,8-dihydro-6H-indolo[1,2-e][1,5]benzoxazocine-11-carboxylate (0.14 M) in THF was cooled to 0° C. and treated with 0.5 M 9-BBN in THF (5 eq.). The resulting solution was warmed to RT and stirred for 3 h before re-cooling to 0° C. 1N NaOH (3 eq.) and H$_2$O$_2$ (2 eq.) were added and the solution warmed to RT for 2 h before diluting with EtOAc. The organic layers were washed with water then brine, before being dried (Na$_2$SO$_4$), filtered and concentrated in vacuo. The material was taken on without further purification. (ES$^+$) m/z 420 (M+H)$^+$.

Step 3: methyl(7R,S)-14-cyclohexyl-7-({[(4-methylphenyl)sulfonyl]oxy}methyl)-7,8-dihydro-6H-indolo[1,2-e][1,5]benzoxazocine-11-carboxylate A solution of methyl 14-cyclohexyl-7(R,S)-(hydroxymethyl)-7,8-dihydro-6H-indolo[1,2-e][1,5]benzoxazocine-11-carboxylate (0.14 M) in DCM was treated with TsCl (3.5 eq.) and pyridine (35 eq.) and the resulting mixture was stirred overnight at RT. The reaction was quenched by addition of HCl (1N) and extracted into EtOAc. The combined organic layers were washed with sat. aq. NaHCO$_3$ and brine, dried over Na$_2$SO$_4$, filtered and concentrated in vacuo. The crude material was purified by FC (PE/EtOAc 90:10) affording the product as a yellow oil (95%, over steps 2, 3). (ES$^+$) m/z 574 (M+H)$^+$.

Step 4: methyl 7(R,S)-(cyanomethyl)-14-cyclohexyl-7,8-dihydro-6H-indolo[1,2-e][1,5]benzoxazocine-11-carboxylate A solution of methyl 14-cyclohexyl-7(R,S)-({[(4-methylphenyl)sulfonyl]oxy}methyl)-7,8-dihydro-6H-indolo[1,2-e][1,5]benzoxazocine-11-carboxylate (0.35 M) in DMF was treated with NaCN (1.2 eq.) and the resulting mixture was stirred overnight at RT. The reaction was quenched by addition of sat. aq. NaHCO$_3$ and extracted into EtOAc. The combined organic layers were washed with brine, before being dried (Na$_2$SO$_4$), filtered and concentrated in vacuo. The crude material was purified by FC (PE/EtOAc 90:10) affording the product as a yellow foam (90%). (ES$^+$) m/z 429 (M+H)$^+$.

Step 5: methyl 7(R,S)-(2-aminoethyl)-14-cyclohexyl-7,8-dihydro-6H-indolo[1,2-e][1,5]benzoxazocine-11-carboxylate Platinum(IV) oxide (0.5 eq.) was added to a solution of methyl 7(R,S)-(cyanomethyl)-14-cyclohexyl-7,8-dihydro-6H-indolo[1,2-e][1,5]benzoxazocine-11-carboxylate (0.20 M) in MeOH. The atmosphere in the reaction vessel was exchanged for H$_2$, and the reaction stirred vigorously at RT for 4 h. The reaction vessel was flushed with N$_2$, and the reaction mixture filtered through a plug of CELITE (washing well with MeOH and EtOAc). Volatiles were removed in vacuo to afford the crude product which was purified by FC (EtOAc/MeOH/Et$_3$N 93:5:2) affording the product as a yellow oil (12%). (ES$^+$) m/z 433 (M+H)$^+$.

Step 6: methyl(7R,S)-14-cyclohexyl-7-[2-(methylamino)ethyl]-7,8-dihydro-6H-indolo[1,2-e][1,5]benzoxazocine-11-carboxylate A solution of methyl 7(R,S)-(2-aminoethyl)-14-cyclohexyl-7,8-dihydro-6H-indolo[1,2-e][1,5]benzoxazocine-11-carboxylate (0.08 M) in THF was treated dropwise with 2,2,2-trifluoroethyl formate (2 eq.) and stirred overnight at RT. The volatiles were removed in vacuo and the residue dissolved (0.02 M) in THF and treated dropwise with BH$_3$-DMS complex (2M in THF; 10 eq.). The resulting solution was stirred at RT for 3 h. The reaction was quenched by the careful addition of HCl/MeOH (1.25 M) and the resulting solution refluxed for 2 h. The volatiles were then removed in vacuo and the residue partitioned between sat. aq. NaHCO₃ and EtOAc. The combined organics were washed with brine, dried (Na₂SO₄), filtered and concentrated in vacuo to afford the product which was used directly in the next step. (ES⁺) m/z 447 (M+H)⁺.

Step 7: methyl 7(R,S)-{2-[[4-(aminosulfonyl)butanoyl](methyl)amino]ethyl}-14-cyclohexyl-7,8-dihydro-6H-indolo[1,2-e][1,5]benzoxazocine-11-carboxylate A solution of methyl(7R,S)-14-cyclohexyl-7-[2-(methylamino)ethyl]-7,8-dihydro-6H-indolo[1,2-e][1,5]benzoxazocine-11-carboxylate methyl(0.08 M) in DCM was treated with 4-(aminosulfonyl)butanoic acid (1.2 eq.) followed by DIC (1.1 eq.) and HOBt (1.1 eq.) and the resulting mixture was stirred overnight at RT. The reaction was diluted with EtOAc and the combined organic layers were washed with sat. aq NaHCO₃, sat. aq. NH₄Cl and brine, before being dried (Na₂SO₄), filtered and concentrated in vacuo. The product was used directly in the next step without further purification. (ES⁺) m/z 596 (M+H)⁺.

Step 8: 7(R,S)-{2-[[4-(aminosulfonyl)butyl](methyl) amino]ethyl}-14-cyclohexyl-7,8-dihydro-6H-indolo [1,2-e][1,5]benzoxazocine-11-carboxylic acid A solution of methyl 7(R,S)-{2-[[4-(aminosulfonyl)butanoyl](methyl)amino]ethyl}-14-cyclohexyl-7,8-dihydro-6H-indolo[1,2-e][1,5]benzoxazocine-11-carboxylate (0.08 M) in THF was treated with BH₃-DMS complex (2M in THF; 10 eq.), and the resulting mixture was stirred for 3 h at RT. The reaction was quenched by the careful addition of HCl/MeOH (1.25 M), and the resulting solution refluxed for 2 h. The volatiles were then removed in vacuo, and the residue redissolved in MeOH. 2N NaOH (10 eq.) was added, and the resulting mixture heated at 70° C. for 3 h. The volatiles were evaporated in vacuo, and the residue purified by automated RP-HPLC (WATERS XTERRA column; MeCN/H₂O/0.1% TFA gradient). Fractions containing the pure compound were combined and lyophilized in the presence of excess HCl to afford the hydrochloride salt of the product as a white powder (8% overall for steps 6, 7, 8). (ES⁺) m/z 568 (M+H)⁺.

Step 9: 7(R,S)-14-cyclohexyl-22-methyl-7,8-dihydro-6H-7,11-(ethanoiminobutanothioiminomethano) indolo[1,2-e][1,5]benzoxazocin-15-one 17,17-dioxide A solution of 7(R,S)-{2-[[4-(aminosulfonyl)butyl](methyl)amino]ethyl}-14-cyclohexyl-7,8-dihydro-6H-indolo[1,2-e][1,5]benzoxazocine-11-carboxylic acid (0.002 M) in DCM was treated with EDC (2 eq.), DMAP (2 eq.) and DIPEA (4 eq.), and the resulting mixture was stirred for 72 h at RT. The reaction was quenched by addition of 1N HCl and extracted into EtOAc. The combined organic layers were washed with brine, before being dried (Na₂SO₄), filtered and concentrated in vacuo. The residue was purified by RP-HPLC (WATERS XTERRA column; MeCN/H₂O/0.1% TFA gradient). Fractions containing the pure compound were combined and lyophilized to afford the product as a white powder (16%); this material was identified as a 4:1* mixture of diastereomers by ¹H NMR. ¹H NMR (600 MHz, DMSO-d₆+TFA, 320 K) δ 1.14-1.39 (m, 3H), 1.46-1.95 (m, 11H), 2.20-2.25 (m, 1H), 2.65-2.70 (m, 1H), 2.76* and 2.80 (s, 3H), 3.00-3.07 (m, 2H), 3.16-3.21 (m, 2H), 3.49-3.54 (m, 1H), 3.58-3.73 and 4.33-4.39* and 4.48-4.55* (m, 4H), 3.77-3.81 and 4.02-4.04* (m, 1H), 3.96-3.98 and 4.68-4.71* (m, 1H), 4.04-4.08 and 4.18-4.21* (m, 1H), 7.16-7.23 (m, 1H), 7.31-7.37 (m, 2H), 7.47-7.49* and 7.55-7.58 (m, 1H), 7.51-7.52 and 7.60-7.62* (m, 1H), 7.91-7.95 (m, 1H), 8.09 and 8.53* (s, 1H); (ES⁺) m/z 550 (M+H)⁺.

EXAMPLE 6

(7R)-14-cyclohexyl-20,24-dimethyl-7,8-dihydro-6H-7,11-(epiminopropanoiminoethanothioiminomethano)indolo[1,2-e][1,5]benzoxazocin-15-one 17,17-dioxide

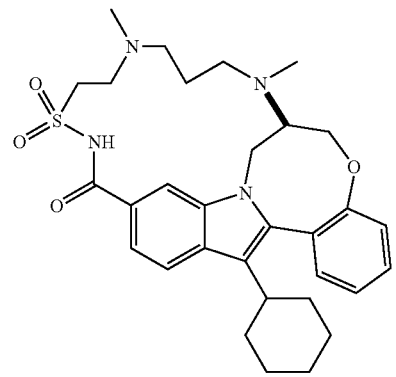

Step 1: N-benzylethylene sulfonamide

Chloroethansulfonyl chloride was added dropwise to a stirred solution of benzylamine (1.0 eq.) and Et₃N (1.1 eq.) in DCM (0.3 M) at 0° C. The solution was stirred at RT overnight. The reaction was washed with 10% citric acid aq., sat. aq. NaHCO₃, brine, dried (Na₂SO₄), filtered and concentrated in vacuo to afford the product (50%). ¹H NMR (300 MHz, DMSO-d₆, 300 K) δ 4.04 (d, J 6.1, 2H), 5.92 (d, J 10.1, 1H), 5.99 (d, J 16.5, 1H), 6.63 (dd, J 16.53, 10.1, 1H), 7.30-7.32 (m, 5H), 7.77-7.81 (m, 1H).

Step 2: methyl(7R)-7-[[N-(tert-butoxycarbonyl)-β-alanyl](methyl)amino]-14-cyclohexyl-7,8-dihydro-6H-indolo[1,2-e][1,5]benzoxazocine-11-carboxylate A solution of methyl(7R)-14-cyclohexyl-7-(methylamino)-7,8-dihydro-6H-indolo[1,2-e][1,5]benzoxazocine-11-carboxylate (prepared as described in Example 1, Step 5) and N-(tert-butoxycarbonyl)-β-alanine (1.2 eq) in DCM (0.15 M) was treated with HATU (1.3 eq.) and DIPEA (3 eq.) and the resulting mixture was stirred for 90 min at RT. The reaction was diluted with EtOAc and the combined organic layers were washed with 1N HCl (aq), sat aq NaHCO₃ then brine, before being dried (Na₂SO₄), filtered and concentrated in vacuo. The product was used directly in the next step without further purification. (ES⁺) m/z 590 (M+H)⁺.

Step 3: methyl(7R)-7-[β-alanyl(methyl)amino]-14-cyclohexyl-7,8-dihydro-6H-indolo[1,2-e][1,5]benzoxazocine-11-carboxylate A solution of methyl(7R)-7-[[N-(tert-butoxycarbonyl)-β-alanyl](methyl)amino]-14-cyclohexyl-7,8-dihydro-6H-indolo[1,2-e][1,5]benzoxazocine-11-carboxylate (0.15 M) in DCM was treated with TFA (10 eq.) and the resulting mixture was stirred for 4h at RT before removing all volatiles in vacuo. The residue was partitioned between EtOAc and sat aq NaHCO$_3$ and the layers separated. The combined organics were washed with brine, before being dried (Na$_2$SO$_4$), filtered and concentrated in vacuo. The product was used directly in the next step without further purification. (ES$^+$) m/z 490 (M+H)$^+$.

Step 4: methyl(7R)-7-[(3-aminopropyl)(methyl) amino]-14-cyclohexyl-7,8-dihydro-6H-indolo[1,2-e] [1,5]benzoxazocine-11-carboxylate A solution of methyl(7R)-7-[β-alanyl(methyl)amino]-14-cyclohexyl-7,8-dihydro-6H-indolo[1,2-e][1,5]benzoxazocine-11-carboxylate (0.2 M) in THF was treated with BH$_3$-DMS complex (2 M in THF; 10 eq.) and the resulting mixture was stirred for 3 h at RT. The reaction was quenched by the careful addition of HCl/MeOH (1.25 M) and the resulting solution refluxed for 2 h. The volatiles were then removed in vacuo and the residue partitioned between sat. aq. NaHCO$_3$ and EtOAc. The combined organics were washed with brine, dried (Na$_2$SO$_4$), filtered and concentrated in vacuo. The product was used directly in the next step without further purification. (ES$^+$) m/z 476 (M+H)$^+$.

Step 5: methyl(7R)-14-cyclohexyl-7-{methyl[3-(methylamino)propyl]amino}-7,8-dihydro-6H-indolo[1, 2-e][1,5]benzoxazocine-11-carboxylate A solution of methyl(7R)-7-[(3-aminopropyl)(methyl) amino]-14-cyclohexyl-7,8-dihydro-6H-indolo[1,2-e][1,5] benzoxazocine-11-carboxylate (0.16 M) in THF was treated dropwise with 2,2,2-trifluoroethyl formate (1.3 eq.) and stirred overnight at RT. The volatiles were removed in vacuo and the residue dissolved (0.08 M) in THF and treated dropwise with BH$_3$-DMS complex (2 M in THF; 10 eq.). The resulting solution was stirred at RT for 3 h. The reaction was quenched by the careful addition of HCl/MeOH (1.25 M) and the resulting solution refluxed for 2 h. The volatiles were then removed in vacuo and the residue partitioned between sat. aq. NaHCO$_3$ and EtOAc. The combined organics were washed with brine, dried (Na$_2$SO$_4$), filtered and concentrated in vacuo. The crude material was purified by FC (EtOAc/MeOH/Et$_3$N 90:8:2) affording the product as a pale orange solid (80% overall for steps 2, 3, 4, 5). (ES) m/z 490 (M+H)$^+$.

Step 6: methyl(7R)-7-[{3-[{2-[(benzylamino)sulfonyl]ethyl}(methyl)amino]propyl}(methyl)amino]-14-cyclohexyl-7,8-dihydro-6H-indolo[1,2-e][1,5]benzoxazocine-11-carboxylate A solution of methyl (7R)-14-cyclohexyl-7-{methyl[3-(methylamino)propyl]amino}-7,8-dihydro-6H-indolo[1,2-e][1,5]benzoxazocine-11-carboxylate (0.10 M) in MeCN was treated with N-benzylethylenesulfonamide (prepared as described in Step 1)(1.3 eq.), K$_2$CO$_3$ (6 eq.) and BnNEt$_3$Cl (0.2 eq.), and the resulting mixture was stirred overnight at 50° C. A further portion of N-benzylethylenesulfonamide (1.3 eq.) was added, and heating continued for 8 h. The reaction was cooled before all volatiles were evaporated in vacuo, and the residue purified by automated RP-HPLC (W$_{ATERS}$ XT$_{ERRA}$ column; MeCN/H$_2$O/0.1% TFA gradient). Fractions containing the pure compound were combined and lyophilized to afford the product as a white powder (17%). (ES$^{+)\ m/z}$ 687 (M+H)$^+$.

Step 7: (7R)-7-[{3-[{2-[(benzylamino)sulfonyl] ethyl}(methyl)amino]propyl}(methyl)amino]-14-cyclohexyl-7,8-dihydro-6H-indolo[1,2-e][1,5]benzoxazocine-11-carboxylic acid A solution of methyl(7R)-7-[{3-[{2-[(benzylamino)sulfonyl]ethyl}(methyl)amino]-propyl}(methyl)amino]-14-cyclohexyl-7,8-dihydro-6H-indolo[1,2-e][1,5]benzoxazocine-11-carboxylate (0.15 M) in dioxane was treated with 2N NaOH (40 eq.) and the resulting mixture was stirred for 3 h at 60° C. The mixture was cooled before addition of 6N HCl (45 eq.) and extracting into EtOAc (×3). The combined organics were washed with brine, before being dried (Na$_2$SO$_4$), filtered and concentrated in vacuo. The product was used directly in the next step without further purification; (ES$^+$) m/z 673 (M+H)$^+$.

Step 8: (7R)-14-cyclohexyl-20,24-dimethyl-7,8-dihydro-6H-7,11-(epiminopropanoiminoethan-othioiminomethano)indolo[1,2-e][1,5]benzoxazocin-15-one 17,17-dioxide A solution of (7R)-7-[{3-[{2[(benzylamino)sulfonyl] ethyl}(methyl)amino]propyl}(methyl)amino]-14-cyclohexyl-7,8-dihydro-6H-indolo[1,2-e][1,5]benzoxazocine-11-carboxylic acid (0.01 M) in DCM/DMF (1:1) was treated with EDC (1.5 eq.) and DMAP (5 eq.), and the resulting mixture was stirred for 5 h at 50° C. DCM was removed in vacuo, and the remaining solution diluted with an equal volume of MeOH. Pd/C (10 wt %) was introduced under N$_2$, the atmosphere in the reaction vessel was exchanged for H$_2$, and the reaction stirred vigorously overnight at RT. The reaction vessel was flushed with N$_2$, and the reaction mixture filtered through a plug of C$_{ELITE}$ (washing well with MeOH and EtOAc). Volatiles were removed in vacuo to afford the crude product, which was purified by RP-HPLC (W$_{ATERS}$ XT$_{ERRA}$ column; MeCN/H$_2$O/0.1% TFA gradient). Fractions containing the pure compound were combined and lyophilized to afford the product as a white powder (23% overall for steps 7,8). $^1$1-1NMR (400 MHz, DMSO-d$_6$+TFA, 300 K) δ1.11-1.18 (m, 1H), 1.28-1.41 (m, 2H), 1.50-1.54 (m, 1H), 1.66-1.74 (m, 2H), 1.82-1.88 (m, 1H), 1.89-2.00 (m, 3H), 2.04-2.20 (m, 2H), 2.67-2.71 (m, 1H), 2.85 (s, 3H), 2.95 (s, 3H), 3.25-3.29 (m, 2H), 3.32-3.38 (m, 1H), 3.44-3.51 (m, 1H), 3.60-3.73 (m, 3H), 3.87-3.93 (m, 1H), 4.09-4.14 (m, 1H), 4.30-4.21 (m, 2H), 4.39-4.34 (m, 1H), 4.91-4.94 (m, 1H), 7.27-7.31 (m, 2H), 7.35 (d, J6.6, 1H), 7.52-7.57 (m, 2H), 7.98 (d, J8.3, 1H), 8.15 (s, 1H); (ES+) m/z 565 (M+H)+.

EXAMPLE 7

13-cyclohexyl-19,22-dimethyl-6,7-dihydro-10,6-(methanoiminothioethanoimino-ethanoiminomethano)indolo[1,2-d][1,4]benzoxazepin-14-one 16,16-dioxide

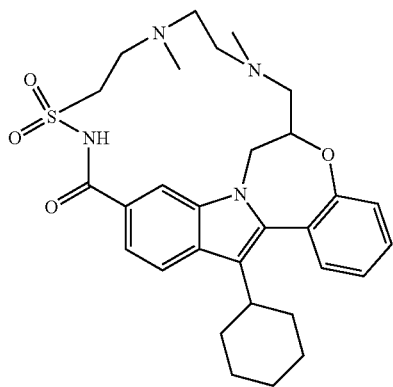

Step 1: dimethyl 13-cyclohexyl-6,7-dihydroindolo[1,2-d][1,4]benzoxazepine-6,10-dicarboxylate Methyl chloroacrylate (1.7 eq.), triethylbutyl ammonium chloride (0.2 eq.) and K$_2$CO$_3$ (6 eq.) were added to a solution of methyl 3-cyclohexyl-2-(2-hydroxyphenyl)-1H-indole-6-carboxylate (prepared as described in International patent application publication WO2006/046030, Example 9) in anhydrous MeCN (0.02 M). The mixture was heated at 60° C. overnight and then allowed to cool to RT. Volatiles were removed in vacuo, diluted with EtOAc, washed with water, dried (Na$_2$SO$_4$), filtered and concentrated in vacuo. The crude product was purified by FC (EtOAc/PE 10:90) to afford the product as a solid (81%). (ES+) m/z 434 (M+H)+.

Step 2: 13-cyclohexyl-10-(methoxycarbonyl)-6,7-dihydroindolo[1,2-d][1,4]benzoxazepine-6-carboxylic acid Dimethyl 13-cyclohexyl-6,7-dihydroindolo[1,2-d][1,4]benzoxazepine-6,10-dicarboxylate was dissolved in THF:MeOH (1:1) (0.02 M) and to that solution 1.4 eq. of an aq. solution of lithium hydroxide monohydrate (0.1 N) were added. The solution was stirred at RT for 2 h. Volatiles were reduced in vacuo, the residue acidified with 1N HCl (aq) and the resultant precipitate filtered and dried in vacuo to afford the title compound (99%). (ES+) m/z 420 (M+H)+.

Step 3: methyl 13-cyclohexyl-6-(hydroxymethyl)-6,7-dihydroindolo[1,2-d][1,4]benzoxazepine-10-carboxylate To a solution of 13-cyclohexyl-10-(methoxycarbonyl)-6,7-dihydroindolo[1,2-d][1,4]benzoxazepine-6-carboxylic acid in THF (0.03 M), 1.6 eq. of BH$_3$.THF (1 M solution in THF) was added and the reaction allowed to stir at 60° C. for 1 h. Then 11.6 eq. of BH$_3$.THF (1 M solution in THF) were added and the reaction allowed to stir at 60° C. for another hour, before being quenched by the careful addition of HCl/MeOH (1.25 M). The resulting solution was refluxed for 2 h. The mixture was allowed to cool to RT, the volatiles were removed in vacuo and the residue partitioned between sat. aq. NaHCO$_3$ and EtOAc. The combined organics were washed with brine, before drying (Na$_2$SO$_4$), filtering and concentrating in vacuo to afford the product (97%). (ES+) m/z 406 (M+H)+.

Step 4: methyl 13-cyclohexyl-6-formyl-6,7-dihydroindolon[1,2-di][1,4]benzoxazepine-10-carboxylate A solution of methyl 13-cyclohexyl-6-(hydroxymethyl)-6,7-dihydroindolo[1,2-d][1,4]benzoxazepine-10-carboxylate in DCM (0.03 M) was added to a solution of DMP (1.2 eq.) in DCM (0.06 M) at 0° C. and then left for 2 h. at RT. The mixture was diluted with EtOAc, washed with sat. aq. NaHCO$_3$, brine, before drying (Na$_2$SO$_4$), filtering and concentrating in vacuo to afford the product (97%). (ES+) m/z 404 (M+H)+.

Step 5: methyl 6-{[{2-[(tert-butoxycarbonyl)(methyl)amino]ethyl}(methyl)-amino]methyl}-13-cyclohexyl-6,7-dihydroindolo[1,2-d][1,4]benzoxazepine-10-carboxylate To a solution of methyl 13-cyclohexyl-6-formyl-6,7-dihydroindolo[1,2-d][1,4]benzoxazepine-10-carboxylate in MeOH (0.03 M) and tert-butyl methyl[2-(methylamino)ethyl] carbamate (prepared as described in European patent application publication EP 0296811 A2, from commercially available N,N'-dimethylethylenediamine) (3 eq.), was added AcOH to adjust the pH to 6. The reaction was allowed to stir for 15 min., and then a solution of NaCNBH$_3$ (1 eq.) and ZnCl$_2$ (0.3 M; 0.55 eq.) in MeOH was added. The solution stirred at RT overnight. The reaction mixture was concentrated, diluted with EtOAc and the organic phase washed with sat. aq. NaHCO$_3$ and brine. The organic phase was dried (Na$_2$SO$_4$), filtered and concentrated in vacuo. The crude product was purified by FC (EtOAc/PE/Et$_3$N 19:80:1) to afford the product (61%). (ES+) m/z 576 (M+H)+.

Step 6: methyl 13-cyclohexyl-6-({methyl[2-(methylamino)ethyl]amino}methyl-6,7-dihydroindolo[1,2-d][1,4]benzoxazepine-10-carboxylate A solution of methyl 6-{[{2-[(tert-butoxycarbonyl)(methyl)amino]ethyl}(methyl)-amino]methyl}-13-cyclohexyl-6,7-dihydro indolo[1,2-d][1,4]benzoxazepine-10-carboxylate in DCM (0.09 M) was treated with TFA (142 eq.) at 0° C. The reaction was concentrated, diluted with EtOAc and washed with sat. aq. NaHCO$_3$, brine, dried (Na$_2$SO$_4$), filtered and concentrated in vacuo to afford the product (100%). (ES+) m/z 476 (M+H)+.

Step 7: methyl 13-cyclohexyl-6-(2,5-dimethyl-8,8-dioxido-10-phenyl-8-thia-2,5,9-triazadec-1-yl)-6,7-dihydroindolo[1,2-d][1,4]benzoxazepine-10-carboxylate A solution of methyl 13-cyclohexyl-6-({methyl[2-(methylamino)ethyl]amino}methyl -6,7-dihydroindolo[1,2-d][1,4]benzoxazepine-10-carboxylate in MeCN (0.04 M) was treated with N-benzylethylene sulfonamide (prepared as described in Example 6, Step 1) (1 eq.), K$_2$CO$_3$ (6.0 eq.) and benzyltriethylammonuim chloride (0.2 eq.). The reaction was heated at 60° C. for 2 h. The reaction was heated at 60° C. for a further 24h, with an additional 5 eq. of N-benzylethylene sulfonamide being added at intervals over that time. The reaction was concentrated, and the residue purified by automated RP-HPLC (WATERS SYMMETRY SHIELD RP 18 column, 7 μtM, 19×300 mm; MeCN/H$_2$O/0.1% TFA gradient). Fractions containing the pure compound were combined and lyophilized to afford the product as a white powder (21%). (ES$^+$) m/z 673 (M+H)$^+$.

Step 8: 13-cyclohexyl-6-(2,5-dimethyl-8,8-dioxido-10-phenyl-8-thia-2,5,9-triazadec-1-yl)-6,7-dihydroindolo[1,2-d][1,4]benzoxazepine-10-carboxylic acid KOH (5.0 eq.) was added to a solution of methyl 13-cyclohexyl-6-(2,5-dimethyl-8,8-dioxido-10-phenyl-8-thia-2,5,9-triazadec-1-yl)-6,7-dihydroindolo[1,2-d][1,4]benzoxazepine-10-carboxylate (0.02 M) in dioxane/H$_2$O (1/1). The reaction was heated at 60° C. for 4.5 h. The reaction was allowed to cool to RT and acidified with 1N HCl (aq), the mixture was extracted two times with DCM. The combined organics were washed with brine, dried (Na$_2$SO$_4$), filtered and concentrated in vacuo to afford the product (quant.). (ES$^+$) m/z 659 (M+H)$^+$.

Step 9: 15-benzyl-13-cyclohexyl-19,22-dimethyl-6,7-dihydro-10,6-(methanoiminothioethanoiminoethanoiminomethano)indolo[1,2-d][1,4]benzoxazepin-14-one 16,16-dioxide EDC (1.5 eq.) and DMAP (2.5 eq.) were added to a solution of 13-cyclohexyl-6-(2,5-dimethyl-8,8-dioxido-10-phenyl-8-thia-2,5,9-triazadec-1-yl)-6,7-dihydroindolo[1,2-d][1,4]benzoxazepine-10-carboxylic acid (3 mM) in DCM. The reaction was stirred under N$_2$ at 40° C. overnight. The reaction was allowed to cool to RT and washed with sat. aq. NaHCO$_3$, brine, dried (Na$_2$SO$_4$), filtered and concentrated in vacuo to afford the product (quant.). (ES) m/z 641 (M+H)$^+$.

Step 10: 13-cyclohexyl-19,22-dimethyl-6,7-dihydro-10,6-(methanoiminothioethanoiminoethanoiminomethano)indolo[1,2-d][1,4]benzoxazepin-14-one 16,16-dioxide Pd/C (10 wt %) was added as a solution of 15-benzyl-13-cyclohexyl-19,22-dimethyl-6,7-dihydro-10,6-(methanoiminothioethanoiminoethanoiminomethano)indolo[1,2-d][1,4]benzoxazepin-14-one 16,16-dioxide (7.1 mM) in DMF under N$_2$. The atmosphere in the reaction vessel was exchanged for H$_2$, and the reaction stirred vigorously at RT for 48 h. The reaction vessel was flushed with N$_2$, and the reaction mixture filtered. Volatiles were removed in vacuo, and the residue purified by automated RP-HPLC (WATERS SYMMETRY SHIELD RP 18 column, 7$_1$1M, 19×300 mm; MeCN/H$_2$O/0.1% TFA gradient). Fractions containing the pure compound were combined and lyophilized to afford the product as a white powder (3%). $^1$H NMR (600 MHz, DMSO-d$_6$ +TFA, 300 K) δ1.17-1.59 (m, 4H), 1.67-2.18 (m, 6H), 2.82 (s, 3H), 2.85-2.98 (m, 4H), 3.02-3.11 (m, 1H), 3.26-3.35 (m, 1H), 3.44-3.68 (m, 3H), 3.69-3.76 (m, 1H), 3.81-3.90 (m, 1H), 3.99-4.08 (m, 1H), 4.12-4.25 (m, 1H), 4.77-4.90 (m, 1H), 4.96-5.08 (m, 1H), 7.38 (d, J 7.8, 1H), 7.44 (t, J 7.8, 1H), 7.51-7.55 (m, 3H), 7.98 (d, J 8.4, 1H), 8.17 (s, 1H); (ES$^+$) m/z 551 (M+H)$^+$.

EXAMPLE 8

(7R)-14-cyclohexyl-22,25-dimethyl-7,8-dihydro-6H-7,11-(epiminoethanoiminobutanothioiminomethano)indolo[1,2-e][1,5]benzoxazocin-15-one 17,17-dioxide

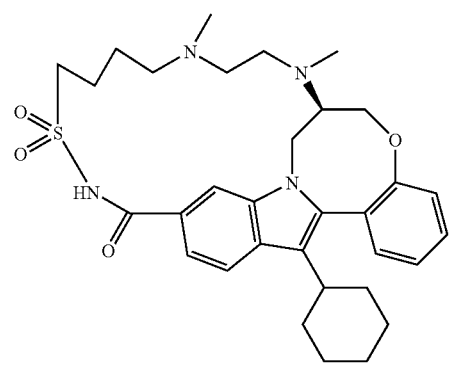

Step 1: methyl(7R)-7-[(2-aminoethyl)(methyl)amino]-14-cyclohexyl-7,8-dihydro-6H-indolo[1,2-e][1,5]benzoxazocine-11-carboxylate A solution of methyl(7R)-7-[{2-[(tert-butoxycarbonyl)amino]ethyl}(methyl)amino]-14-cyclohexyl-7,8-dihydro-6H-indolo[1,2-e][1,5]benzoxazocine-11-carboxylate (prepared as described in Example 1, Step 6) (0.1 M) in DCM was treated with an excess of TFA (>50 eq.). The mixture was stirred at RT for 1 h. All the volatiles were then removed in vacuo and the residue treated with a solution of HCl/Et$_2$O (2 M) and the resulting mixture concentrated in vacuo. The product was used in the next step without further purification. (ES$^+$) m/z 462 (M+H)$^+$.

Step 2: methyl(7R)-14-cyclohexyl-7-{methyl[2-(methylamino)ethyl]amino}-7,8-dihydro-6H-indolo[1,2-e][1,5]benzoxazocine-11-carboxylate A solution (0.1 M) of methyl(7R)-7-[(2-aminoethyl)(methyl)amino]-14-cyclohexyl-7,8-dihydro-6H-indolo[1,2-e][1,5]benzoxazocine-11-carboxylate in THF was treated dropwise with 2,2,2-trifluoroethyl formate (1.5 eq.) and stirred overnight at RT. The volatiles were removed in vacuo and the residue dissolved (0.1 M) in THF and treated dropwise with BH$_3$-DMS complex (2M in THF; 5 eq.). The resulting solution was stirred at RT for 3 h. The reaction was quenched by the careful addition of HCl/MeOH (1.25 M) and the resulting solution heated to dryness. The residue was then partitioned between sat. aq. NaHCO$_3$ and EtOAc. The combined organics were washed with brine, dried (Na$_2$SO$_4$), filtered and concentrated in vacuo. The crude was purified by FC (EtOAc/MeOH 99.5:0.5+1% NEt$_3$) to afford the product (40%). (ES$^+$) m/z 476 (M+H)$^+$.

Step 3: methyl(7R)-7-[{2-[[4-(aminosulfonyl)butanoyl](methyl)amino]ethyl}(methyl)-amino]-14-cyclohexyl-7,8-dihydro-6H-indolo[1,2-e][1,5]benzoxazocine-11-carboxylate 4-(aminosulfonyl)butanoic acid (1.2 eq.), DIPEA (2 eq.), DIC (1.1 eq.) and HOBT (1.1 eq.) were added to a solution of methyl(7R)-14-cyclohexyl-7-{methyl[2-(methylamino)ethyl]amino}-7,8-dihydro-6H-indolo[1,2-e][1,5]benzoxazocine-11-carboxylate (0.07 M) in DMF. The reaction was stirred under $N_2$ at RT overnight. The mixture was then partitioned between sat. aq. $NaHCO_3$ and EtOAc. The combined organics were washed with 1N HCl followed by brine, dried ($Na_2SO_4$), filtered and concentrated in vacuo. The product was used in the next step without further purification. ($ES^+$) m/z 625 $(M+H)^+$.

Step 4: methyl(7R)-7-[{2-[[4-(aminosulfonyl)butyl](methyl)amino]ethyl}(methyl)amino]-14-cyclohexyl-7,8-dihydro-6H-indolo[1,2-e][1,5]benzoxazocine-11-carboxylate A solution of methyl(7R)-7-[{2-[[4-(aminosulfonyl)butanoyl](methyl)amino]ethyl}-(methyl)amino]-14-cyclohexyl-7,8-dihydro -6H-indolo[1,2-e][1,5]benzoxazocine-11-carboxylate (0.03 M) in THF was treated with $BH_3.DMS$ complex (2 M in THF; 15 eq.). The resulting solution was stirred at RT for 1 h. The reaction was quenched by the careful addition of HCl/MeOH (1.25 M) and the resulting solution heated at 80° C. until all volatiles had evaporated to afford the title compound. The product was used in the next step without further purification. ($ES^+$) m/z 611 $(M+H)^+$.

Step 5: (7R)-7-[{2-[[4-(aminosulfonyl)butyl](methyl)amino]ethyl}(methyl)amino]-14-cyclohexyl-7,8-dihydro-6H-indolo[1,2-e][1,5]benzoxazocine-11-carboxylic acid Sodium hydroxide (1N, 5 eq.) was added to a solution of methyl (7R)-7-[{2-[[4-(aminosulfonyl)butyl](methyl)amino]ethyl}(methyl)amino]-1 4-cyclohexyl-7,8-dihydro-6H-indolo[1,2-e][1,5]benzoxazocine-11-carboxylate (0.03 M) in MeOH. The reaction was heated at 60° C. for 1 h prior to introducing further sodium hydroxide (2 N, 5 eq.) and continuing heating for 30 min. The reaction mixture was concentrated in vacuo, redissolved in DMSO and purified by RP-HPLC (Waters XTerra column, C18, 5um, 19×100 mm. Mobile phase: $MeCN/H_2O$ buffered with 0.1% TFA). Fractions containing the pure compound were combined and freeze dried to afford the title compound (37%) as a white powder. ($ES^+$) m/z 597 $(M+H)^+$.

Step 6: (7R)-14-cyclohexyl-22,25-dimethyl-7,8-dihydro-6H-7,11-(epiminoethanoiminobutanothioiminomethano)indolo[1,2-e][1,5]benzoxazocin-15-one 17,17-dioxide DMAP (4 eq.) and EDC (2 eq.) were added to a solution of (7R)-7-[{2-[[4-(aminosulfonyl)butyl](methyl)amino]ethyl}methyl)amino]-14-cyclohexyl-7,8-dihydro-6H-indolo[1,2-e][1,5]benzoxazocine-11-carboxylic acid (2 mM) in DCM. The reaction was stirred under $N_2$ at RT overnight. All volatiles were removed in vacuo, and the residue purified by RP-HPLC (Waters XTerra column, C18, 5um, 19×100 mm. Mobile phase: $MeCN/H_2O$ buffered with 0.1% TFA). Fractions containing the pure compound were combined and lyophilized to afford the product as a white powder (31%). $^1H$ NMR (400 MHz, DMSO-$d_6$+TFA, 335 K) δ1.10-1.50 (m, 4H), 1.60-1.80 (m, 2H), 1.80-2.00 (m, 8H), 2.60-2.70 (m, 1H), 2.79 (s, 3H), 2.82 (s, 3H), 3.10-3.30 (m, 2H), 3.50-3.70 (m, 6H), 3.70-3.80 (m, 1H), 4.20-4.50 (m, 3H), 4.85-4.95 (m, 1H), 7.20-7.40 (m, 3H), 7.50-7.60 (m, 2H), 7.92 (d, J 8.4, 1H), 8.4 (s, 1H); ($ES^+$) m/z 579 $(M+H)^+$.

EXAMPLE 9

(7S)-14-cyclohexyl-21-methyl-7,8-dihydro-6H-7,11-(epoxyethanoiminopropanothioiminomethano)indolo[1,2-e][1,5]benzoxazocin-15-one 17,17-dioxide

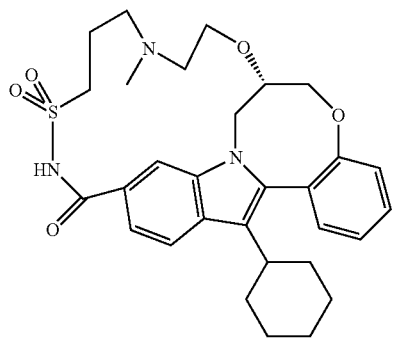

Step 1: N-benzyl-2-chloro-N-methylethanaminium chloride

2-[benzyl(methyl)amino]ethanol was added dropwise to an excess of $SOCl_2$ (50 eq.) and the mixture heated at 35° C. for 16 h. Volatiles were removed in vacuo and the residual oil triturated with $Et_2O$ to give the title compound as a white solid in quantitative yield. MS ($ES^+$) m/z 184 $(M+H)^+$; 186 $(M+H)^+$.

Step 2: N-benzyl-2-{[(7S)-11-carboxy-14-cyclohexyl-7,8-dihydro-6H-indolo[1,2-e][1,5]benzoxazocin-7-yl]oxy}-N-methylethanaminium chloride To a suspension of methyl (7S)-14-cyclohexyl-7-hydroxy-7,8-dihydro-6H-indolo[1,2-e][1,5]benzoxazocine-11-carboxylate (prepared as described in International patent application publication WO2006/046030) in toluene (0.05 M), were added 10 eq. of 30% w/w aq. NaOH followed by 0.25 eq. of tetrabutylammonium bromide. After stirring for 30 min, 2.5 eq. of N-benzyl-2-chloro-N-methylethanaminium chloride were added, and the reaction mixture was stirred at 60° C. for 16 h. The reaction mixture was concentrated in vacuo, and the residue purified by RP-HPLC (Waters XTerra prep. C18 column, 5um, 19×100 mm. Mobile phase: $MeCN/H_2O$ buffered with 0.1% TFA). Fractions containing the pure compound were combined and freeze dried in the presence of HCl to afford the title compound (25%) as a white powder. ($ES^+$) m/z 539 $(M+H)^+$.

Step 3: methyl(7S)-7-{2-[benzyl(methyl)amino]ethoxy}-14-cyclohexyl-7,8-dihydro-6H-indolo[1,2-e][1,5]benzoxazocine-11-carboxylate A solution (0.014 M) of N-benzyl-2-{[(7S)-11-carboxy-14-cyclohexyl-7,8-dihydro-6H-indolo[1,2-e][1,5]benzoxazocin-7-yl]oxy}-N-methylethanaminium chloride in anhydrous MeOH was treated with acetyl chloride (1.1 eq.). The mixture was heated at reflux overnight. All the volatiles were removed in vacuo to afford the title compound. The product was used in the next step without further purification. (ES+) m/z 553 (M+H)+.

Step 4: methyl(7S)-14-cyclohexyl-7-[2-(methylamino)ethoxy]-7,8-dihydro-6H-indolo[1,2-e][1,5]benzoxazocine-11-carboxylate To a solution (0.014 M) of methyl(7S)-7-{2-[benzyl(methyl)amino]ethoxy}-14-cyclo hexyl-7,8-dihydro-6H-indolo[1,2-e][1,5]benzoxazocine-11-carboxylate in anhydrous MeOH, Pd/C (1 eq.) was added and the resulting mixture was stirred for 12 h under an $H_2$ atmosphere. The mixture was filtered and then concentrated in vacuo to afford the title compound. The product was used in the next step without further purification. (ES+) m/z 463 (M+H)+.

Step 5: tert-butyl benzyl[(3-chloropropyl)sulfonyl]carbamate

Benzylamine (1 eq.) was dissolved in anhydrous DCM (0.5 M) and $Et_3N$ (1.1 eq.) was added; after cooling at 0° C., 1-chloro-3-propanesulfonyl chloride was slowly added and the mixture was stirred at RT for 20 h. All volatiles were evaporated in vacuo and the residue taken up with $Et_2O$; the precipitate was filtered off and the filtrate was concentrated; addition of PE afforded N-benzyl-3-chloropropane-1-sulfonamide as a white solid (87%). (ES+) m/z 248 (M+H+). Di-tert-butyl dicarbonate (1.5 eq.) was slowly added to an ice-cooled 0.45 M THF solution of N-benzyl-3-chloropropane-1-sulfonamide. DMAP (0.1 eq.) was then added and the reaction stirred overnight at RT. All volatiles were removed in vacuo and the crude diluted with EtOAc, washed with HCl, sat. aq. $NaHCO_3$ and brine. After drying over $Na_2SO_4$, all volatiles were evaporated in vacuo and the residual material used in the next step without purification. (ES+) m/z 348, 350 (M+H+).

Step 6: methyl(7S)-7-{2-[{3-[(benzylamino)sulfonyl]propyl}(methyl)amino]ethoxy}-14-cyclohexyl-7,8-dihydro-6H-indolo[1,2-e][1,5]benzoxazocine-11-carboxylate DIPEA (2 eq.), $K_2CO_3$ (4 eq.) and tert-butyl benzyl[(3-chloropropyl)sulfonyl]carbamate (was added to a solution of methyl (7S)-14-cyclohexyl-7-[2-(methylamino)ethoxy]-7,8-dihydro-6H-indolo[1,2-e][1,5]benzoxazocine-11-carboxylate (0.08 M) in MeCN. The mixture was heated in the microwave at 200° C. for 30 min. The resulting mixture was filtered, concentrated in vacuo, and the residue purified by RP-HPLC (WATERS XTERRA column, C18, 5 um, 19×150 mm. Mobile phase: MeCN/$H_2O$ buffered with 0.1% TFA). Fractions containing the pure compound were combined and freeze dried to afford the title compound (23%) as a white powder. (ES+) m/z 674 (M+H)+.

Step 7: (7S)-7-{2-[{3-[(benzylamino)sulfonyl]propyl}(methyl)amino]ethoxy}-14-cyclohexyl-7,8-dihydro-6H-indolo[1,2-e][1,5]benzoxazocine-11-carboxylic acid Sodium hydroxide (2 N, 6 eq.) was added to a solution of methyl(7S)-7-{2-[{3-[(benzylamino)sulfonyl]propyl}(methyl)amino]ethoxy}-14-cyclohexyl-7,8-dihydro-6H-indolo[1,2-e][1,5]benzoxazocine-11-carboxylate (0.025 M) in MeOH. The reaction was heated at 60° C. for 1 h prior to introducing further sodium hydroxide (2 N, 10 eq.) and continuing heating for 2 h. The mixture was then partitioned between $H_2O$ and EtOAc. The combined organics were washed with brine, dried ($Na_2SO_4$), filtered and concentrated in vacuo. The product was used in the next step without further purification. (ES+) m/z 660 (M+H)+.

Step 8: (7S)-16-benzyl-14-cyclohexyl-21-methyl-7,8-dihydro-6H-7,11-(epoxyethanoiminopropanothioiminomethano)indolo[1,2-e][1,5]benzoxazocin-15-one 17,17-dioxide DMAP (5 eq.) and EDC (1.5 eq.) were added to a solution of (7S)-7-{2-[{3-[(benzylamino)sulfonyl]propyl}(methyl)amino]ethoxy}-14-cyclo hexyl-7,8-dihydro -6H-indolo[1,2-e][1,5]benzoxazocine-11-carboxylic acid (6 mM) in a 1:1 mixture DCM/DMF. The reaction was stirred at 40° C. for 5 h. DCM was eliminated in vacuo and the remaining DMF solution used in the next step. (ES+) m/z 642 (M+H)+.

Step 9: (7S)-14-cyclohexyl-21-methyl-7,8-dihydro-6H-7,11-(epoxyethanoiminopropanothioiminomethano)indolo[1,2-e][1,5]benzoxazocin-15-one 17,17-dioxide The DMF solution of (7S)-16-benzyl-14-cyclohexyl-21-methyl-7,8-dihydro-6H-7,11-(epoxyethanoiminopropanothioiminomethano)indolo[1,2-e][1,5]benzoxazocin-15-one 17,17-dioxide from the previous step was diluted with anhydrous MeOH (0.015M), then Pd/C (1 eq) was added, and the resulting mixture was stirred for 12 h under a $H_2$ atmosphere. The reaction mixture was filtered and concentrated in vacuo. The residue was purified by RP-HPLC (WATERS SUNFIRE column, C18, 5 um, 19×100 mm. Mobile phase: MeCN/$H_2O$ buffered with 0.1% TFA). Fractions containing the pure compound were combined and freeze dried to afford the title compound (19%) as a white powder. The material was obtained as a 4:1* mixture of isomers* by 1H NMR. $^1H$ NMR (600 MHz, DMSO-$d_6$+TFA, 300 K) δ1.12-1.19 (m, 1H), 1.28-1.39 (m, 2H), 1.52-1.58 (m, 1H), 1.65-1.75 (m, 2H), 1.83-2.01 (m, 4H), 2.12-2.28 (m, 2H), 2.66-2.85 (m, 6H), 3.15-3.48 (m, 3H), 3.52-3.73 (m, 2H), 3.76-4.04 (m, 3H), 4.06-4.32 (m, 2H), 4.48-4.56* and 4.85-4.89 (m, 1H), 7.18-7.32 (m, 2H), 7.33-7.58 (m, 3H), 7.86 and 7.95* (d, J 8.4, 1H), 8.32 and 8.43* (bs, 1H); (ES+) m/z 552 (M+H)+.

EXAMPLE 10

13-cyclohexyl-5,20,23-trimethyl-6,7-dihydro-5H-10,6-(methanoiminothiopropanoiminoethanoiminomethano)indolo[1,2-d][1,4]benzodiazepin-14-one 16,16-dioxide

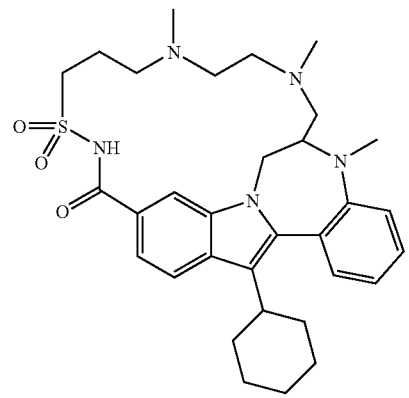

Step 1: tert-butyl benzyl[(3-chloropropyl)sulfonyl]carbamate

Benzylamine (1 eq.) was dissolved in anhydrous DCM (0.5M) and Et$_3$N (1.1 eq.) was added; after cooling at 0° C., 1-chloro-3-propanesulfonyl chloride was slowly added and the mixture was stirred at RT for 20 h. All volatiles were evaporated in vacuo and the residue taken up with Et$_2$O; the precipitate was filtered off and the filtrate was concentrated; addition of PE afforded N-benzyl-3-chloropropane-1-sulfonamide as a white solid (87%). MS (ES$^+$): 248 (M+H$^+$). Di-tert-butyl dicarbonate (1.5 eq.) was slowly added to an ice-cooled 0.45 M THF solution of N-benzyl-3-chloropropane-1-sulfonamide. DMAP (0.1 eq.) was then added and the reaction stirred overnight at RT. All volatiles were removed in vacuo and the crude diluted with EtOAc, washed with HCl, sat. aq. NaHCO$_3$ and brine. After drying over Na$_2$SO$_4$, all volatiles were evaporated in vacuo and the residual material used in the next step without purification. (ES$^+$) m/z 348, 350 (M+H$^+$).

Step 2: tert-butyl benzyl[(3-{methyl[2(methylamino)ethyl]amino}propyl)sulfonyl]carbamate Tert-butyl benzyl[(3-chloropropyl)sulfonyl]carbamate was dissolved in MeCN (0.2M) and N,N'-dimethylethane-1,2-diamine (5 eq.) was added followed by K$_2$CO$_3$ (5 eq.). The mixture was stirred at 65° C. overnight. The solvent was removed under reduced pressure and the residual material was dissolved in EtOAc and washed with water. After drying over Na$_2$SO$_4$, all volatiles were evaporated in vacuo and the residual material used in the next step without purification. (ES$^+$) m/z 400 (M+H)$^+$.

Step 3: tert-butyl[(3-{methyl[2(methylamino)ethyl]amino}propyl)sulfonyl]carbamate Pearlman's catalyst (0.10 eq.) was suspended in a 0.35 M EtOH solution of tert-butyl benzyl[(3-{methyl[2(methylamino)ethyl]amino}propyl)sulfonyl]carbamate and the mixture was stirred under an hydrogen atmosphere for 4h. The crude was filtered on a CELITE pad and washed with EtOH; after evaporation of the solvent the product was obtained as white solid which was used without further characterisation (98% yield, two steps). (ES$^+$) m/z 310 (M+H)$^+$.

Step 4: dimethyl 13-cyclohexyl-6,7-dihydro-5H-indolo[1,2-d][1,4]benzodiazepine-6,10-dicarboxylate Methyl 2-bromo-3-cyclohexyl-indole-6-carboxylate (prepared as described in International patent application publication WO2006/046030), 2-(4,4,5,5-tetramethyl-1,3,2-dioxaborolan-2-yl)aniline (1.4 eq.) and Pd(PPh$_3$)$_2$Cl$_2$ (0.1 eq.) were dissolved in dioxane (0.08M) and 2M Na$_2$CO$_3$ solution (1 eq.) was added. The mixture was degassed and flushed with Ar. The mixture was heated to 100° C. under Ar atmosphere. After 6 h the mixture was cooled to RT, and all volatiles were evaporated in vacuo. The residual material was dissolved in DCM, and PE was added. The mixture was left stirring for 3 days. The resulting precipitate was filtered off and dissolved again in DCM. The product methyl-2-(2-aminophenyl)-3-cyclohexyl-1H-indole-6-carboxylate was precipitated from this solution with PE and obtained after filtration and drying in vacuo as a beige powder (68%). (ES$^+$) m/z 349 (M+H)$_+$.

The foregoing compound was dissolved in MeCN (0.07 M) and Bu$_4$NBr (0.3 eq.) was added followed by K$_2$CO$_3$ (6 eq.). Ethyl α-chloroacrylate (1.7 eq.) was added to the mixture which was then heated overnight to 60° C. All volatiles were evaporated in vacuo and the residual material was mixed with EtOAc. The suspension was extracted with 10% citric acid, sat. aq. NaHCO$_3$ and brine. After drying over Na$_2$SO$_4$ all volatiles were evaporated in vacuo. The residual material was subjected to purification by flash chromatography (PE, then PE:EtOAc, 9:1; then PE:EtOAc, 8:2). After evaporation of the solvents the product was obtained as a yellowish solid (84%). (ES$^+$) m/z 433 (M+H)$^+$.

Step 5: Dimethyl 13-cyclohexyl-5-methyl-6,7-dihydro-5H-indolo[1,2-d][1,4]benzodiazepine-6,10-dicarboxylate Dimethyl 13-cyclohexyl-6,7-dihydro-5H-indolo[1,2-d][1,4]benzodiazepine-6,10-dicarboxylate was dissolved in anhydrous MeOH (0.05M) and HOAc was added. the mixture was treated with a 37% solution of formaldehyde in water (1.2 eq.), then NaCNBH$_3$ (1.2 eq.) was added. The solution was stirred for 2 h at RT. The product was isolated by flash chromatography (PE:EtOAc, 9:1, 0.5% NEt$_3$). After evaporation of the solvents a colourless solid was obtained (quant.). (ES$^+$) m/z 447 (M+H)$^+$.

Step 6: Methyl 13-cyclohexyl-6-(hydroxymethyl)-5-methyl-6,7-dihydro-5H-indolo[1,2-d][1,4]benzodiazepine-10-carboxylate Dimethyl 13-cyclohexyl-5-methyl-6,7-dihydro-5H-indolo[1,2-d][1,4]benzodiazepine-6,10-dicarboxylate was dissolved in anhydrous THF (0.05M) and LiBH$_4$ (1 eq.) was added. The mixture was stirred at RT. After 1 h only marginal conversion to the product was observed. BH$_3$.THF complex (1 eq.) was added and the mixture was stirred at RT. After 2h a further equivalent of BH$_3$.THF complex was added and the mixture was stirred for 2 h. The mixture was quenched by addition of silica gel and all volatiles were evaporated in vacuo. The product was isolated by flash chromatography (PE:EtOAc, 8:2). After evaporation of the solvents the product was obtained as a colourless solid (80%). (ES$^+$) m/z 419 (M+H)$^+$.

Step 7: Methyl 13-cyclohexyl-6-formyl-5-methyl-6,7-dihydro-5H-indolo[1,2-d][1,4]benzodiazepine-10-carboxylate DMSO (5 eq.) was dissolved in DCM and the solution was cooled to −78° C. At this temperature a 2 M solution of oxalylchloride in DCM (2.5 eq.) was added slowly and the mixture was stirred for 25 min at −78° C. A solution of dimethyl 13-cyclohexyl-5-methyl-6,7-dihydro-5H-indolo[1,2-d][1,4]benzodiazepine-6,10-dicarboxylate (1 eq.) in DCM (0.09 M) was added slowly at −78° C. and stirring was continued for 25 min at this temperature. Then NEt$_3$ (8 eq.) was added and the resulting slurry was placed into an ice bath at 0° C. The mixture was left stirring for 90 min, then diluted with DCM and extracted with sat. aq. NH$_4$Cl, sat. aq. NaHCO$_3$ and brine. After drying over Na$_2$SO$_4$ all volatiles were evaporated in vacuo. The product was obtained as a deep-yellow solid, which was filtered with DCM over a pad of silica. After evaporation of the solvent the product was obtained as a yellowish solid (quant.). (ES$^+$) m/z 417 (M+H)$^+$.

Step 8: methyl 13-cyclohexyl-5-methyl-6-(2,5,13,13-tetramethyl-9,9-dioxido-11-oxo-12-oxa-9-thia-2,5,10-triazatetradec-1-yl)-6,7-dihydro-5H-indolo[1,2-d][1,4]benzodiazepine-10-carboxylate Methyl 13-cyclohexyl-6-formyl-5-methyl-6,7-dihydro-5H-indolo[1,2-d][1,4]benzodiazepine-10-carboxylate was dissolved in MeOH (0.08 M) and HOAc was added. Tert-butyl[(3-{methyl[2(methylamino)ethyl]amino}propyl)sulfonyl]carbamate (1.5 eq. prepared as described in Example 15, Steps 1-3) was added and the mixture was stirred for 5 min. NaCNBH$_3$ (1.5 eq.) was added and the mixture was stirred for 6 h. All volatiles were evaporated and the residual material was dissolved in EtOAc. The solution was extracted with sat. aq. NH$_4$Cl, sat. aq. NaHCO$_3$ and brine. After drying over Na$_2$SO$_4$ all volatiles were evaporated in vacuo. A yellow amorphous solid was obtained which was used without further purification in the next reaction (60%). (ES$^+$) m/z 711 (M+H)$^+$.

Step 9: 6-{[{2-[[3-(aminosulfonyl)propyl](methyl)amino]ethyl}(methyl)amino]methyl}-13-cyclohexyl-5-methyl-6,7-dihydro-5H-indolo[1,2-d][1,4]-benzodiazepine-10-carboxylic acid Methyl 13-cyclohexyl-5-methyl-6-(2,5,13,13-tetramethyl-9,9-dioxido-11-oxo-12-oxa-9-thia-2,5,10-triazatetradec-1-yl)-6,7-dihydro-5H-indolo[1,2-d][1,4]benzodiazepine-10-carboxylate was dissolved in DCM (0.05M) and TFA was added. The mixture was left standing at RT. After 1 h all volatiles were evaporated in vacuo. The residual material was coevaporated with toluene. Methyl 6-{[{2-[[3-(aminosulfonyl)propyl]-(methyl)amino]ethyl}(methyl)amino]methyl}-13-cyclohexyl-5-methyl-6,7-dihydro-5H-indolo[1,2-d][1,4]benzodiazepine-10-carboxylate was obtained as a reddish sticky solid. The material was dissolved in MeOH/THF (0.05 M) and 1M aqueous KOH solution (4 eq.) was added. The mixture was stirred at RT overnight and then warmed for 5 h to 70° C. After cooling to RT the solution was diluted with water and adjusted with 1M aqueous HCl to pH 6. The resulting suspension was extracted with EtOAc. The combined organic phases were washed with brine and dried over Na$_2$SO$_4$. All volatiles were evaporated in vacuo. The residual material was used without further purification in the next reaction (95%). (ES$^+$) m/z 611 (M+H)$^+$.

Step 10: 13-cyclohexyl-5,20,23-trimethyl-6,7-dihydro-5H-10,6-(methanoiminothiopropanoiminoethanoiminomethano)indolo[1,2-d][1,4]-benzodiazepin-14-one 16,16-dioxide 6-{[{2-[[3-(aminosulfonyl)propyl](methyl)amino]ethyl}(methyl)amino]methyl}-13-cyclohexyl-5-methyl-6,7-dihydro-5H-indolo[1,2-d][1,4]benzodiazepine-10-carboxylic acid was dissolved in DCM (2.5 mM). DMAP (3 eq.) and EDC (2 eq.) were added and the solution was stirred overnight. The solution was extracted with sat. aq. NH$_4$Cl, sat. aq. NaHCO$_3$ and brine. After drying over Na$_2$SO$_4$ all volatiles were evaporated in vacuo. The yellow residue was subjected to mass-guided prep. RP-HPLC. After lyophilisation of the product fractions the product was obtained as a yellowish amorphous solid (18%). $^1$H NMR (400 MHz, DMSO-d$_6$, 300 K, TFA-salt) δ 8.23 (s, 1H), 7.93 (d, 1H, J 8.36), 7.54 (d, 1H, J 8.36), 7.45-7.43 (m, 1H), 7.33-7.16 (m, 3H), 4.66 (d, 1H, J 14.52), 3.93 (d, 1H, J 14.52), 3.75-3.66 (m, 2H), 3.54-3.21 (m, 5H), 2.81-2.65 (m, 8H), 2.45-2.36 (m, 2H), 2.19-1.70 (m, 11H), 1.54-1.18 (m, 6H); (ES$^+$) m/z 578 (M+H)$^+$.

EXAMPLE 11

13-cyclohexyl-20,23-dimethyl-6,7-dihydro-5H-6,10-(epiminoethanoiminopropanothioiminomethano)indolo[2,1-a][2]benzazepin-14-one 16,16-dioxide

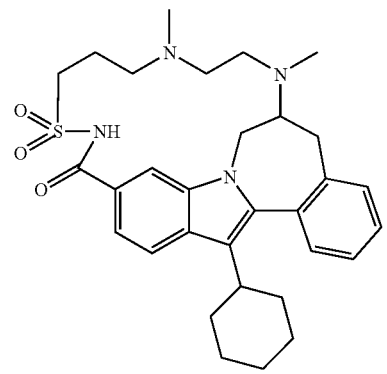

Step 1: methyl 13-cyclohexyl-6-[methyl(3,11,11-trimethyl-7,7-dioxido-9-oxo-10-oxa-7-thia-3,8-diazadodec-1-yl)amino]-6,7-dihydro-5H-indolo[2,1-a][2]benzazepine-10-carboxylate Zinc chloride (2 eq.) was added to a stirred mixture of methyl 13-cyclohexyl-6-oxo-6,7-dihydro-5H-indolo[2,1-a][2]benzazepine-10-carboxylate (1 eq.; WO 2006/046039, Example 5, Step 4) and tert-butyl[(3-{methyl[2-(methylamino)ethyl]amino}propyl)-sulfonyl]carbamate (2.5 eq.; Example 15, Steps 1-3) in anhydrous MeOH, and the mixture was stirred at 70° C. for 2 h. NaCNBH$_3$ (2.3 eq.) was added and the mixture was stirred at 60° C. overnight. All volatiles were evaporated and the residual material was dissolved in EtOAc and washed with brine. After drying over Na$_2$SO$_4$ all volatiles were evaporated in vacuo. Flash chromatography (PE/EtOAc+10% MeOH and 0.5% NEt$_3$ 1:1 to EtOAc+20% MeOH+1% NEt$_3$) afforded 43% of the title compound and 27% of the corresponding methyl carbamate (methyl 13-cyclohexyl-6-[methyl(3-methyl-7,7-dioxido-9-oxo-10-oxa-7-thia-3,8-diazaundec-1-yl)amino]-6,7-dihydro-5H-indolo[2,1-a][2]benzazepine-10-carboxylate). (ES$^+$) m/z 681 (M+H)$^+$.

Step 2: 6-[{2-[[3-(aminosulfonyl)propyl](methyl)amino]ethyl}(methyl)amino]-13-cyclohexyl-6,7-dihydro-5H-indolo[2,1-a][2]benzazepine-10-carboxylic acid Methyl 13-cyclohexyl-6-[methyl(3,11,11-trimethyl-7,7-dioxido-9-oxo-10-oxa-7-thia-3,8-diazadodec-1-yl)amino]-6,7-dihydro-5H-indolo[2,1-a][2]benzazepine-10-carboxylate was dissolved in DCM/TFA 3:1 (0.03M) and the mixture was left standing at RT. After 45 min all volatiles were evaporated in vacuo. The residue was dissolved in MeOH (0.07M) and 1M aqueous KOH solution (9 eq.) was added. The mixture was stirred at 65° C. for 4h. After cooling to 0° C. the pH of the solution was adjusted with 1 M aqueous HCl to pH 6. The resulting suspension was extracted with EtOAc. The combined organic phases were washed with brine and dried over Na$_2$SO$_4$. All volatiles were evaporated in vacuo. The residual material was used without further purification in the next reaction. (ES$^+$) m/z 567 (M+H)$^+$.

Step 3: 13-cyclohexyl-20,23-dimethyl-6,7-dihydro-5H-6,10-(epiminoethanoiminopropan-othioiminomethano)indolo[2,1-a][2]benzazepin-14-one 16,16-dioxide 6-[{2-[[3-(Aminosulfonyl)propyl](methyl)amino]ethyl}(methyl)amino]-13-cyclohexyl-6,7-dihydro-5H-indolo[2,1-a][2]benzazepine-10-carboxylic acid was dissolved in DCM (2.5 mM). DMAP (3 eq.) and EDC (1.5 eq.) were added and the solution was stirred at 40° C. for 45 min. The residue obtained after evaporation of volatiles was purified by mass-guided prep. RP-HPLC. After lyophilisation of the fractions the title compound was obtained as a white solid (15%). $^1$H NMR (400 MHz, DMSO-d$_6$, 300 K, bis TFA-salt) δ 8.29 (s, 1H), 8.01 (d, 1H, J 8.4), 7.46-7.60 (m, 5H), 4.99 (d, 1H, J 17.2), 4.19 (b.s, 1H), 3.99 (dd, 1H, J 4.8, 17.2), 3.79 (bs., 2H), 3.64-3.36 (m, 3H), 3.48-3.40 (m, 2H), 3.33-3.22 (m, 2H), 2.90-2.86 (m, 1H), 2.89 (s, 3H), 2.86 (s, 3H), 2.31-2.22 (m, 1H), 2.15-1.90 (m, 5H), 1.87 (b.s, 1H), 1.76-1.71 (m, 2H), 1.57 (d, 1H, J 10.8), 1.41 (bs, 2H), 1.23-1.18 (m, 1H); (ES$^+$) m/z 549 (M+H)$^+$.

EXAMPLE 12

8-cyclohexyl-19,22-dimethyl-1,12b-dihydro-5,1a-(methanoiminothiopropanoimino-ethanoiminomethano)cyclopropa[d]indolo[2,1-a][2]benzazepin-13-one 15,15-dioxide

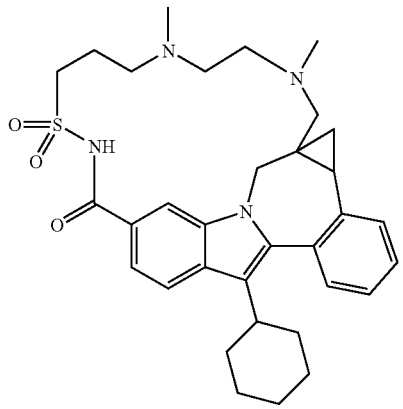

Step 1: Dimethyl 8-cyclohexyl-1,12b-dihydrocyclopropa[d]indolo[2,1-a][2]benzazepine-1a,5(2H)-dicarboxylate The compound was prepared according to US 2007/0060565 A1 but instead of heating at 50° C. overnight the mixture was stirred at RT for 2 h. The mixture was diluted with EtOAc and washed with water. The crude was then extracted twice with EtOAc and twice with DCM, dried over Na$_2$SO$_4$, filtered and concentrated. The residual material was subjected to flash chromatography (PE:EtOAc, 3:1). After evaporation of the solvent the product was obtained as yellow solid (46%). (ES$^+$) m/z 444 (M+H)$^+$.

Step 2: Methyl 8-cyclohexyl-1a-(hydroxymethyl)-1,1a,2,12b-tetrahydrocyclopropa[d]indolo[2,1-a][2]benzazepine-5-carboxylate Dimethyl 8-cyclohexyl-1,12b-dihydrocyclopropa[c]indolo[2,1-a][2]benzazepine-1a,5(2H)-dicarboxylate was dissolved in anhydrous THF (0.02 M) and after cooling at 0° C. BH$_3$.THF complex (1.5 eq.) was added followed by LiBH$_4$ (1.5 eq.) and water (4 eq.). The mixture was stirred at RT for 4h then water was slowly added. The crude was extracted twice with EtOAc, dried over Na$_2$SO$_4$, filtered and all volatiles were removed in vacuo. The residual material was subjected to flash chromatography (PE:EtOAc, 2:1). After evaporation of the solvent the product was obtained as white solid (75%). (ES$^+$) m/z 416 (M+H)$^+$.

Step 3: Methyl 8-cyclohexyl-1a-formyl-1,1a,2,12b-tetrahydrocyclopropa[d]indolo[2,1-a][2]benzazepine-5-carboxylate DMSO (5 eq.) was dissolved in DCM and the solution was cooled to −78° C. At this temperature a 2M solution of oxalylchloride in DCM (2.5 eq.) was added slowly and the mixture was left stirring for 25 min at −78° C. A solution of methyl 8-cyclohexyl-1a-(hydroxymethyl)-1,1a,2,12b-tetrahydrocyclopropa[c]indolo[2,1-a][2]benzazepine-5-carboxylate (1 eq.) in DCM (0.09M) was added slowly at −78° C. and stirring was continued for 25 min at this temperature. Then NEt$_3$ (8 eq.) was added and the resulting slurry was placed into an ice bath at 0° C. The mixture was stirred for 90 min, then diluted with DCM and extracted with water, HCl 1N, sat. aq. NaHCO$_3$ and brine. After drying over Na$_2$SO$_4$ all volatiles were evaporated in vacuo. After evaporation of the solvent the product was obtained as a yellowish solid (quant.). (ES$^+$) m/z 414 (M+H)$^+$.

Step 4: Methyl 8-cyclohexyl-1a-(2,5,13,13-tetramethyl-9,9-dioxido-11-oxo-12-oxa-9-thia-2,5,10-triazatetradec-1-O-1,1a,2,12b-tetrahydrocyclopropa[d]indolo[2,1-a][2]benzazepine-5-carboxylate Methyl 8-cyclohexyl-1a-formyl-1,1a,2,12b-tetrahydrocyclopropa[c]indolo[2,1-a][2]benzazepine-5-carboxylate was dissolved in DCE (0.08M) and HOAc (3.5 eq.) was added. Tert-butyl[(3-{methyl[2(methylamino)ethyl]amino}propyl)sulfonyl]carbamate (3 eq., Example 18, Steps 1-3) was added and the mixture was stirred for 5 min then after the addition of NaBH(OAc)$_3$ (3 eq.) stirring was continued for 18 h. All volatiles were evaporated in vacuo and the residual material was dissolved in EtOAc. The solution was extracted with sat. aq. NaHCO$_3$, water and brine. After drying over Na$_2$SO$_4$ all volatiles were evaporated in vacuo and the residual material was subjected to flash chromatography (EtOAc:MeOH 4:1, 1% Et$_3$N). After evaporation of the solvent the product was obtained as white solid (30%). (ES$^+$) m/z 707 (M+H)$^+$.

Step 5: 1a-{[{2-[[3-(aminosulfonyl)propyl](methyl)amino]ethyl}(methyl)amino]methyl}-8-cyclohexyl-1,1a,2,12b-tetrahydrocyclopropa[d]indolo[2,1-a][2]benzazepine-5-carboxylic acid Methyl 8-cyclohexyl-1a-(2,5,13,13-tetramethyl-9,9-dioxido-11-oxo-12-oxa-9-thia-2,5,10-triazatetradec-1-yl)-1,1a,2,12b-tetrahydrocyclopropa[d]indolo[2,1-a][2]benzazepine-5-carboxylate was dissolved in DCM (0.05M) and TFA (50 eq.) was added. After stirring at RT for 2 h all volatiles were evaporated in vacuo and the residual material was coevaporated three times with toluene. (MS (ES+): 607.6). The material was dissolved in MeOH (0.05M) and 1 M KOH solution (10 eq.) was added and the mixture was stirred at 70° C. for 3 h. After cooling, 1N hydrochloric acid was slowly added until neutral pH. The crude was extracted twice with EtOAc, washed with water and brine. After drying the organic phase over $Na_2SO_4$ all volatiles were evaporated in vacuo. The residual material was used without further purification in the next reaction. $(ES^+)$ m/z 593 $(M+H)^+$.

Step 6: 8-cyclohexyl-19,22-dimethyl-1,12b-dihydro-5,1a-(methanoiminothiopropanoimino-ethanoiminomethano)cyclopropa[d]indolo[2,1a][2]benzazepin-13-one 15,15-dioxide 1a-{[{2-[[3-(aminosulfonyl)propyl](methyl)amino]ethyl}(methyl)amino]methyl}-8-cyclohexyl-1,1a,2,12b-tetrahydrocyclopropa[c/]indolo[2,1-a][2]benzazepine-5-carboxylic acid was dissolved in DCM (0.04M). DMAP (3 eq.) and EDC (2 eq.) were added and the solution was stirred at 40° C. for 3 h and then at RT overnight. All volatiles were evaporated in vacuo and the yellow residue was subjected to mass-guided prep. RP-HPLC. After lyophilisation the product was obtained as a white amorphous solid (18%, mixture of diasteroisomers 2.5:1). δ H NMR (400 MHz, DMSO-$d_6$, 300 K, TFA-salt) δ 8.39 (s, 1H), 7.96-7.93 (m, 1H), 7.62-7.55 (m, 2H, J 8.36), 7.48-7.33 (m, 3H), 5.07-4.97 (m, 1H), 3.70-3.62 (m, 3H), 3.53-3.07 (m, 9H), 2.97-2.79 (m, 4H), 2.76-2.67 (m, 6H), 2.21-1.70 (m, 7H), 1.56-1.53 (m, 3H), 1.24-1.23 (m, 1H); $(ES^+)$ m/z 575 $(M+H)^+$.

EXAMPLE 13

13-cyclohexyl-20,23-dimethyl-6,7-dihydro-5H-10,6-(methanoiminothiopropanoimino-ethanoiminomethano)indolo[2,1-a][2]benzazepin-14-one 16,16-dioxide

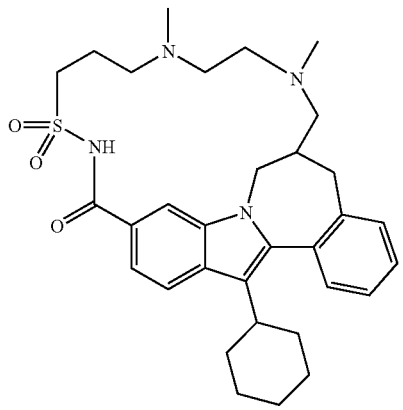

Step 1: Methyl 13-cyclohexyl-6-(hydroxymethyl)-6,7-dihydro-5H-indolo[2,1-a][2]benzazepine-10-carboxylate Dimethyl 13-cyclohexyl-6,7-dihydro-5H-indolo[2,1-a][2]benzazepine-6,10-dicarboxylate (prepared according to International patent application publication WO 2006/020082) was dissolved in anhydrous THF (0.02 M) and after cooling at 0° C. $BH_3$THF complex (1.5 eq.) was added followed by $LiBH_4$ (1 eq.) and water (4 eq.). The mixture was left stirring at RT for 2h, then 1N hydrochloric acid was slowly added. The crude was extracted twice with EtOAc, dried over $Na_2SO_4$, filtered, and all volatiles were removed in vacuo to obtain desired compound as a yellow solid (85%) that was used in the next step without purification. $(ES^+)$ m/z 404 $(M+H)^+$.

Step 2: Methyl 13-cyclohexyl-6-formyl-6,7-dihydro-5H-indolo[2,1-a][2]benzazepine-10-carboxylate DMSO (5 eq.) was dissolved in DCM and the solution was cooled to −78° C. At this temperature a 2M solution of oxalylchloride in DCM (2.5 eq.) was added slowly and the mixture was left stirring for 25 min at −78° C. A solution of methyl 13-cyclohexyl-6-(hydroxymethyl)-6,7-dihydro-5H-indolo[2,1-a][2]benzazepine-10-carboxylate (1 eq.) in DCM (0.09M) was added slowly at −78° C. and stirring was continued for 25 min at this temperature. Then $NEt_3$ (8 eq.) was added and the resulting slurry was placed into an ice bath at 0° C. The mixture was stirred for 90 min, then diluted with DCM and extracted with water, HCl 1N, sat. aq. $NaHCO_3$ and brine. After drying over $Na_2SO_4$ all volatiles were evaporated in vacuo. After evaporation of the solvent the product was obtained as a yellowish solid (quant.). $(ES^+)$ m/z 402 $(M+H)^+$.

Step 3: Methyl 13-cyclohexyl-6-(2,5,13,13-tetramethyl-9,9-dioxido-11-oxo-12-oxa-9-thia-2,5,10-triazatetradec-1-yl)-6,7-dihydro-5H-indolo[2,1-a][2]benzazepine-10-carboxylate Methyl 13-cyclohexyl-6-formyl-6,7-dihydro-5H-indolo[2,1-a][2]benzazepine-10-carboxylate was dissolved in MeOH (0.04 M), HOAc (5 eq.) and tert-butyl[(3-{methyl[2-(methylamino)ethyl]amino}propyl)sulfonyl]carbamate (2 eq. Example 15, steps 1-3) were added followed by $Et_3N$ (3 eq.) and the mixture was stirred for 5 min. $NaCNBH_3$ (2 eq.) was added and the mixture was stirred for 18 h. All volatiles were evaporated and the residual material was dissolved in EtOAc. The solution was extracted with sat. aq. $NaHCO_3$, water and brine. After drying over $Na_2SO_4$ all volatiles were evaporated in vacuo and the compound was used without purification in the next reaction. (ES) m/z 697 $(M+H)^+$.

Step 4: 6-{[{2-[[3-(aminosulfonyl)propyl](methyl)amino]ethyl}(methyl)amino]methyl}-13-cyclohexyl-6,7-dihydro-5H-indolo[2,1-a][2]benzazepine-10-carboxylic acid Methyl 13-cyclohexyl-6-(2,5,13,13-tetramethyl-9,9-dioxido-11-oxo-12-oxa-9-thia-2,5,10-triazatetradec-1-yl)-6,7-dihydro-5H-indolo[2,1-a][2]benzazepine-10-carboxylate was dissolved in DCM (0.1 M) and TFA (44 eq.) was added. After stirring at RT for 1 h all volatiles were evaporated in vacuo and the residual material was coevaporated three times with toluene. (MS (ES+): 595.6). The material was dissolved in MeOH (0.05 M) and 1 M KOH solution (10 eq.) was added and the mixture was stirred at 70° C. for 3 h. After cooling 1N hydrochloric acid was slowly added until neutral pH. The mixture was extracted three times with EtOAc, washed with water and brine. After drying the organic phase over $Na_2SO_4$ all volatiles were evaporated in vacuo. The residual material was used without further purification in the next reaction. $(ES^+)$ m/z 581 $(M+H)^+$.

Step 5: 13-cyclohexyl-20,23-dimethyl-6,7-dihydro-5H-10,6-(methanoiminothiopropanoimino-ethanoiminomethano)indolo[2,1-a][2]benzazepin-14-one 16,16-dioxide 6-{[{2-[[3-(Aminosulfonyl)propyl](methyl)amino]ethyl}(methyl)amino]methyl}-13-cyclohexyl-6,7-dihydro-5H-indolo[2,1-a][2]benzazepine-10-carboxylic acid was dissolved in DCM (0.04 M). DMAP (3 eq.) and EDC (2 eq.) were added and the solution was stirred at 40° C. for 1 h. All volatiles were evaporated in vacuo and the yellow residue was subjected to mass-guided prep. RP-HPLC. After lyophilisation the product was obtained as a white amorphous solid (11%). $^1$H NMR (400 MHz, DMSO-d$_6$, 300 K, TFA-salt) δ 8.22 (s, 1H), 7.94 (d, 1H, J 8.33), 7.54-7.47 (m, 5H, J 8.36), 4.53 (d, 1H, J 15.66), 3.73-3.79 (m, 1H), 3.57-3.53 (m, 4H), 3.47-3.44 (m, 2H), 3.34-3.26 (m, 2H), 3.18-3.15 (m, 1H), 2.91-2.82 (m, 10H), 2.21-1.87 (m, 8H), 1.77-1.72 (m, 2H), 1.52-1.36 (m, 2H), 1.23-1.17 (m, 1H); (ES$^+$) m/z 563 (M+H)$^+$.

The following tables show four of these examples and compounds made in a similar manner:

TABLE 1

16 membered macrocycles

| Example no. | Compound name | Structure | procedure | m/z (ES$^+$) |
|---|---|---|---|---|
| 3≡101 | (7R)-14-cyclohexyl-21,24-dimethyl-7,8-dihydro-6H-7,11-(epiminoethanoiminopropano-thioiminomethano)indolo[1,2-e][1,5]benzoxazocin-15-one 17,17-dioxide | (structure) | A, B | 565 |
| 2≡102 | (7R)-14-cyclohexyl-24-methyl-7,8-dihydro-6H-7,11-(epiminoethanoiminopropano-thioiminomethano)indolo[1,2-e][1,5]benzoxazocin-15-one 17,17-dioxide | (structure) | A | 551 |
| 6≡103 | (7R)-14-cyclohexyl-20,24-dimethyl-7,8-dihydro-6H-7,11-(epiminopropanoiminoethano-thioiminomethano)indolo[1,2-e][1,5]benzoxazocin-15-one 17,17-one | (structure) | C, B | 565 |

TABLE 2 macrocycles

| Example no. | Compound name | Structure | procedure | m/z (ES+) |
|---|---|---|---|---|
| 1≡201 | (7R)-14-cyclohexyl-25-methyl-7,8-dihydro-6H-7,11-(epiminoethanoiminobutano-thioiminomethano)indolo[1,2-e][1,5]benzoxazocine-15,21-dione 17,17-dioxide | | A | 579 |

TABLE 3

2-Fluorocyclohexyl macrocycles

| Example no. | Compound name | Structure | procedure | m/z (ES+) |
|---|---|---|---|---|
| 4≡301 | (7R)-14-[(1R,2S) or (1S,2R)-2-fluorocyclohexyl]-21,24-dimethyl-7,8-dihydro-6H-7,11-(epiminoethanoiminopropano-thioiminomethano)indolo[1,2-e][1,5]benzoxazocin-15-one 17,17-dioxide | | A, B | 583 |

TABLE 4

Various macrocycles

| Example no. | Compound name | Structure | procedure | m/z (ES+) |
|---|---|---|---|---|
| 401 | (7R)-14-cyclohexyl-3-fluoro-21,24-dimethyl-7,8-dihydro-6H-7,11-(epiminoethanoimino-propanothioiminomethano)indolo[1,2-e][1,5]benzoxazocin-15-one 17,17-dioxide | 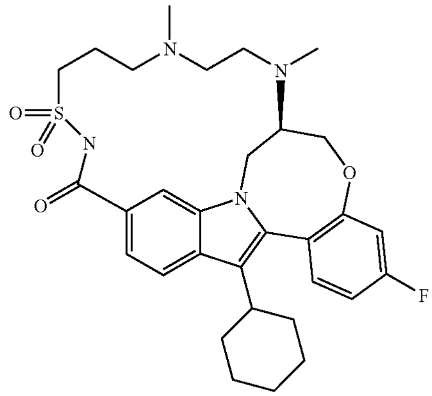 | C | 583 |
| 402 | (7R)-14-cyclohexyl-2-fluoro-21,24-dimethyl-7,8-dihydro-6H-7,11-(epiminoethanoimino-propanothioiminomethano)indolo[1,2-e][1,5]benzoxazocin-15-one 17,17-dioxide | 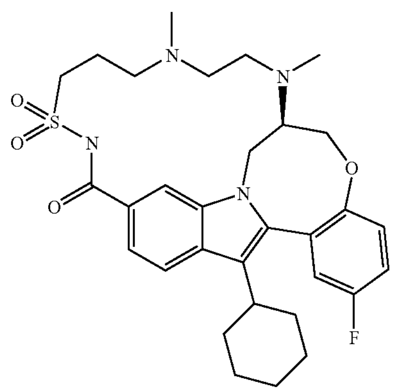 | C | 583 |

EXAMPLE 14

16-cyclohexyl-3,6-dimethyl-17-phenyl-4,5,6,7,8,9-hexahydro-1H-13,15-(ethanediylidene)pyrrolo[2,1-f][1,2,7,10,13]thiatetraazacyclohexadecine-2,12(3H)-dione 10,10-dioxide

Step 1: methyl 2-bromo-1-(2-tert-butoxy-2-oxoethyl-3-cyclohexyl-1H-indole-6-carboxylate A solution of methyl 2-bromo-3-cyclohexyl-1H-indole-6-carboxylate (prepared as described in published International patent application publication WO2006/046030, from commercially available methyl indole-6-carboxylate) in DMF (0.1 M) was treated with NaH (60% dispersion in mineral oil) (2 eq) at 0° C. The reaction was allowed to reach RT under a nitrogen atmosphere. Then tert-butyl-bromoacetate (3 eq) was added and the reaction was heated to 60° C. for 3h. The reaction mixture was allowed to cool to RT, diluted with EtOAc and washed with an aqueous solution of HCl (1N), brine and dried over $Na_2SO_4$ before being filtered and the solvent volume reduced in vacuo. The product precipitated from the residual solvent. The solid was collected and dried in vacuo to afford the title compound (95%). (ES+) m/z 450 (M+H)+, 452 (M+H)+

Step 2: methyl 1-(2-tert-butoxy-2-oxoethyl)-3-cyclohexyl-2-phenyl-1H-indole-6-carboxylate To a solution of methyl 2-bromo-1-(2-tert-butoxy-2-oxoethyl)-3-cyclohexyl-1H-indole-6-carboxylate in dioxane (0.06 M) was added bis(triphenylphosphine)palladium(II) dichloride (0.2 eq) at RT under a nitrogen atmosphere. Then aqueous $Na_2CO_3$ (2 M; 4 eq) followed by phenylboronic acid (2.5 eq) were added and the reaction was heated to 80° C. for 2 h. The reaction mixture was allowed to cool and concentrated in vacuo. DCM was added and the organic phase washed with $H_2O$, brine and dried over $Na_2SO_4$ before being filtered and concentrated in vacuo. The crude material was purified by automated FC ($SiO_2$; 95:5 EtOAc/PE) to afford the title compound (88%). (ES+) m/z 448 (M+H)+

Step 3: [3-cyclohexyl-6-(methoxycarbonyl)-2-phenyl-1H-indol-1-yl]acetic acid To methyl 1-(2-tert-butoxy-2-oxo ethyl)-3-cyclo hexyl-2-phenyl-1H-indole-6-carboxylate in DCM/$H_2O$ (2:1; 0.15 M), TFA (>300 eq) were added at RT and the reaction left stirring for 1 h. The volatiles were removed in vacuo, and the residue diluted with DCM. The organic phase was washed with brine, dried over $Na_2SO_4$, filtered and the solvent evaporated in vacuo to afford the title compound (98%). (ES+) m/z 392 (M+H)+

Step 4: methyl 1-{2-[{2-[(tert-butoxycarbonyl)(methyl)amino]ethyl}(methyl)amino]-2-oxoethyl}-3-cyclohexyl-2-phenyl-1H-indole-6-carboxylate To a solution of [3-cyclohexyl-6-(methoxycarbonyl)-2-phenyl-1H-indo -1-yl]acetic acid in DCM (0.04 M), DIPEA (3 eq), tert-butyl methyl[2-(methylamino)ethyl]carbamate (2 eq) (prepared as described in European patent application publication EP0296811, from commercially available N,N'-dimethylethylenediamine) and HATU (2 eq) were added, and the mixture stirred at RT for 2 h. The solution was diluted with DCM and washed with a saturated aqueous solution of $NH_4Cl$, a saturated aqueous solution of $NaHCO_3$ and brine before being dried over $Na_2SO_4$, filtered and concentrated in vacuo. The crude was then used in the next step without any further purification. ($ES^+$) m/z 562 $(M+H)^+$

Step 5: 1-{2-[{2-[(tert-butoxycarbonyl)(methyl)amino]ethyl}(methyl)amino]-2-oxoethyl}-3-cyclohexyl-2-phenyl-1H-indole-6-carboxylic acid The crude methyl 1-{2-[{2-[tert-butoxycarbonyl)(methyl)amino]ethyl}(methyl)amino]-2-oxoethyl}-3-cyclohexyl-2-phenyl-1H-indole-6-carboxylate in dioxane/$H_2O$/MeOH solution (1:1:1; 0.06 M) was treated with an aqueous solution of KOH (5 N) (3 eq). The solution was stirred at 60° C. for 4h. The volume of the solution was reduced in vacuo, and the mixture acidified with HCl (1N) before extracting with EtOAc (2×). The combined organic fractions were washed with brine, before being dried over $Na_2SO_4$, filtered and concentrated in vacuo. The crude was then used in the next step without any further purification. ($ES^+$) m/z 548 $(M+H)^+$

Step 6: N-benzyl-3-chloropropane-1-sulfonamide 3-chloro-propylsulfonyl chloride was added dropwise to a stirred solution of benzylamine (1 eq) and triethylamine (1.1 eq) in DCM (0.6 M) at 0° C. The solution was stirred at RT overnight. The solvent was then removed in vacuo, $Et_2O$ was added to get a precipitate that was eliminated by filtration, while the filtrate was concentrated in vacuo. Subsequent addition of PE resulted in the formation of a white precipitate that was collected by filtration to afford the title compound (86%). $^1$H NMR (400 MHz, DMSO-$d_6$, 300 K) δ 2.02-2.09 (m, 2H), 3.03-3.07 (m, 2H), 3.67 (t, J 6.6, 2H), 4.14 (d, J6.1, 2H), 7.25-7.30 (m, 1H), 7.32-7.36 (m, 4H), 7.73 (t, J 6.1, 1H).

Step 7: tert-butyl {2-[{[6-({benzyl[(3-chloropropyl)sulfonyl]-amino}carbonyl)-3-cyclohexyl-2-phenyl-1H-indol-1-yl]acetyl}(methyl)amino]ethyl}methylcarbamate A solution of the crude 1-{2-[{2-[(tert-butoxycarbonyl)(methyl)amino]ethyl}(methyl)amino]-2-oxoethyl}-3-cyclohexyl-2-phenyl-1H-indole-6-carboxylic acid in DCM (0.04 M) was treated with DMAP (2.5 eq), N-benzyl-3-chloropropane-1-sulfonamide (1.5 eq) and EDC (1.5 eq). The reaction was left stirring at 40° C. overnight. Further DMAP (2.5 eq), N-benzyl-3-chloropropane-1-sulfonamide (1.5 eq) and EDC (1.5 eq) were added and the reaction left to stir at 40° C. for another night. The mixture was diluted with DCM and washed with an aqueous solution of HCl (1N), a saturated aqueous solution of $NaHCO_3$ and brine before being dried over $Na_2SO_4$, filtered and concentrated in vacuo. The crude was then used in the next step without any further purification. ($ES^+$) m/z 777 $(M+H)^+$

Step 8: N-benzyl-N-[(3-chloropropyl)sulfonyl]-3-cyclohexyl-1-(2-{methyl[2-(methylamino)ethyl]amino}-2-oxoethyl)-2-phenyl-1H-indole-6-carboxamide hydrochloride A solution of the crude tert-butyl {2-[{[6-({benzyl[(3-chloropropyl)sulfonyl]amino}carbonyl)-3-cyclohexyl-2-phenyl-1H-indol-1-yl]acetyl}(methyl)amino]ethyl}methylcarbamate in DCM (0.09 M) was treated with TFA (140 eq) at 0° C. The reaction was allowed to reach RT in about 1 h. The solvent was then removed in vacuo, a 2 M solution HCl in $Et_2O$ was added and the volatiles removed in vacuo. MeCN was added and the precipitate was collected by filtration to afford clean compound (30%). ($ES^+$) m/z 677 $(M+H)^+$

Step 9: 16-cyclohexyl-3,6-dimethyl-17-phenyl-4,5,6,7,8,9-hexahydro-1H-13,15-(ethanediylidene)pyrrolo[2,1-f][1,2,7,10,13]thiatetraazacyclohexadecine-2,12(3H)-dione 10,10-dioxide DIPEA (40 eq) was added to N-benzyl-N-[(3-chloropropyl)sulfonyl]-3-cyclohexyl-1-(2-{methyl-[2-(methylamino)ethyl]amino}-2-oxoethyl)-2-phenyl-1H -indole-6-carboxamide hydrochloride in DMF (0.007 M). The reaction mixture was heated in a microwave system at 180° C. for 2800s. Then 10% Pd/C, (1:1 weight:weight with respect to substrate) was added, and the reaction stirred under a hydrogen atmosphere overnight. The reaction was flushed with $N_2$, filtered and concentrated in vacuo. The crude was then purified by automated RP-HPLC (stationary phase: column SYMMETRY prep. C18, 7 μm, 19×300 mm. Mobile phase: MECN/$H_2O$ buffered with 0.1% TFA). Fractions containing the pure compound were combined and freeze dried to afford the title compound as a white powder (24%). $^1$H NMR (500 MHz, DMSO-$d_6$ + TFA, 292 K) δ1.16-1.32 (m, 3H), 1.64-2.11 (m, 9H), 2.57-2.60 (m, 1H), 2.84 (s, 3H), 3.12 (s, 3H), 3.19-3.31 (m, 4H), 3.44-3.60 (m, 3H), 3.73-3.82 (m, 1H), 4.82-4.92 (m, 2H), 7.23-7.42 (m, 2H), 7.43-7.61 (m, 4H), 7.86-7.91 (m, 2H), 8.90-9.11 (b s, 1H); ($ES^+$) m/z 551 $(M+H)^+$

EXAMPLE 15

16-cyclohexyl-17-(4-methoxyphenyl)-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide

Step 1: tert-butyl benzyl[(3-chloropropyl)sulfonyl]carbamate

Benzylamine (1 eq.) was dissolved in anhydrous DCM (0.5 M) and $Et_3N$ (1.1 eq.) was added; after cooling at 0° C., 1-chloro-3-propanesulfonyl chloride was slowly added and the mixture was stirred at RT for 20 h. All volatiles were evaporated in vacuo and the residue taken up with $Et_2O$; the precipitate was filtered off and the filtrate was concentrated; addition of PE afforded N-benzyl-3-chloropropane-1-sulfonamide as a white solid (87%). ($ES^+$) m/z 248 $(M+H^+)$. Di-tert-butyl dicarbonate (1.5 eq.) was slowly added to an ice-cooled 0.45 M THF solution of N-benzyl-3-chloropropane-1-sulfonamide. DMAP (0.1 eq.) was then added and the reaction stirred overnight at RT. All volatiles were removed in vacuo and the crude diluted with EtOAc, washed with HCl, sat. aq. NaHCO$_3$ and brine. After drying over Na$_2$SO$_4$, all volatiles were evaporated in vacuo and the residual material used in the next step without purification. (ES$^+$) m/z 348, 350 (M+H$^+$).

Step 2: tert-butyl benzyl[(3-{methyl[2-(methylamino)ethyl]amino}propyl)sulfonyl]carbamate Tert-butyl benzyl[(3-chloropropyl)sulfonyl]carbamate was dissolved in MeCN (0.2 M) and N,N-dimethylethane-1,2-diamine (5 eq.) was added followed by K$_2$CO$_3$ (5 eq.). The mixture was stirred at 65° C. overnight. The solvent was removed under reduced pressure and the residual material was dissolved in EtOAc and washed with water. After drying over Na$_2$SO$_4$, all volatiles were evaporated in vacuo and the residual material used in the next step without purification. MS (ES$^+$) m/z 400 (M+H)$^+$.

Step 3: tert-butyl[(3-{methyl[2-(methylamino)ethyl]amino}propyl)sulfonyl]carbamate Pearlman's catalyst (0.10 eq.) was suspended in a 0.35 M EtOH solution of tert-butyl benzyl[(3-{methyl[2-(methylamino)ethyl]amino}propyl)sulfonyl]carbamate and the mixture was stirred under an hydrogen atmosphere for 4h. The crude was filtered on a CELITE pad and washed with EtOH; after evaporation of the solvent, the product was obtained as white solid, which was used without further characterisation (98% yield, two steps). (ES$^+$) m/z 310 (M+H)$^+$.

Step 4: methyl 2-bromo-3-cyclohexyl-1-(3,6,14,14-tetramethyl-10,10-dioxido-12-oxo-13-oxa-10-thia-3,6,11-triazapentadec-1-O-1H-indole-6-carboxylate Methyl 2-bromo-3-cyclohexyl-1-(2,2-dimethoxyethyl)-1H-indole-6-carboxylate (prepared as described in International patent application publication WO 2006/046030) was dissolved in THF (0.2M), aq. 6N HCl (30 eq.) was added, and the mixture was stirred at 65° C. for 1 h; after removal of the solvents in vacuo the in vacuo, the crude aldehyde was dissolved in MeOH (0.1M). tert-Butyl [(3-{methyl[2-(methylamino)ethyl]amino}propyl)sulfonyl]carbamate (2 eq.), NEt$_3$ (3 eq.), AcOH (5 eq.) and NaCNBH$_3$ (2 eq.) were added, and the mixture was left stirring at RT for 4h. Water was added to the residue obtained after evaporation of the solvents. The mixture was extracted twice with EtOAc. The combined organic phases were washed with brine and dried over Na$_2$SO$_4$. All volatiles were evaporated in vacuo. The residual material was purified by FC (EtOAc/MeOH 5:1 with 2% of NEt$_3$) to afford the title compound (63%). (ES$^+$): 671.6, 673.6.

Step 5: 17-bromo-16-cyclohexyl-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide The foregoing compound was dissolved in DCM/TFA 3:1 (0.05 M) and the mixture was left standing at RT. After 1 h all volatiles were evaporated in vacuo. The residue was dissolved in MeOH (0.05M) and 1 M aq. KOH solution (10 eq.) was added. The mixture was left stirring at 65° C. for 4h. After cooling to 0° C. the pH of the solution was adjusted with 1 M aq. HCl to pH 6. The resulting suspension was extracted with EtOAc. The combined organic phases were washed with brine and dried over Na$_2$SO$_4$. All volatiles were evaporated in vacuo. The residual material (1-{2-[{2-[[3-(aminosulfonyl)propyl](methyl)amino]ethyl}(methyl)amino]ethyl}-2-bromo-3-cyclohexyl-1H-indole-6-carboxylic acid) was dissolved in DCM (0.03 M). DMAP (3 eq.) and EDC (2 eq.) were added, and the solution was left stirring at 40° C. overnight. The residue obtained after evaporation of all volatiles was purified by FC (EtOAc/MeOH 5:1 with 2% of TEA) to give the title compound (65% over three steps). (ES$^+$): 539.2, 541.2.

Step 6: 16-cyclohexyl-17-(4-methoxyphenyl)-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide The foregoing compound and (4-methoxyphenyl)boronic acid (1.5 eq) were dissolved in dioxane (0.1 M) and 2M aqueous Na$_2$CO$_3$ (6 eq.) was added. The solution was degassed by bubbling nitrogen, Pd(PPh$_3$)Cl$_2$ (0.2 eq.) was added, and the reaction mixture was refluxed for 1 h; after cooling EtOAc was added and the solution washed with water and brine, dried over Na$_2$SO$_4$ and concentrated. The title compound was isolated by FC (EtOAc/MeOH 4:1 with 2% of NEt$_3$) followed by RP-HPLC to give the title compound as bis-TFA salt (20%). $^1$H NMR (400 MHz, DMSO-d$_6$, 300 K, bis TFA-salt) δ 8.20 (s, 1H), 7.91 (d, 1H, J 8.5), 7.53 (d, 1H, J 8.5), 7.37 (d, 2H, J 8.6), 7.14 (d, 2H, J 8.6), 4.40 (b.s, 2H), 3.85 (s, 3H), 3.60-3.51 (m, 4H), 3.50 (b.s, 2H), 3.40-3.36 (m, 2H), 3.08 (b.s, 2H), 2.83 (s, 3H), under DMSO (m, 1H), 2.61 (s, 3H), 2.21-2.13 (m, 2H), 1.85-1.63 (m, 7H), 1.29-1.13 (m, 3H); (ES$^+$): 567.6.

EXAMPLE 16

16-cyclohexyl-3,6-dimethyl-17-(2-thienyl)-2,3,4,5,6,7,8,9-octahydro-1H-13,15-(ethanediylidene)pyrrolo[2,1-f][1,2,7,10,13]thiatetraazacyclohexadecin-12-one 10,10-dioxide The compound was prepared in analogy to Example 15, Step 6, substituting (4-methoxyphenyl)boronic acid with 2-thienylboronic acid. The title compound was isolated by FC (EtOAc/MeOH 4:1 with 2% of NEt$_3$) followed by RP-HPLC to give the title compound as its bis-TFA salt (15%). $^1$H NMR (400 MHz, DMSO-d$_6$, 300 K, bis TFA-salt) δ 8.19 (s, 1H), 7.94 (d, 1H, J 8.6), 7.90 (b.d, 1H, J 4.3), 7.52 (d, 1H, J 8.6), 7.36 (b.d, 1H, J 2.5), 7.94 (dd, 1H, J 3.5, 5.0), 4.49 (b.s, 2H), 3.61-3.52 (m, 4H), 3.51 (b.s, 2H), 3.41-3.37 (m, 2H), 3.17 (b.s, 2H), 2.83 (s, 3H), 2.73-2.65 (m, 1H), 2.70 (s, 3H), 2.23-2.14 (m, 2H), 1.80-1.65 (m, 7H), 1.33-1.17 (m, 3H); (ES$^+$): 543.5.

The following tables contain further examples prepared in an analogous manner:

TABLE 5

| | 16-membered macrocycles | | | |
|---|---|---|---|---|
| Example no. | Compound name | Structure | procedure | m/z (ES+) |
| 14=501 | 16-cyclohexyl-3,6-dimethyl-17-phenyl-4,5,6,7,8,9-hexahydro-1H-13,15-(ethanediylidene)pyrrolo[2,1-f][1,2,7,10,13]thiatetraazacyclo-hexadecine-2,12(3H)-dione 10,10-dioxide | | A, B | 551.6 |
| 15=502 | 16-cyclohexyl-17-(4-methoxyphenyl)-3,6-dimethyl-2,3,4,5,6,7,8,9-octahydro-1H-13,15-(ethanediylidene)pyrrolo[2,1-f][1,2,7,10,13]thiatetraazacyclo-hexadecin-12-one 10,10-dioxide | | D | 567.4 |
| 16=503 | 16-cyclohexyl-3,6-dimethyl-17-(2-thienyl)-2,3,4,5,6,7,8,9-octahydro-1H-13,15-(ethanediylidene)pyrrolo[2,1-f][1,2,7,10,13]thiatetraazacyclo-hexadecin-12-one 10,10-dioxide | | D | 543.4 |

TABLE 5-continued 16-membered macrocycles

| Example no. | Compound name | Structure | procedure | m/z (ES+) |
|---|---|---|---|---|
| 504 | 16-cyclohexyl-3,6-dimethyl-17-phenyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide | 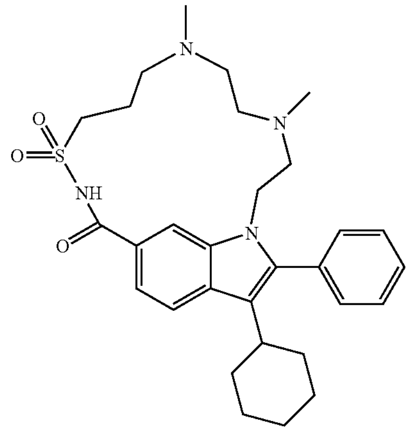 | D | 537.6 |
| 505 | 17-chloro-16-cyclohexyl-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide | 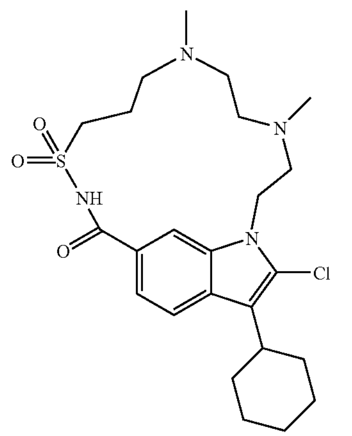 | B, C | 495.3, 497.3 |
| 506 | 16-cyclohexyl-17-(3-furyl)-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide | 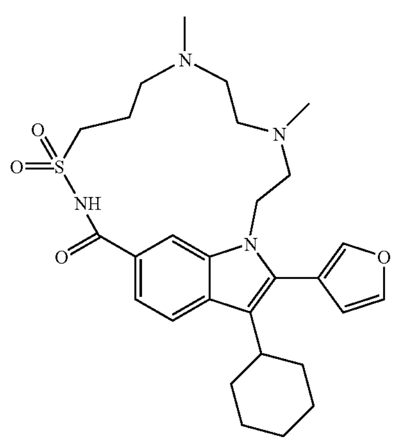 | D | 527.4 |

TABLE 5-continued 16-membered macrocycles

| Example no. | Compound name | Structure | procedure | m/z (ES+) |
|---|---|---|---|---|
| 507 | 16-cyclohexyl-17-(2-methoxyphenyl)-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide | 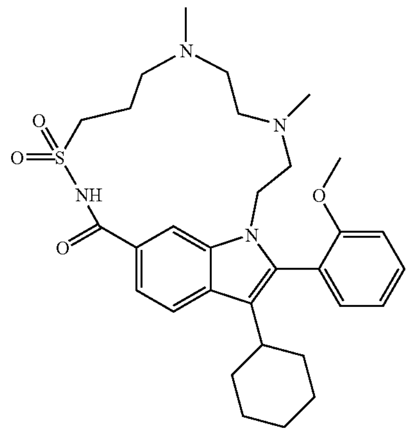 | D | 567.6 |

TABLE 6

17-membered macrocycles

| Example no. | Compound name | Structure | procedure | m/z (ES+) |
|---|---|---|---|---|
| 601 | 17-cyclohexyl-3,6-dimethyl-18-phenyl-3,4,5,6,7,8,9,10-octahydro-14,16-(ethanediylidene)pyrrolo[2,1-f][1,2,7,10,13]thiatetraazacycloheptadecine-2,13-dione 11,11-dioxide | 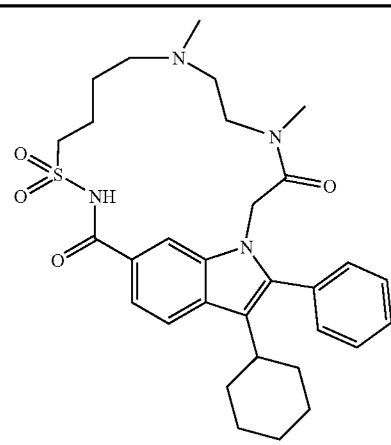 | A, B | 565 |

The invention claimed is:

1. A compound of formula (I):

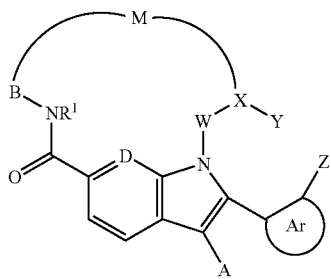

or a pharmaceutically acceptable salt thereof, wherein

Ar is a moiety containing at least one aromatic ring and possesses 5-, 6-, 9- or 10-ring atoms optionally containing 1, 2 or 3 heteroatoms independently selected from N, O and S, which ring is optionally substituted by groups $Q^1$ and $Q^2$;

$Q^1$ is halogen, hydroxy, $C_{1-6}$alkyl, $C_{1-6}$alkoxy, aryl, heteroaryl, $CONR^aR^b$, $(CH_2)_{0-3}NR^aR^b$, $O(CH_2)_{1-3}NR^aR^b$, $O(CH_2)_{0-3}CONR^aR^b$, $O(CH_2)_{0-3}$aryl, $O(CH_2)_{0-3}$heteroaryl, $O(CR^eR^f)$aryl, $O(CR^eR^f)$heteroaryl or $OCHR^c R^d$;

$R^a$ and $R^b$ are each independently selected from hydrogen, $C_{1-4}$alkyl and $C(O)C_{1-4}$alkyl;

or $R^a$, $R^b$ and the nitrogen atom to which they are attached form a heteroaliphatic ring of 4 to 7 ring atoms, where said ring is optionally substituted by halogen, hydroxy, $C_{1-4}$alkyl or $C_{1-4}$alkoxy;

$R^c$ and $R^d$ are each independently selected from hydrogen and $C_{1-4}$alkoxy;

or R$^c$ and R$^d$ are linked by a heteroatom selected from N, O and S to form a heteroaliphatic ring of 4 to 7 ring atoms, where said ring is optionally substituted by halogen, hydroxy, C$_{1-4}$alkyl or C$_{1-4}$alkoxy;
and wherein said C$_{1-4}$alkyl, C$_{1-4}$alkoxy and aryl groups are optionally substituted by halogen or hydroxy;
R$^e$ is hydrogen or C$_{1-6}$alkyl;
R$^f$ is C$_{1-6}$alkyl;
Q$^2$ is halogen, hydroxy, C$_{1-4}$alkyl or C$_{1-4}$alkoxy, where said C$_{1-4}$alkyl and C$_{1-4}$alkoxy groups are optionally substituted by halogen or hydroxy;
or Q$^1$ and Q$^2$ may be linked by a bond or a heteroatom selected from N, O and S to form a ring of 4 to 7 atoms, where said ring is optionally substituted by halogen, hydroxy, C$_{1-4}$alkyl or C$_{1-4}$alkoxy;
A is C$_{3-6}$alkyl or C$_{2-6}$alkenyl,
or A is a non-aromatic ring of 3 to 8 ring atoms where said ring may contain a double bond and/or may contain a O, S, SO, SO$_2$ or NH moiety,
or A is a non-aromatic bicyclic moiety of 4 to 8 ring atoms,
and A is optionally substituted by halogen, hydroxy, C$_{1-4}$alkyl or C$_{1-4}$alkoxy;
D is N or CR$^g$;
R$^g$ is hydrogen, fluorine, chlorine, C$_{1-4}$alkyl, C$_{2-4}$alkenyl or C$_{1-4}$alkoxy, where said C$_{1-4}$alkyl, C$_{2-4}$alkenyl and C$_{1-4}$alkoxy groups are optionally substituted by hydroxy or fluorine;
W is a bond, C=O, O, S(O)$_{0-2}$ or —(CR$^{10}$R$^{11}$)—(CR$^{12}$R$^{13}$)$_{0-1}$—;
X is —CR$^{14a}$— or N; Y is a bond, C=O, O, —CR$^{14}$R$^{15}$— or NR$^{14}$; and Z is a bond, C=O, O, S(O)$_{0-2}$ or —(CR$^{10}$R$^{11}$)—(CR$^{12}$R$^{13}$)$_{0-1}$— or NR$^{10}$; and none, one or two of W, Y and Z are a bond;
or X is C=O, O, —CR$^{14b}$R$^{15b}$— or NR$^{14b}$; and Y is hydrogen or absent and Z is hydrogen or a group Q$^1$ or Q$^2$;
R$^{10}$, R$^{11}$, R$^{12}$, R$^{13}$, R$^{14}$, R$^{14a}$, R$^{14b}$, R$^{15}$ and R$^{15b}$ are each independently selected from hydrogen, hydroxy, C$_{1-6}$alkyl, C$_{2-6}$alkenyl, C$_{1-6}$alkoxy, C(O)C$_{1-6}$alkyl, Het, (CH$_2$)$_{0-3}$NR$^{16}$R$^{17}$, C(O)(CH$_2$)$_{0-3}$NR$^{16}$R$^{17}$, NHC(O)(CH$_2$)$_{0-3}$NR$^{16}$R$^{17}$, O(CH$_2$)$_{1-3}$NR$^{16}$R$^{17}$, S(O)$_{0-2}$(CH$_2$)$_{0-3}$ NR$^{16}$R$^{17}$ and C(O)(CH$_2$)$_{0-3}$OR$^{16}$;
or one of R$^{10}$, R$^{14}$, R$^{14a}$ and R$^{14b}$ is linked to R$^{22}$ or R$^{23}$ to form a ring of 4 to 10 atoms, where said ring is optionally substituted by halogen, hydroxy, C$_{1-4}$alkyl or C$_{1-4}$alkoxy;
or, when X is —CR$^{14a}$— and Z is —CR$^{10}$R$^{11}$— or NR$^{10}$, R$^{10}$ is joined to R$^{14a}$ to form a —(CH$_2$)$_{1-4}$ group, optionally substituted by C$_{1-4}$alkyl;
Het is a heteroaliphatic ring of 4 to 7 ring atoms, which ring may contain 1, 2 or 3 heteroatoms selected from N, O or S or a group S(O), S(O)$_2$, NH or NC$_{1-4}$alkyl;
R$^{16}$ and R$^{17}$ are independently selected from hydrogen, C$_{1-6}$alkyl and (CH$_2$)$_{0-4}$NR$^{18}$R$^{19}$;
or R$^{16}$, R$^{17}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;
R$^{18}$ and R$^{19}$ are independently selected from hydrogen and C$_{1-6}$alkyl;
or R$^{18}$, R$^{19}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;
R$^1$ is hydrogen or C$_{1-6}$alkyl;
B is —CR$^{20}$R$^{21}$—, —C(=O)—, —SO— or —SO$_2$—;
R$^{20}$ and R$^{21}$ are independently selected from hydrogen and C$_{1-6}$alkyl;
or R$^{20}$ and R$^{21}$, together with the carbon atom to which they are joined, form a C$_{3-6}$cycloalkyl group;
M is C$_{4-8}$alkylene or C$_{4-8}$alkenylene, optionally substituted by R$^{22}$, where 1, 2 or 3 of the carbon atoms in the C$_{4-8}$alkylene or C$_{4-8}$alkenylene groups is optionally replaced by O, NR$^{23}$, S, SO, SO$_2$, piperidinyl, piperazinyl or pyrrolidinyl,
where each R$^{23}$ is independently hydrogen, C$_{1-6}$alkyl, C$_{2-6}$alkenyl, (CH$_2$)$_{0-3}$C$_{3-6}$cycloalkyl, (CH$_2$)$_{1-3}$OH, C$_{1-6}$alkoxy, C(O)C$_{1-6}$alkyl, (CH$_2$)$_{0-3}$aryl, (CH$_2$)$_{0-3}$Het, (CH$_2$)$_{0-3}$heteroaryl, (CH$_2$)$_{1-3}$NR$^{16}$R$^{17}$, C(O)(CH$_2$)$_{1-3}$NR$^{16}$R$^{17}$, S(O)$_{0-2}$(CH$_2$)$_{1-3}$NR$^{16}$R$^{17}$, C(O)(CH$_2$)$_{1-3}$OR$^{16}$, (CH$_2$)$_{1-3}$(CH$_2$)$_{0-3}$aryl,
or R$^{23}$ is linked to one of R$^{10}$, R$^{14}$, R$^{14a}$ and R$^{14b}$ to form a ring of 4 to 10 atoms as hereinbefore described;
or where 2 or 3 of the carbon atoms in the C$_{4-8}$alkylene or C$_{4-8}$alkenylene group are replaced by NR$^{23}$, then the R$^{23}$ groups can be joined to form a —(CH$_2$)—$_{1-3}$ group, optionally substituted by C$_{1-2}$alkyl,
where R$^{22}$ is halo, C$_{1-4}$alkyl, (CH$_2$)$_{0-3}$C$_{3-8}$cycloalkyl, (CH$_2$)$_{0-3}$aryl, (CH$_2$)$_{0-3}$heteroaryl, (CH$_2$)$_{0-3}$Het, oxo or (CH$_2$)$_{0-3}$NR$^{16}$R$^{17}$,
or R$^{22}$ is linked to one of R$^{10}$, R$^{14}$, R$^{14a}$ and R$^{14b}$ to form a ring of 4 to 10 atoms as hereinbefore described.

2. The compound according to claim 1, wherein said compound is of formula (Ia):

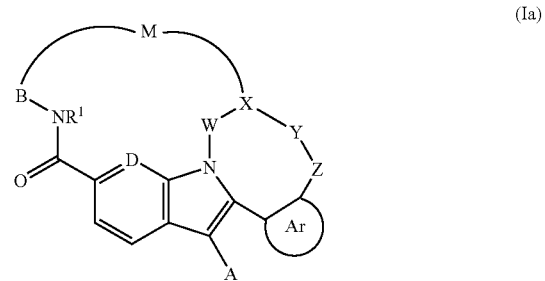

(Ia)

wherein X is —CR$^{14a}$— or N; Y is a bond, C=O, O, —CR$^{14}$R$^{15}$— or NR$^{14}$; and Z is a bond, C=O, O, S(O)$_{0-2}$, —(CR$^{10}$R$^{11}$)—(CR$^{12}$R$^{13}$)$_{0-1}$— or NR$^{10}$; and none, one or two of W, Y and Z are a bond.

3. The compound according to claim 1, wherein said compound is of formula (Iao):

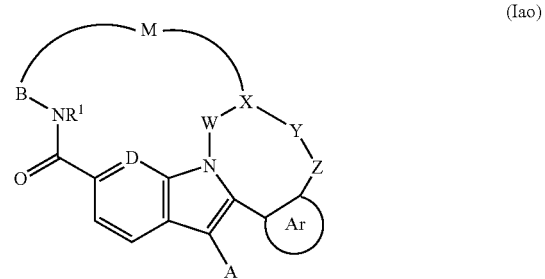

(Iao)

or a pharmaceutically acceptable salt thereof, wherein

Z is a bond, C=O, O, S(O)$_{0-2}$, —(CR$^{10}$R$^{11}$)—(R$_{12}$R$^{13}$)$_{0-1}$— or NR$^{10}$;
and none, one or two of W, Y and Z are a bond;
X is —CR$^{14a}$— or N;
R$^{10}$, R$^{11}$, R$^{12}$, R$^{13}$, R$^{14}$, R$^{14a}$ and R$^{15}$ are each independently selected from hydrogen, hydroxy, C$_{1-6}$alkyl, C$_{2-6}$alkenyl, C$_{1-6}$alkoxy, C(O)C$_{1-6}$alkyl, Het, (CH$_2$)$_{0-3}$NR$^{16}$R$^{17}$, C(O)(CH$_2$)$_{0-3}$NR$^{16}$R$^{17}$, NHC(O)(CH$_2$)$_{0-3}$NR$^{16}$R$^{17}$, O(CH$_2$)$_{1-3}$NR$^{16}$R$^{17}$, S(O)$_{0-2}$(CH$_2$)$_{0-3}$R$^{16}$R$^{17}$ and C(O)(CH$_2$)$_{0-3}$OR$^{16}$;
or one of R$^{10}$, R$^{14}$ and R$^{14a}$ is linked to R$^{22}$ or R$^{23}$ to form a ring of 4 to 10 atoms, where said ring is optionally substituted by halogen, hydroxy, C$_{1-4}$alkyl or C$_{1-4}$alkoxy;
Het is a heteroaliphatic ring of 4 to 7 ring atoms, which ring may contain 1, 2 or 3 heteroatoms selected from N, O or S or a group S(O), S(O)$_2$, NH or NC$_{1-4}$alkyl;
R$^{16}$ and R$^{17}$ are independently selected from hydrogen, C$_{1-6}$alkyl and (CH$_2$)$_{0-4}$NR$^{18}$R$^{19}$;
or R$^{16}$, R$^{17}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;
R$^{18}$ and R$^{19}$ are independently selected from hydrogen and C$_{1-6}$alkyl;
or R$^{18}$, R$^{19}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;
M is C$_{4-8}$alkylene or C$_{4-8}$alkenylene, optionally substituted by R$^{22}$, where 1, 2 or 3 of the carbon atoms in the C$_{4-8}$alkylene or C$_{4-8}$alkenylene groups is optionally replaced by O, NR$^{23}$, S, SO, SO$_2$, piperidinyl, piperazinyl or pyrrolidinyl,
where R$^{23}$ is hydrogen or C$_{1-6}$alkyl, or R$^{23}$ is linked to one of R$^{10}$, R$^{14}$ and R$^{14a}$ to form a ring of 4 to 10 atoms as hereinbefore described;
where R$^{22}$ is halo, C$_{1-4}$alkyl, (CH$_2$)$_{0-3}$C$_{3-8}$cycloalkyl, (CH$_2$)$_{0-3}$aryl, (CH$_2$)$_{0-3}$heteroaryl, (CH$_2$)$_{0-3}$Het or oxo,
or R$^{22}$ is linked to one of R$^{10}$, R$^{14}$ and R$^{14a}$ to form a ring of 4 to 10 atoms as hereinbefore described.

4. The compound according to claim 2 in which Z is a bond, O, —CH$_2$— or —CH$_2$CH$_2$—.

5. The compound according to claim 2 in which Y is selected from —CH$_2$— and a bond.

6. The compound according to claim 2 in which X is —CH—.

7. The compound according to claim 1, wherein the compound is of formula (Ib):

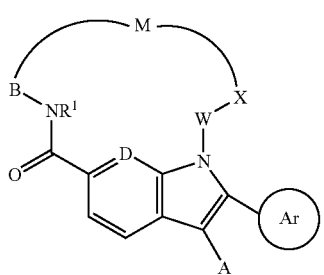

(Ib)

or a pharmaceutically acceptable salt therof, wherein X is C=O, O, —CR$^{14b}$R$^{15b}$— or NR$^{14b}$.

8. The compound according to claim 1, wherein the compound is of formula (Ibo):

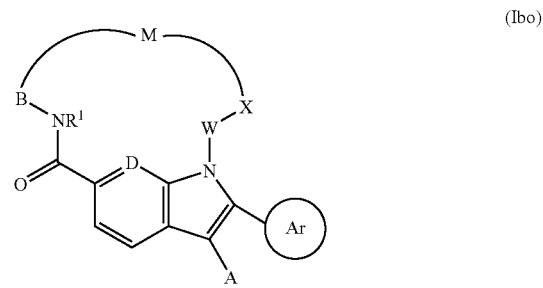

(Ibo)

or a pharmaceutically acceptable thereof, wherein
Ar is a moiety containing at least one aromatic ring and possesses 5-, 6-, 9- or 10-ring atoms optionally containing 1, 2 or 3 heteroatoms independently selected from N, O and S, which ring is optionally substituted by groups Q$^1$ and Q$^2$;
Q$^1$ is halogen, hydroxy, C$_{1-6}$alkyl, C$_{1-6}$alkoxy, aryl, heteroaryl, CONR$^a$R$^b$, (CH$_2$)$_{0-3}$NR$^a$R$^b$, O(CH$_2$)$_{1-3}$NR$^a$R$^b$, O(CH$_2$)$_{0-3}$CONR$^a$R$^b$, O(CH$_2$)$_{0-3}$aryl, O(CH$_2$)$_{0-3}$heteroaryl, O(CR$^e$R$^f$)aryl, O(CR$^e$R$^f$)heteroaryl or OCHR$^c$R$^d$;
R$^a$ and R$^b$ are each independently selected from hydrogen, C$_{1-4}$alkyl and C(O)C$_{1-4}$alkyl;
or R$^a$, R$^b$ and the nitrogen atom to which they are attached form a heteroaliphatic ring of 4 to 7 ring atoms, where said ring is optionally substituted by halogen, hydroxy, C$_{1-4}$alkyl or C$_{1-4}$alkoxy;
R$^c$ and R$^d$ are each independently selected from hydrogen and C$_{1-4}$alkoxy;
or R$^c$ and R$^d$ are linked by a heteroatom selected from N, O and S to form a heteroaliphatic ring of 4 to 7 ring atoms, where said ring is optionally substituted by halogen, hydroxy, C$_{1-4}$alkyl or C$_{1-4}$alkoxy;
and wherein said C$_{1-4}$alkyl, C$_{1-4}$alkoxy and aryl groups are optionally substituted by halogen or hydroxy;
R$^e$ is hydrogen or C$_{1-6}$alkyl;
R$^f$ is C$_{1-6}$alkyl;
Q$^2$ is halogen, hydroxy, C$_{1-4}$alkyl or C$_{1-4}$alkoxy, where said C$_{1-4}$alkyl and C$_{1-4}$alkoxy groups are optionally substituted by halogen or hydroxy;
or Q$^1$ and Q$^2$ may be linked by a bond or a heteroatom selected from N, O and S to form a ring of 4 to 7 atoms, where said ring is optionally substituted by halogen, hydroxy, C$_{1-4}$alkyl or C$_{1-4}$alkoxy;
A is C$_{3-6}$alkyl or C$_{2-6}$alkenyl,
or A is a non-aromatic ring of 3 to 8 ring atoms where said ring may contain a double bond and/or may contain a O, S, SO, SO$_2$ or NH moiety,
or A is a non-aromatic bicyclic moiety of 4 to 8 ring atoms, and A is optionally substituted by halogen, hydroxy, C$_{1-4}$alkyl or C$_{1-4}$alkoxy;
D is N or CR$^g$;
R$^g$ is hydrogen, fluorine, chlorine, C$_{1-4}$alkyl, C$_{2-4}$alkenyl or C$_{1-4}$alkoxy, where said C$_{1-4}$alkyl, C$_{2-4}$alkenyl and C$_{1-4}$alkoxy groups are optionally substituted by hydroxy or fluorine;
W is a bond, C=O, O, S(O)$_{0-2}$ or —(CR$^{10}$R$^{11}$)—(CR$^{12}$R$^{13}$)$_{0-1}$—;
X is C=O, O, —CR$^{14}$R$^{15}$— or NR$^{14}$;
R$^{10}$, R$^{11}$, R$^{12}$, R$^{13}$, R$^{14}$ and R$^{15}$ are each independently selected from hydrogen, hydroxy, C$_{1-6}$alkyl, C$_{2-6}$alkenyl, C$_{1-6}$alkoxy, C(O)C$_{1-6}$alkyl, (CH$_2$)$_{0-3}$aryl, (CH$_2$)$_{0-3}$heteroaryl, (CH$_2$)$_{0-3}$Het, (CH$_2$)$_{0-3}$NR$^{16}$R$^{17}$, C(O)

(CH$_2$)$_{0-3}$NR$^{16}$R$^{17}$, NHC(O)(CH$_2$)$_{0-3}$NR$^{16}$R$^{17}$, O(CH$_2$)$_{1-3}$NR$^{16}$R$^{17}$, S(O)$_{0-2}$(CH$_2$)$_{0-3}$R$^{16}$R$^{17}$ and C(O)(CH$_2$)$_{0-2}$OR$^{16}$;

or R$^{14}$ is linked to R$^{22}$ or R$^{23}$ to form a ring of 4 to 10 atoms, where said ring is optionally substituted by halogen, hydrogen, C$_{1-4}$alkyl or C$_{1-4}$alkoxy;

Het is a heteroaliphatic ring of 4 to 7 ring atoms, which ring may contain 1, 2 or 3 heteroatoms selected from N, O or S or a group 5(O), S(O)$_2$, NH or NC$_{1-4}$alkyl;

R$^{16}$ and R$^{17}$ are independently selected from hydrogen, C$_{1-6}$alkyl and (CH$_2$)$_{0-4}$NR$^{18}$R$^{19}$;

or R$^{16}$, R$^{17}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;

R$^{18}$ and R$^{19}$ are independently selected from hydrogen and C$_{1-6}$alkyl; or R$^{18}$, R$^{19}$ and the nitrogen atom to which they are attached form a heteroaliphatic ring of 4 to 7 ring atoms, which ring may optionally contain 1 or 2 more heteroatoms selected from O or S or a group S(O), S(O)$_2$, NH or NC$_{1-4}$alkyl, and which ring is optionally substituted by halogen, hydroxy, C$_{1-4}$alkyl or C$_{1-4}$alkoxy;

R$^1$ is hydrogen or C$_{1-6}$alkyl;

B is CR$^{20}$R$^{21}$—, —C(=O)—, —SO— or —SO$_2$—;

R$^{20}$ and R$^{21}$ are independently selected from hydrogen and C$_{1-6}$alkyl;

or R$^{20}$ and R$^{21}$, together with the carbon atom to which they are joined, form a C$_{3-6}$cycloalkyl group;

M is C$_{4-8}$alkylene or C$_{4-8}$alkenylene, optionally substituted by R$^{22a}$, where 1, 2 or 3 of the carbon atoms in the C$_{4-8}$alkylene or C$_{4-8}$alkenylene groups is optionally replaced by O, NR$^{23a}$, S, SO, SO$_2$, aryl, heteroaryl or Het, where R$^{23a}$ is hydrogen or C$_{1-6}$alkyl, or R$^{23a}$ is linked to R$^{14}$ to form a ring of 4 to 10 atoms as hereinbefore described;

where R$^{22a}$ is halo, C$_{1-4}$alkyl, (CH$_2$)$_{0-3}$C$_{3-8}$cycloalkyl, (CH$_2$)$_{0-3}$aryl, heteroaryl, Het or oxo, or R$^{22a}$ is linked to R$^{14}$ to form a ring of 4 to 10 atoms as hereinbefore described.

9. The compound according to claim 7 in which X is C=O or —CH$_2$—.

10. The compound according to claim 1 in which Ar is phenyl, 2-pyridyl, 3-pyridyl, 4-pyridyl, 2-furanyl or 3-furanyl, optionally substituted by groups Q$^1$ and Q$^2$.

11. The compound according to claim 1 in which A is cyclopentyl or cyclohexyl, optionally substituted by halogen, hydroxy, C$_{1-4}$alkyl or C$_{1-4}$alkoxy.

12. The compound according to claim 1 in which D is CR$^g$ where R$^g$ is hydrogen or C$_{1-4}$alkyl.

13. The compound according to claim 1 in which W is —CH$_2$— or —CH$_2$CH$_2$—.

14. The compound according to claim 1 in which R$^1$ is hydrogen or methyl.

15. The compound according to claim 1 in which B is —SO$_2$—.

16. The compound according to claim 1 in which M is C$_{5-8}$alkylene, optionally substituted by C$_{1-4}$alkyl or oxo, where 1 or 2 of the carbon atoms in the C$_{5-8}$alkylene group is replaced by O, NH or N(C$_{1-4}$alkyl).

17. The compound according to claim 1, wherein the compound is selected from the group consisting of:

(7R)-14-cyclohexyl-25-methyl-7,8-dihydro-6H-7,11-(epiminoethanoiminobutanothioiminomethano)indolo[1,2-e][1,5]benzoxazocine-15,21-dione 17,17-dioxide;

(7R)-14-cyclohexyl-24-methyl-7,8-dihydro-6H-7,11-(epiminoethanoiminopropanothioiminomethano)indolo[1,2-e][1,5]benzoxazocin-15-one 17,17-dioxide;

(7R)-14-cyclohexyl-21,24-dimethyl-7,8-dihydro-6H-7,11-(epiminoethanoiminopropanothioiminomethano)indolo[1,2-e][1,5]benzoxazocin-15-one 17,17-dioxide;

(7R)-14-[(1R,2S) or (1S,2R)-2-fluoro cyclohexyl]-21,24-dimethyl-7,8-dihydro-6H-7,11-(epiminoethanoiminopropanothioiminomethano)indolo[1,2-e][1,5]benzoxazocin-15-one 17,17-dioxide;

7 (R,S)-14-cyclohexyl-22-methyl-7,8-dihydro-6H-7,11-(ethanoiminobutanothioiminomethano)indolo[1,2-e][1,5]benzoxazocin-15-one 17,17-dioxide;

(7R)-14-cyclohexyl-20,24-dimethyl-7,8-dihydro-6H-7,11-(epiminopropanoiminoethanothioiminomethano)indolo[1,2-e][1,5]benzoxazocin-15-one 17,17-dioxide;

13-cyclohexyl-19,22-dimethyl-6,7-dihydro-10,6-(methanoiminothioethanoiminoethanoiminomethano)indolo[1,2-d][1,4]benzoxazepin-14-one 16,16-dioxide;

(7R)-14-cyclohexyl-22,25-dimethyl-7,8-dihydro-6H-7,11-(epiminoethanoiminobutanothioiminomethano)indolo[1,2-e][1,5]benzoxazocin-15-one 17,17-dioxide;

(7S)-14-cyclohexyl-21-methyl-7,8-dihydro-6H-7,11-(epoxyethanoiminopropanothioiminomethano)indolo[1,2-e][1,5]benzoxazocin-15-one 17,17-dioxide;

13-cyclohexyl-5,20,23-trimethyl-6,7-dihydro-5H-10,6-(methanoiminothiopropanoiminoethanoiminomethano)indolo[1,2-d][1,4]benzodiazepin-14-one 16,16-dioxide;

13-cyclohexyl-20,23-dimethyl-6,7-dihydro-5H-6,10-(epiminoethanoiminopropanothioiminomethano)indolo[2,1-a][2]benzazepin-14-one 16,16-dioxide;

8-cyclohexyl-19,22-dimethyl-1,12b-dihydro-5,1a-(methanoiminothiopropanoiminoethanoiminomethano)cyclopropa[c]indolo[2,1-a][2]benzazepin-13-one 15,15-dioxide;

13-cyclohexyl-20,23-dimethyl-6,7-dihydro-5H-10,6-(methanoiminothiopropanoiminoethanoiminomethano)indolo[2,1-a][2]benzazepin -14-one 16,16-dioxide;

16-cyclohexyl-3,6-dimethyl-17-phenyl-4,5,6,7,8,9-hexahydro-1H -13,15-(ethanediylidene)pyrrolo[2,1-f][1,2,7,10,13]thiatetraazacyclohexadecine-2,12(3H)-dione 10,10-dioxide;

16-cyclohexyl-17-(4-methoxyphenyl)-3,6-dimethyl-2,3,4,5,6,7,8,9-octahydro-1H-13,15-(ethanediylidene)pyrrolo[2,1-f ][1,2,7,10,13]thiatetra-azacyclohexadecin-12-one 10,10-dioxide;

16-cyclohexyl-3,6-dimethyl-17-(2-thienyl)-2,3,4,5,6,7,8,9-octahydro-1H-13,15-(ethanediylidene)pyrrolo[2,1-f][1,2,7,10,13]thiatetraazacyclohexadecin-12-one 10,10-dioxide;

(7R)-14-cyclohexyl-3-fluoro-21,24-dimethyl-7,8-dihydro-6H-7,11-(epiminoethanoiminopropanothioiminomethano)indolo[1,2-e][1,5]benzoxazocin-15-one 17,17-dioxide;

(7R)-14-cyclohexyl-2-fluoro-21,24-dimethyl-7,8-dihydro-6H-7,11-(epiminoethanoiminopropanothioiminomethano)indolo[1,2-e][1,5]benzoxazocin-15-one 17,17-dioxide;

16-cyclohexyl-3,6-dimethyl-17-phenyl-2,3,4,5,6,7,8,9-octahydro-1H-13,15-(ethanediylidene)pyrrolo[2,1-f][1,2,7,10,13]thiatetraazacyclo hexadecin-12-one 10,10-dioxide;

17-chloro-16-cyclohexyl-3,6-dimethyl-2,3,4,5,6,7,8,9-octahydro-1H-13,15-(ethanediylidene)pyrrolo[2,1-f][1,2,7,10,13]thiatetraazacyclo hexadecin-12-one 10,10-dioxide;

16-cyclohexyl-17-(3-furyl)-3,6-dimethyl-2,3,4,5,6,7,8,9-octahydro-1H-13,15-(ethanediylidene)pyrrolo[2,1-f][1,2,7,10,13]thiatetraazacyclo hexadecin-12-one 10,10-dioxide;

16-cyclohexyl-17-(2-methoxyphenyl)-3,6-dimethyl-2,3,4,5,6,7,8,9-octahydro-1H-13,15-(ethanediylidene)pyrrolo[2,1-f][1,2,7,10,13]thiatetraazacyclohexadecin-12-one 10,10-dioxide;

17-cyclohexyl-3,6-dimethyl-18-phenyl-3,4,5,6,7,8,9,10-octahydro-14,16-(ethanediylidene)pyrrolo[2,1-f][1,2,7,10,13]thiatetraazacycloheptadecine-2,13-dione 11,11-dioxide;

and pharmaceutically acceptable salts thereof.

18. A pharmaceutical composition which comprises an effective amount of a compound of the formula (I) according to claim 1 together with a pharmaceutically acceptable carrier.

19. A method of treating hepatitis C virus in a human or animal subject in need thereof, said method comprising administering to a human or animal subject a therapeutically effective amount of the compound according to claim 1 or a pharmaceutically acceptable salt thereof.

* * * * *